United States Patent
Berger et al.

(10) Patent No.: US 8,173,676 B2
(45) Date of Patent: May 8, 2012

(54) BENZYL, AMINES, A PROCESS FOR THEIR PRODUCTION AND THEIR USE AS ANTI-INFLAMMATORY AGENTS

(75) Inventors: Markus Berger, Berlin (DE); Jan Dahmen, Akarp (SE); Hartmut Rehwinkel, Berlin (DE); Stefan Jaroch, Berlin (DE); Heike Schäcke, Berlin (DE)

(73) Assignees: Bayer Pharma AG, Berlin (DE); AstraZeneca AB, Sodertalje (SE)

( * ) Notice: Subject to any disclaimer, the term of this patent is extended or adjusted under 35 U.S.C. 154(b) by 0 days.

(21) Appl. No.: 13/210,173

(22) Filed: Aug. 15, 2011

(65) Prior Publication Data

US 2011/0301347 A1 Dec. 8, 2011

Related U.S. Application Data

(62) Division of application No. 11/777,411, filed on Jul. 13, 2007, now Pat. No. 7,999,108.

(60) Provisional application No. 60/830,671, filed on Jul. 14, 2006.

(30) Foreign Application Priority Data

Jul. 14, 2006 (EP) .................... 06014665

(51) Int. Cl.
*A61K 31/04* (2006.01)
(52) U.S. Cl. ...... 514/313; 514/310; 514/248; 514/258.1
(58) Field of Classification Search ................. 514/313, 514/310, 248, 258.1
See application file for complete search history.

(56) References Cited

U.S. PATENT DOCUMENTS

| | | | |
|---|---|---|---|
| 4,189,453 | A | 2/1980 | Lorenz et al. |
| 7,129,270 | B2 | 10/2006 | JaRoch |
| 7,442,794 | B2 | 10/2008 | Rehwinkel et al. |
| 2005/0090559 | A1 | 4/2005 | Berger |
| 2005/0131226 | A1 | 6/2005 | Rehwinkel et al. |

FOREIGN PATENT DOCUMENTS

| GB | 1045180 A | 10/1966 |
|---|---|---|
| JP | 06-172321 | 6/1994 |
| WO | WO 0010977 A1 | 3/2000 |
| WO | WO 0210143 A | 2/2002 |
| WO | WO 2005/003098 A1 | 1/2005 |
| WO | WO 2005/035518 | 4/2005 |

OTHER PUBLICATIONS

Besedovsky, Nature Immunology, vol. 7, pp. 537, 2006.*
A.S. Demir et al: "Generation of acylanion equivalents from acylphosphonates via phosphonate-phosphate rearrangement: a highly prectical method for cross-benzoin reaction" Journal of Organic Chemistry., vol. 70, 2005, pp. 10584-10587, XP002458094 Usamerican Chemical Society, Washington, DC.
Database Beilstein [Online] Beilstein Institute for Organic Chemistry, Frankfurt-Main, DE; XP002458021 Database accession No. BRN: 401367 abstract & Indian j. Chem. Sect. B, 16, 1978, 92.
Database Beilstein [Online] Beilstein Institute for Organic Chemistry, Frankfurt-Main, DE; XP002458022 Database accession No. BRN: 407396 abstract & Aust J. Chem. 19, 1966,2389-2392.
G. Bartoli et al: "Asymmetric aminolysis of aromatic epoxides: a facile catalytic enantioselective synthesis of anti-beta-aminoalcohols" Organic Letters., vol. 6, No. 13, 2004, pp. 2173-2176, XP002425753 USACS, Washington, DC.
Kohyama Antimicrobial Agents and Chemotherapy, Apr. 1999, vol. 43(4), pp. 907-911.
Cooper, Am J. Respri Cirt Car Med, vol. 163(5), pp. 1198-1205, Apr. 2001, full text.
Leitner, Int J Immunopathol Pharmacol, vol. 20(1), pp. 25-26, Jan.-Mar. 2007, abstract only.

* cited by examiner

*Primary Examiner* — D M Seaman
(74) *Attorney, Agent, or Firm* — Millen, White, Zelano & Branigan, P.C.

(57) ABSTRACT

The present invention relates to the compounds of formula I,

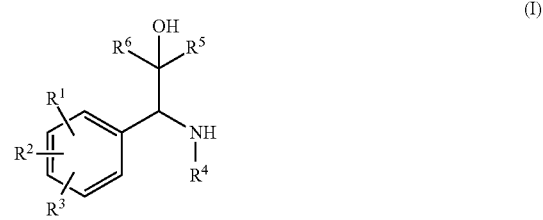

processes for their production and their use as anti-inflammatory agents.

10 Claims, No Drawings

BENZYL, AMINES, A PROCESS FOR THEIR PRODUCTION AND THEIR USE AS ANTI-INFLAMMATORY AGENTS

This patent application is a divisional application of U.S. patent application Ser. No. 11/777,411, filed Jul. 13, 2007, now U.S. Pat. No. 7,999,108 and claims the priority according to the Paris Convention of European Patent application No. EP 06014665.1 filed Jul. 14, 2006 as well as the benefit of the U.S. provisional application 60/830,671 filed Jul. 14, 2006 both of which are incorporated herein by reference.

From the prior art of DE 100 38 639 and WO 02/10143, anti-inflammatory agents of the following general formula

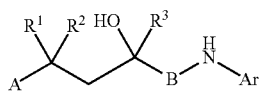

are known, in which the Ar radical comprises phthalides, thiophthalides, benzoxazinones or phthalazinones. In the experiment, these compounds show dissociations of action between anti-inflammatory and undesirable metabolic actions and are superior to the previously described nonsteroidal glucocorticoids or exhibit at least just as good an action.

Compounds structurally similar to those described in this patent application are disclosed in WO 2005/035518. Due to the manufacturing process these compound always do contain a mom

in which the bond between a and b or between b and c may be unsaturated (in other words they contain a —$CH_2$—CH$(CH_3)_2$, a —CH=C$(CH_3)_2$ or a —$CH_2$—C$(CH_3)$=$CH_2$ group). Compounds of such a composition are specifically disclaimed in the present application.

Further references that might be relevant for the present application are cited below:

G. Bartoli, et al., "Asymmetric aminolysis of aromatic epoxides: a facile catalytic enantioselective synthesis of anti-beta-aminoalcohols" Organic Letters, vol. 6, No. 13, 2004, pages 2173-2176;

WO 00/10977 A1 (Scripps Research Inst.)

US 2005/131226 A1 (Rehwinkel et al.)

Despite all efforts, the selectivity of the compounds of the prior art towards the glucocorticoid receptor (GR) compared to the other steroid receptors still requires improvement.

It was therefore the object of this invention to make compounds available whose selectivity towards the glucocorticoid receptor (GR) is improved compared to the other steroid receptors.

This object has been achieved by the compounds according to the claims.

This invention therefore relates to stereoisomers of general formula I

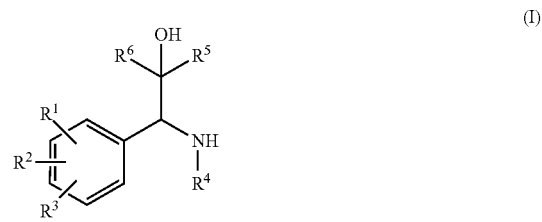

in which $R^1$ and $R^2$ independently of one another, mean a hydrogen atom, a hydroxy group, a halogen atom, an optionally substituted ($C_1$-$C_{10}$)-alkyl group, an optionally substituted ($C_1$-$C_{10}$)-alkoxy group, a ($C_1$-$C_{10}$)-alkylthio group, a ($C_1$-$C_5$)-perfluoroalkyl group, a cyano group, a nitro group, or $R^1$ and $R^2$ together mean a group that is selected from the groups —O—$(CH_2)_p$—O—, —O—$(CH_2)_p$—$CH_2$—, —O—CH=CH—, —$(CH_2)_{p+2}$—, —NH—$(CH_2)_{p+1}$, N($C_1$-$C_3$-alkyl)-$(CH_2)_{p+1}$, and —NH—N=CH—, in which p=1 or 2, and the terminal oxygen atoms and/or carbon atoms and/or nitrogen atoms are linked to directly adjacent ring-carbon atoms, or $NR^7R^8$, in which $R^7$ and $R^8$, independently of one another, means hydrogen, $C_1$-$C_5$-alkyl or (CO)—($C_1$-$C_5$)-alkyl, $R^3$ means a hydrogen atom, a hydroxy group, a halogen atom, a cyano group, or an optionally substituted ($C_1$-$C_{10}$)-alkyl group, a ($C_1$-$C_{10}$)-alkoxy group, a ($C_1$-$C_{10}$)-alkylthio group, or a ($C_1$-$C_5$)-perfluoroalkyl group, $R^4$ means a monocyclic, or bicyclic, aromatic, partially aromatic, or non-aromatic ring system, which optionally contains 1-4 nitrogen atoms, 1-2 oxygen atoms and/or 1-2 sulfur atoms and optionally is substituted in one or more places by a radical that is selected from the group carbonyl, halogen, hydroxy, or ($C_1$-$C_5$)-alkyl, which optionally can be substituted by 1-3 hydroxy groups, 1-3 ($C_1$-$C_5$)alkoxy groups, 1-3 $COOR^6$ groups, 1-3 COOH groups, 1-3 ($C_1$-$C_5$)alkoxy, 1-3 ($C_1$-$C_5$)-alkylthio, 1-3 ($C_1$-$C_5$)-perfluoroalkyl, 1-3 cyano and/or 1-3 nitro, or two substituents together form a group that is selected from the groups —O—$(CH_2)_p$—O—, —O—$(CH_2)_p$—$CH_2$—, —O—CH=CH—, —$(CH_2)_{p+2}$—, —NH—$(CH_2)_{p+1}$—, —N($C_1$-$C_3$-alkyl)-$(CH_2)_{p+1}$—, and —NH—N=CH—, in which p=1 or 2, and the terminal oxygen atoms and/or carbon atoms and/or nitrogen atoms are linked to directly adjacent ring-carbon atoms, $NR^7R^8$, in which $R^7$ and $R^8$, independently of one another, can be hydrogen, $C_1$-$C_5$-alkyl or (CO)—$C_1$-$C_5$-alkyl (CO)$NR^{11}R^{12}$, in which $R^{11}$ and $R^{12}$, independently of one another, mean hydrogen or a $C_1$-$C_5$-alkyl group, or a ($C_1$-$C_5$-alkylene)-O—(CO)—($C_1$-$C_5$)alkyl group, $R^5$ means a partially or completely fluorinated $C_1$-$C_3$-alkyl group, $R^6$ means a group selected from
- —$(C_1$-$C_{10})$-alkyl, which may be optionally partially or completely halogenated
- —$(C_2$-$C_{10})$-alkenyl,
- —$(C_2$-$C_{10})$-alkynyl,
- —$(C_1$-$C_8)$alkyl$(C_3$-$C_7)$cycloalkyl,
- —$(C_2$-$C_8)$alkenyl$(C_3$-$C_7)$cycloalkyl,
- —$(C_1$-$C_8)$alkylheterocyclyl,
- —$(C_2$-$C_8)$-alkenylheterocyclyl,
- —$R^9$,
- —$(C_1$-$C_8)$alkyl-$R^9$,
- —$(C_2$-$C_8)$alkenyl-$R^9$,
- —$(C_2$-$C_8)$alkynyl-$R^9$,
- —$CH_2$—S—$(C_1$-$C_{10})$-alkyl,
- —$CH_2$—S—$R^9$,
- —$CH_2$—$SO_2$—$R^9$,
- —$(CH_2)_n$—$R^9$,
- —$CH_2$—$SO_2$—$(C_1$-$C_{10})$-alkyl,
- —$(CH_2)_n$—CN
- —$(CH_2)_n$-Hal, in which Hal means F, Cl, or I
- —$CH_2$—O—$(C_1$-$C_{10})$-alkyl,
- —$(CH_2)_n$—$NR^7R^8$ in which $R^7$, $R^8$ have the meaning indicated above
- —$CH_2$—O—$R^9$, with the exception of —$CH_2$—$CH(CH_3)_2$, —CH=C$(CH_3)_2$ or

—$CH_2$—$C(CH_3)$=$CH_2$ in which $R^9$ means an aryl which may optionally be substituted with 1-3 alkyl, hydroxy, halogen, cyano or $C_1$-$C_5$-alkoxy-groups or a heteroaryl group in which the heteroarylgroup may contain 1-3 heteroatoms which may optionally be substituted with 1-3 alkyl, hydroxy, halogen, cyano or $C_1$-$C_5$-alkoxy-groups, n means an integer selected from 1, 2, 3, 4, 5.

Compounds of general formula I, in which at least one of $R^1$, $R^2$ or $R^3$ are different from hydrogen are a preferred embodiment of the invention. Furthermore, compounds of general formula I, in which $R^4$ is different from phenyl or naphthyl in unsubstituted form are another preferred embodiment of the invention.

A particular aspect of the invention are compounds of general formula I in which $R^1$ and $R^2$ are bound to adjacent ring carbon atoms and have together the meaning of —O—$(CH_2)_p$—O—, —O—$(CH_2)_p$—$CH_2$—, —O—CH=CH—, —$(CH_2)_{p+2}$—, —NH—$(CH_2)_{p+1}$—, —N($C_1$-$C_3$-alkyl)-$(CH_2)_{p+1}$—, or —NH—N=CH— (in which p=1 or 2) and thus form a condensed ring system.

The term "partially aromatic ring system", refers to bicyclic systems that contain an aromatic ring and a non-aromatic ring, such as, e.g., benzoxazinones or dihydroindolone.

Compounds of general formula I, in which $R^4$ means an optionally substituted phthalidyl, indolyl, isoindolyl, dihydroindolyl, dihydroisoindolyl, dihydroisoquinolinyl, dihydroquinolinyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, indolonyl, isoindolonyl, dihydroindolonyl, dihydroisoindolonyl, benzimidazole, coumarinyl, isocoumarinyl, pyrazolopyrimidinyl or indolyl group that is linked via any position. They are another object of the invention if these heterocyclic systems are substituted. They are another object of the invention if they are substituted with 1 to 3 of the same or different radicals from the group $C_1$-$C_3$-alkyl, hydroxy, carbonyl or halogen, especially if they are substituted with methyl, chlorine or fluorine.

Another object of the invention are compounds of general formula I wherein $R^4$ means phenyl, naphthyl, quinolin-5-yl, phthalazinyl, quinazolinyl which can be optionally substituted independently with 1-3 radicals selected from the group carbonyl, $C_1$-$C_3$-alkyl, chlorine or fluorine.

Preferably there is only one carbonyl group in $R^4$.

Another object of the invention are compounds of general formula I wherein $R^4$ means, quinolin-5-yl, phthalazinyl, quinazolinyl which can be optionally substituted independently with 1-3 radicals selected from the group carbonyl, $C_1$-$C_3$-alkyl, chlorine or fluorine.

Another object of the invention are compounds of general formula I wherein $R^4$ means phenyl, naphthyl, quinolin-5-yl, phthalazinyl, quinazolinyl which can be optionally substituted independently one or two times by carbonyl, methyl or fluorine.

Another object of the invention are compounds of general formula I wherein $R^4$ means quinolin-5-yl, phthalazinyl, quinazolinyl which can be substituted independently one or two times by carbonyl, methyl or.

Another object of the invention are compounds of general formula I wherein $R^4$ means phenyl, naphthyl, 2-methylquinolin-5-yl, quinolin-5-yl, 2-methyl-phthalazin-1-on-yl, 2-methyl-2H-phthalazin-1-on-yl, 7-Fluor-2-methyl-quinazoline.

Yet another object of the invention are compounds of general formula I wherein $R^4$ means 2-methylquinolin-5-yl, quinolin-5-yl, 2-methyl-phthalazin-1-on-yl, 2-methyl-2H-phthalazin-1-on-yl, 7-Fluor-2-methyl-quinazoline.

One group of compounds of general formula I is that in which $R^4$ is a heterocycle containing one or more nitrogen atoms, such as pyridine, pyrimidine, indolizine, indol or isoindol, pyrazole, imidazole, triazole, quinoline, isoquinoline, cinnoline, phthalazine, or quinazoline. Another group of compounds of general formula I is that in which $R^4$ is an oxygen containing heterocycle, such as coumaron (benzofurane) or chromane. A further group of compounds of general formula I is that in which $R^4$ is a heterocycle, containing two or more different heteroatoms, such as thiazole, isothiazole, oxazole or benzothiazole.

Compounds of formula I that for $R^4$ carry a coumarinyl or isocoumarinyl radical, in particular the isocoumarinyl radical, which optionally can be substituted with 0 to 3 of the same or different radicals from the group $C_1$-$C_3$-alkyl, hydroxy, carbonyl or halogen, in particular with methyl, chlorine or fluorine are a further object of the invention.

$R^4$ can be substituted in one or more positions with a radical selected from the group carbonyl, halogen, hydroxy, $(C_1$-$C_5)$-alkyl, $(C_1$-$C_5)$alkoxy, $(C_1$-$C_5)$-alkylthio, $(C_1$-$C_5)$-perfluoroalkyl, cyano, nitro, $NR^7R^8COOR^9(CO)NR^7R^8$ or a $(C_1$-$C_5$-alkylene)-O—(CO)—$(C_1$-$C_5)$alkyl group, preferably from the group $C_1$-$C_3$-alkyl, $C_1$-$C_3$-alkoxy, hydroxy, halogen, or carbonyl; preferably with methyl, chlorine or fluorine. The substituents can be the same or different.

The substituent carbonyl for a group $R^4$ is to be defined such that the carbonyl carbon atom is a ring carbon atom, to which an oxygen atom is double-bound.

Compounds of general formula I, in which radical $R^4$ is substituted with none, one or several of the same or different radicals from the group $C_1$-$C_3$-alkyl, $C_1$-$C_3$-alkoxy, hydroxy, halogen, or carbonyl, preferably with none or one or several of the same or different radicals from the group $C_1$-$C_3$-alkyl, hydroxy, carbonyl or halogen, in particular by one or more of the same or different radicals from the group methyl, chlorine or fluorine, especially by methyl, chlorine or fluorine, are an object of the invention.

Optionally the nitrogen atom of radical $R^4$ of general claim 1 (such as in the indazole, quinolone, isoquinolone and phthalazine) can also be alkylated with a $C_1$-$C_3$-alkyl group.

Compounds of general formula I, in which $R^4$ means a monocyclic 5- or 6-membered heterocyclic ring system that is linked via any position, such as, e.g., furan or thiophene, are another object of the invention.

Compounds of general formula I, in which $R^4$ means an substituted phenyl ring or an substituted naphthyl ring are another object of the invention.

As substituents for rings contained in $R^4$, the same that are already disclosed for $R^1$ and $R^2$ are suitable.

Compounds according to claim 1, in which $R^5$ means trifluoromethyl or pentafluoroethyl, are a special object of the invention.

Compounds of general formula I, in which the phenyl group is substituted with 1-3 of the same or different substituents, selected from the group carbonyl, $C_1$-$C_3$-alkoxy, hydroxy, and halogen, in particular carbonyl, methoxy, hydroxy, fluorine, chlorine, or bromine, and in which $R^4$ means a dihydroisoindolonyl, isoquinolonyl, quinazolinyl, indazolyl, coumarinyl, isocoumarinyl, which can be substituted with 0-2 substituents that are selected from the group carbonyl, $C_1$-$C_3$-alkyl and halogen, in particular methyl and fluorine, and $R^5$ means $CF_3$ or $C_2F_5$, in particular $CF_3$, are a preferred object of the invention.

Most preferred embodiments are those wherein:
I) at least one of $R^1$, $R^2$, $R^3$ is selected from methoxy, hydroxy, fluoro, chloro, methyl,
or $R^1$ and $R^2$ together mean a group —O—$CH_2$—O—, —$CH_2$—$CH_2$—O— or —$CH_2$—C($CH_3$)$_2$—O— (forming together with the phenyl group to which they are bound a five membered ring)
II) $R^4$ is selected from quinolin-5-yl, phthalazinyl, quinazolinyl which can be substituted independently one or two times by carbonyl, methyl or fluorine.
III) $R^5$ is —$CF_3$
IV) $R^6$ is selected from
benzyl, propyl, chloromethyl, bromomethyl, ethylsulfanylmethyl, (imidazol-2-yl)-sulfanylmethyl, (imidazol-2-yl)-sulfonylmethyl, 1,2,4-triazol-3-ylsulfanylmethyl, (1-methyl-imidazol-2-yl)-sulfanyl methyl, (1H-imidazol-2-yl)-sulfanylmethyl, pyrimidine-2-yl-sulfanylmethyl, 2-propylsulfanylmethyl, cyanomethyl, methylsulfanylmethyl, dimethylaminomethyl, ethoxymethyl-, hydroxymethyl, ethoxymethyl,
and all subcombinations of I-IV.

In addition, the invention relates to the use of the compounds of general formula I for the production of pharmaceutical agents as well as their use for the production of pharmaceutical agents for treating inflammatory diseases.

Unless otherwise notified the term "alkyl" refers to straight or branched derivatives. For example, the term propyl comprises $^n$-propyl and $^{iso}$-propyl, the term butyl comprises $^n$-butyl, $^{iso}$-butyl and $^{tert.}$-butyl.

The $C_1$-$C_5$-alkyl groups can be straight-chain or branched and stand for a methyl, ethyl, n-propyl, iso-propyl, n-butyl, iso-butyl, tert-butyl or n-pentyl group, or a 2,2-dimethylpropyl, 2-methylbutyl or 3-methylbutyl group. A methyl or ethyl group is preferred. They can optionally be substituted by 1-3 hydroxy, 1-3 $C_1$-$C_5$-alkoxy and/or 1-3 $COOR^6$ groups. Preferred are hydroxy groups.

The $C_1$-$C_5$-alkoxy groups in $R^1$, $R^2$, $R^3$ and $R^4$ can be straight-chain or branched and stand for a methoxy, ethoxy, n-propoxy, iso-propoxy, n-butoxy, iso-butoxy, tert-butoxy or n-pentoxy, 2,2-dimethylpropoxy, 2-methylbutoxy or 3-methylbutoxy group. A methoxy or ethoxy group is preferred.

The $C_1$-$C_5$-alkylthio groups can be straight-chain or branched and stand for a methylthio, ethylthio, n-propylthio, iso-propylthio, n-butylthio, iso-butylthio, tert-butylthio or n-pentylthio, 2,2-dimethylpropylthio, 2-methylbutylthio or 3-methylbutylthio group. A methylthio or ethylthio group is preferred.

For a partially or completely halogenated $C_1$-$C_{10}$-alkyl group, the following partially or completely halogenated groups are for example included:

fluoromethyl, difluoromethyl, trifluoromethyl, fluoroethyl, 1,1-difluoroethyl, 1,2-difluoroethyl, 1,1,1-trifluoroethyl, tetrafluoroethyl, and pentafluoroethyl, chloromethyl, dichloromethyl, trichloromethyl, chloroethyl, 1,1-dichloroethyl, 1,2-dichloroethyl, 1,1,1-trichloroethyl, 1,1,1-trichloropropyl, chloropropyl, bromomethyl, dibromomethyl, bromoethyl, 1,1-dibromoethyl, 1,2-dibromoethyl, bromopropyl, bromobutyl, and bromopentyl, iodomethyl, diiodomethyl, iodoethyl, 1,1-diiodoethyl, 1,2-diiodoethyl, iodopropyl, iodobutyl, and iodopentyl; Preferred embodiments are: fluoromethyl, trifluoromethyl, fluoroethyl, 1,1,1-trifluoroethyl, pentafluoroethyl, chloromethyl, chloroethyl, chloropropyl, bromomethyl, bromoethyl, bromopropyl.

For a partially or completely fluorinated $C_1$-$C_3$-alkyl group, the following partially or completely fluorinated groups can be considered: fluoromethyl, difluoromethyl, trifluoromethyl, fluoroethyl, 1,1-difluoroethyl, 1,2-difluoroethyl, 1,1,1-trifluoroethyl, tetrafluoroethyl, and pentafluoroethyl. Of the latter, the trifluoromethyl group or the pentafluoroethyl group is preferred.

The term halogen atom or halogen means a fluorine, chlorine, bromine or iodine atom. Preferred is a fluorine, chlorine or bromine atom.

The $NR^7R^8$ group includes, for example, $NH_2$, $N(H)CH_3$, $N(CH_3)_2$, $N(H)(CO)CH_3$, $N(CH_3)(CO)CH_3$, $N[(CO)CH_3]_2$, $N(H)CO_2CH_3$, $N(CH_3)CO_2CH_3$, or $N(CO_2CH_3)_2$.

Due to the presence of asymmetry centers the compounds of general formula I according to the invention may have several stereoisomers. Objects of this invention are all possible diastereomers, both as racemates and in enantiomer-pure form.

The compounds according to the invention can also be present in the form of salts with physiologically compatible anions, for example in the form of hydrochlorides, sulfates, nitrates, phosphates, pivalates, maleates, fumarates, tartrates, benzoates, mesylates, citrates or succinates.

The compounds can be produced by the various processes that are described below (a-d).

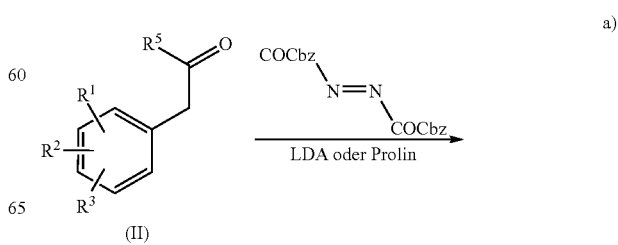

a)

In the formulae provided above COBbz has the meaning of Carboxybenzyl.

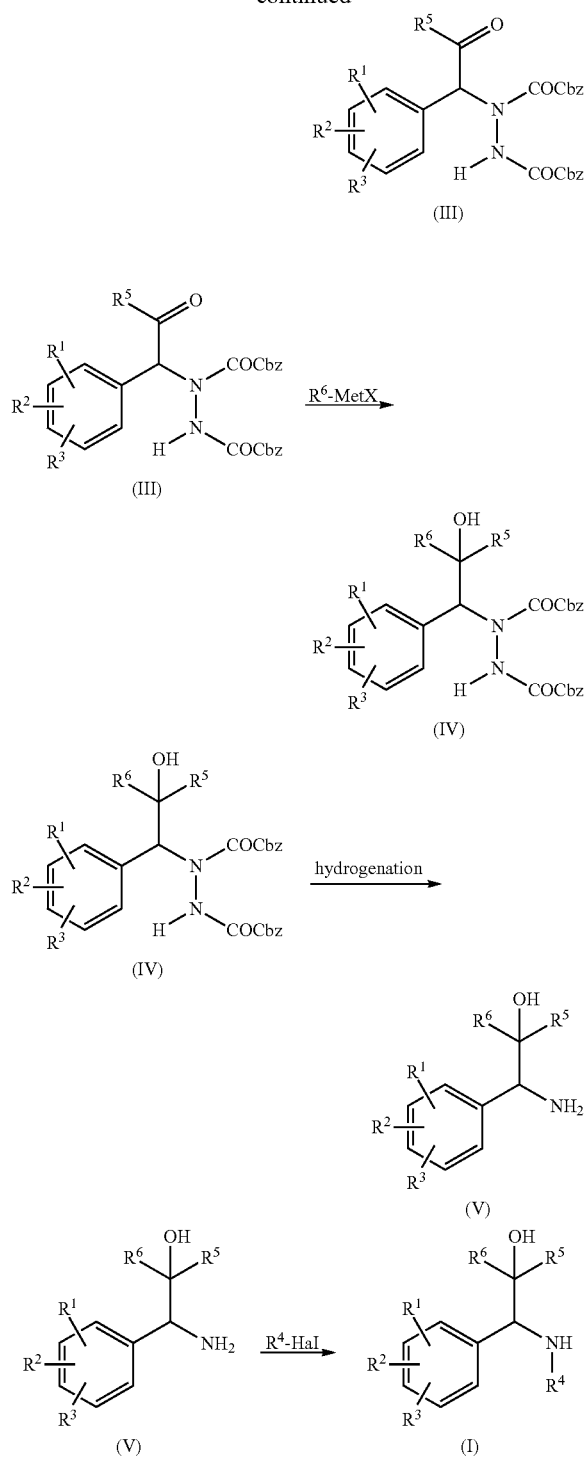

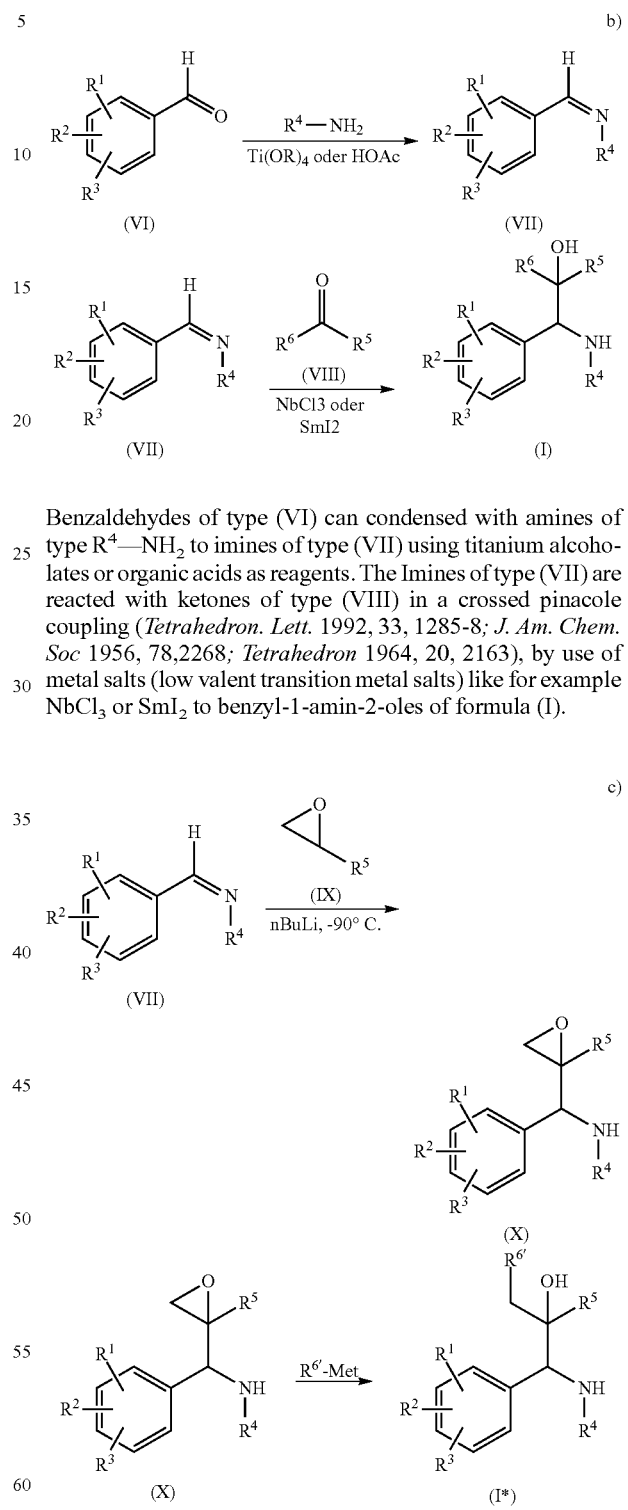

Benzaldehydes of type (VI) can condensed with amines of type $R^4$—$NH_2$ to imines of type (VII) using titanium alcoholates or organic acids as reagents. The Imines of type (VII) are reacted with ketones of type (VIII) in a crossed pinacole coupling (*Tetrahedron. Lett.* 1992, 33, 1285-8; *J. Am. Chem. Soc* 1956, 78,2268; *Tetrahedron* 1964, 20, 2163), by use of metal salts (low valent transition metal salts) like for example $NbCl_3$ or $SmI_2$ to benzyl-1-amin-2-oles of formula (I).

Ketone of the general formula (II) can be aminated under use of LDA or (L) or (D)-proline catalysis at the α-position with azadicarboxylates. The hydrazino ketone of formula (III) can be reacted with Grignard, organo-lithium reagents or organo-indium reagents of type $R^6$-Met to yield hydrazino alcohols of type (IV). Catalytic hydrogenation reduces the hydrazino carboxylate (IV) to amines of type (V) which can be substrates for aromatic amination with arylhalogens $R^4$Hal under copper or palladium catalysis.

In b) described imines of type (VII) are treated at low temperatures of −80° to −100° C. with the lithiated epoxide (IX) to yield compounds of type (X). The epoxides (X) can be opened by nucleophils of type $R^{6'}$-Met' to deliver compound (I*). Possible nucleophiles are alkylcuprates, vinylcuprates, thioles, allylsilanes, vinylsilanes, vinylstannanes, grignard compounds, in the presence of Lewis acids like $BF_3$ or $AlMe_3$, $AlCl_3$, cyanides, amines, alcoholes and thioalcoholes.

This process described above can be performed enantioselectively by use of enantio pure epoxides of formula (IX) to yield enantiopure compounds of formula (X) and (1*).

It is clear to a person skilled in the art, that by using this synthetic route only a subgroup of the group $R^6$ as defined in claim 1 can be synthesized. These compounds require a methylene group (—$CH_2$—) as the first element in the group $R^6$. The various possibilities that are possible are defined in the claims as —$CH_2$—$R^{6'}$.

d)
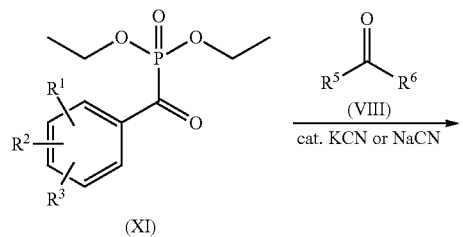
(XI) (VIII) cat. KCN or NaCN

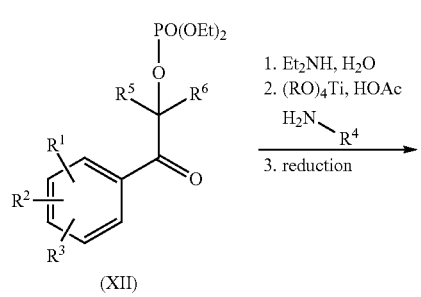
(XII)

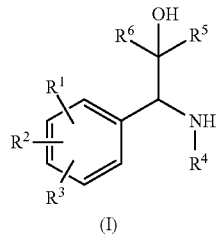
1. $Et_2NH$, $H_2O$
2. $(RO)_4Ti$, HOAc
   $H_2N\text{—}R^4$
3. reduction (I)

The α-ketophosphonate (XI) is condensed under cyanide catalysis to α-keto-phosphoric acid ester (XII). The α-ketophosphoric acid ester (XII) is cleaved to the α-hydroxyketone and condensed to an imine under presence of titanates and acetic acid. Reduction of the imine by sodiumborohydrate or catalytic hydrogenation delivers compound (I).

A further object of the invention are compounds of general formulae V, VII, X and XII

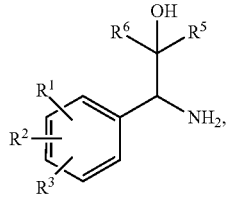
(V)

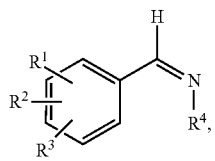
(VII)

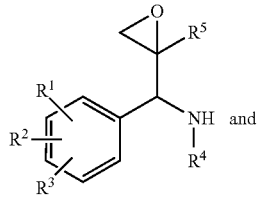
(X)
and

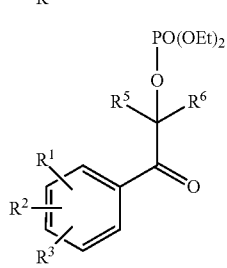
(XII)

in which $R^1$, $R^2$, $R^3$, $R^4$, $R^5$ and $R^6$ have the meanings described above and their use for the manufacture of compounds of general formula I.

The substituents $R^1$, $R^2$, $R^3$, $R^4$, $R^5$ and $R^6$ of compounds of general formulae V, VII, X and XII have generally the same meaning as described above as substituents of general formula I. It has to be understood that not all of $R^1$, $R^2$, $R^3$, $R^4$, $R^5$ and $R^6$ are present in each of formula V, VII, X and XII. Formula XII for example does not contain $R^4$, formula V for example does neither contain $R^5$ nor $R^6$. The definitions provided in the explanation of formula I have to be understood that only some substituents from the group $R^1$, $R^2$, $R^3$, $R^4$, $R^5$ and $R^6$ realized are present in the compounds of general formulae V, VII, X and XII.

Compounds of general formula VII or X, in which $R^4$ means an optionally substituted phthalidyl, indolyl, isoindolyl, dihydroindolyl, dihydroisoindolyl, dihydroisoquinolinyl, dihydroquinolinyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, indolonyl, isoindolonyl, dihydroindolonyl, dihydroisoindolonyl, benzimidazole, coumarinyl, isocoumarinyl, pyrazolopyrimidinyl or indolyl group that is linked via any position. They are another object of the invention if these heterocyclic systems are substituted. They are another object of the invention if they are substituted with 1 to 3 of the same or different radicals from the group $C_1$-$C_3$-alkyl, hydroxy, carbonyl or halogen, especially if they are substituted with methyl, chlorine or fluorine.

Another object of the invention are compounds of general formula VII or X wherein $R^4$ means phenyl, naphthyl, quinolin-5-yl, phthalazinyl, quinazolinyl which can be optionally substituted independently with 1-3 radicals selected from the group carbonyl, $C_1$-$C_3$-alkyl, chlorine or fluorine. Preferably there is only one carbonyl group in $R^4$.

Another object of the invention are compounds of general formula VII or X wherein $R^4$ means, quinolin-5-yl, phthalazinyl, quinazolinyl which can be optionally substituted independently with 1-3 radicals selected from the group carbonyl, $C_1$-$C_3$-alkyl, chlorine or fluorine.

Another object of the invention are compounds of general formula VII or X wherein $R^4$ means phenyl, naphthyl, quinolin-5-yl, phthalazinyl, quinazolinyl which can be optionally substituted independently one or two times by carbonyl, methyl or fluorine.

Another object of the invention are compounds of general formula VII or X wherein $R^4$ means quinolin-5-yl, phthalazinyl, quinazolinyl which can be substituted independently one or two times by carbonyl, methyl or fluorine.

Another object of the invention are compounds of general formula VII or X wherein $R^4$ means phenyl, naphthyl, 2-methylquinolin-5-yl, quinolin-5-yl, 2-methyl-phthalazin-1-on-yl, 2-methyl-2H-phthalazin-1-on-yl, 7-Fluor-2-methyl-quinazoline.

Yet another object of the invention are compounds of general formula VII or X wherein $R^4$ means 2-methylquinolin-5-yl, quinolin-5-yl, 2-methyl-phthalazin-1-on-yl, 2-methyl-2H-phthalazin-1-on-yl, 7-Fluor-2-methyl-quinazoline.

One group of compounds of general formula I is that in which $R^4$ is a heterocycle containing one or more nitrogen atoms, such as pyridine, pyrimidine, indolizine, indol or isoindol, pyrazole, imidazole, triazole, quinoline, isoquinoline, cinnoline, phthalazine, or quinazoline. Another group of compounds of general formula VII or X is that in which $R^4$ is an oxygen containing heterocycle, such as coumaron (benzofurane) or chromane. A further group of compounds of general formula VII or X is that in which $R^4$ is a heterocycle, containing two or more different heteroatoms, such as thiazole, isothiazole, oxazole or benzothiazole.

Compounds of formula VII or X that for $R^4$ carry a coumarinyl or isocoumarinyl radical, in particular the isocoumarinyl radical, which optionally can be substituted with 0 to 3 of the same or different radicals from the group $C_1$-$C_3$-alkyl, hydroxy, carbonyl or halogen, in particular with methyl, chlorine or fluorine are a further object of the invention.

$R^4$ in the compounds of general formula VII or X can be substituted in one or more positions with a radical selected from the group carbonyl, halogen, hydroxy, ($C_1$-$C_5$)-alkyl, ($C_1$-$C_5$)alkoxy, ($C_1$-$C_5$)-alkylthio, ($C_1$-$C_5$)-perfluoroalkyl, cyano, nitro, $NR^7R^8COOR^9(CO)NR^7R^8$ or a ($C_1$-$C_5$-alkylene)-O—(CO)—($C_1$-$C_5$)alkyl group, preferably from the group $C_1$-$C_3$-alkyl, $C_1$-$C_3$-alkoxy, hydroxy, halogen, or carbonyl; preferably with methyl, chlorine or fluorine. The substituents can be the same or different.

The substituent carbonyl for a group $R^4$ in compounds of formula VII or X is to be defined such that the carbonyl carbon atom is a ring carbon atom, to which an oxygen atom is double-bound.

Compounds of general formula VII or X, in which radical $R^4$ is substituted with none, one or several of the same or different radicals from the group $C_1$-$C_3$-alkyl, $C_1$-$C_3$-alkoxy, hydroxy, halogen, or carbonyl, preferably with none or one or several of the same or different radicals from the group $C_1$-$C_3$-alkyl, hydroxy, carbonyl or halogen, in particular by one or more of the same or different radicals from the group methyl, chlorine or fluorine, especially by methyl, chlorine or fluorine, are an object of the invention.

Optionally the nitrogen atom of radical $R^4$ of general claim formula VII or X (such as in the indazole, quinolone, isoquinolone and phthalazine) can also be alkylated with a $C_1$-$C_3$-alkyl group.

Compounds of general formula VII or X, in which $R^4$ means a monocyclic 5- or 6-membered heterocyclic ring system that is linked via any position, such as, e.g., furan or thiophene, are another object of the invention.

Compounds of general formula VII or X, in which $R^4$ means an substituted phenyl ring or an substituted naphthyl ring are another object of the invention.

As substituents for rings contained in $R^4$, the same that are already disclosed for $R^1$ and $R^2$ are suitable.

Especially preferred are compounds of general formulae V, VII, X and XII in which
I) at least one of $R^1$, $R^2$, $R^3$ is selected from
methoxy, hydroxy, fluoro, chloro, methyl,
or $R^1$ and $R^2$ together mean a group —O—$CH_2$—O—, —$CH_2$—$CH_2$—O— or —$CH_2$—C($CH_3$)$_2$—O— (forming together with the phenyl group to which they are bound a five membered ring)
II) $R^4$ is selected from quinolin-5-yl, phthalazinyl, quinazolinyl which can be substituted independently one or two times by carbonyl, methyl or fluorine
III) $R^5$ is —$CF_3$
IV) $R^6$ is selected from
benzyl, propyl, chloromethyl, bromomethyl, ethylsulfanylmethyl, (imidazol-2-yl)-sulfanylmethyl, (imidazol-2-yl)-sulfonylmethyl, 1,2,4-triazol-3-ylsulfanylmethyl, (1-methyl-imidazol-2-yl)-sulfanylmethyl, (1H-imidazol-2-yl)-sulfanylmethyl, pyrimidine-2-yl-sulfanylmethyl, 2-propylsulfanylmethyl, cyanomethyl, methylsulfanylmethyl, dimethylaminomethyl, ethoxymethyl-, hydroxymethyl, ethoxymethyl
and all subcombinations of I-IV.

If the various compounds according to the invention are present as racemic mixtures, they can be separated into pure, optically active forms according to the methods of racemate separation that are familiar to one skilled in the art. For example, the racemic mixtures can be separated by chromatography on an even optically active carrier material (CHIRALPAK AD®) into the pure isomers. It is also possible to esterify the free hydroxy group in a racemic compound of general formula I with an optically active acid and to separate the diastereoisomeric esters that are obtained by fractionated crystallization or by chromatography, and to saponify the separated esters in each case to the optically pure isomers. As an optically active acid, for example, mandelic acid, camphorsulfonic acid or tartaric acid can be used.

The binding of the substances to the glucocorticoid receptor (GR) and other steroid hormone receptors (mineral corticoid receptor (MR), progesterone receptor (PR) and androgen receptor (AR)) is examined with the aid of recombinantly produced receptors. Cytosol preparations of Sf9 cells, which had been infected with recombinant baculoviruses, which code for the GR, are used for the binding studies. In comparison to reference substance [$^3$H]-dexamethasone, the substances show a high to very high affinity to GR. $IC_{50}$(GR)=64 nM was thus measured for the compound from Example 3.

As an molecular mechanism for the anti-inflammatory action of glucocorticoids, the GR-mediated inhibition of the transcription of cytokines, adhesion molecules, enzymes and other pro-inflammatory factors is considered. This inhibition is produced by an interaction of the GR with other transcription factors, e.g., AP-1 and NF-kappa-B (for a survey, see Cato, A. C. B., and Wade, E., BioEssays 18, 371-378, 1996).

The compounds of general formula I according to the invention inhibit the secretion of cytokine IL-8 into the human monocyte cell line THP-1 that is triggered by lipopolysaccharide (LPS). The concentration of the cytokines was determined in the supernatant by means of commercially available ELISA kits. The compound from Example 3 showed an inhibition $IC_{50}(IL8)=25$ nmol.

The anti-inflammatory action of the compounds of general formula I was tested in the animal experiment by tests in the croton oil-induced inflammation in rats and mice (J. Exp. Med. (1995), 182, 99-108). To this end, croton oil in ethanolic solution was applied topically to the animals' ears. The test substances were also applied topically or systemically at the same time or two hours before the croton oil. After 16-24 hours, the ear weight was measured as a yardstick for inflammatory edema, the peroxidase activity as a yardstick for the invasions of granulocytes, and the elastase activity as a yardstick for the invasion of neutrophilic granulocytes. In this test, the compounds of general formula I inhibit the three abovementioned inflammation parameters both after topical administration and after systemic administration.

One of the most frequent undesirable actions of a glucocorticoid therapy is the so-called "steroid diabetes" [cf., Hatz, H. J., Glucocorticoide: Immunologische Grundlagen, Pharmakologie and Therapierichtlinien [Glucocorticoids: Immunological Bases, Pharmacology and Therapy Guidelines], Wissenschaftliche Verlagsgesellschaft mbH, Stuttgart, 1998]. The reason for this is the stimulation of gluconeogenesis in the liver by induction of the enzymes responsible in this respect and by free amino acids, which are produced from the degradation of proteins (catabolic action of glucocorticoids). A key enzyme of the catabolic metabolism in the liver is tyrosinamino transferase (TAT). The activity of this enzyme can be determined from liver homogenates by photometry and represents a good measurement of the undesirable metabolic actions of glucocorticoids. To measure the TAT induction, the animals are sacrificed 8 hours after the test substances are administered, the livers are removed, and the TAT activity is measured in the homogenate. In this test, at doses in which they have an anti-inflammatory action, the compounds of general formula I induce little or no tyrosinamino transferase.

Because of their anti-inflammatory and, in addition, antiallergic, immunosuppressive and antiproliferative action, the compounds of general formula I according to the invention can be used as medications for treatment or prophylaxis of the following pathologic conditions in mammals and humans: In this case, the term "DISEASE" stands for the following indications:

(i) Lung diseases that are accompanied by inflammatory, allergic and/or proliferative processes:
    Chronic, obstructive lung diseases of any origin, primarily bronchial asthma
    Bronchitis of different origins
    All forms of restrictive lung diseases, primarily allergic alveolitis,
    All forms of pulmonary edema, primarily toxic pulmonary edema
    Sarcoidoses and granulomatoses, especially Boeck's disease (ii) Rheumatic diseases/autoimmune diseases/joint diseases that are accompanied by inflammatory, allergic and/or proliferative processes:
    All forms of rheumatic diseases, especially rheumatoid arthritis, acute rheumatic fever, polymyalgia rheumatica
    Reactive arthritis
    Inflammatory soft-tissue diseases of other origins
    Arthritic symptoms in the case of degenerative joint diseases (arthroses)
    Traumatic arthritides
    Collagenoses of any origin, e.g., systemic lupus erythematodes, sclerodermia, polymyositis, dermatomyositis, Sjögren's syndrome, Still's syndrome, Felty's syndrome (iii) Allergies that are accompanied by inflammatory and/or proliferative processes:
    All forms of allergic reactions, e.g., Quincke's edema, hay fever, insect bites, allergic reactions to pharmaceutical agents, blood derivatives, contrast media, etc., anaphylactic shock, urticaria, contact dermatitis (iv) Vascular inflammations (vasculitides)
    Panarteritis nodosa, temporal arteritis, erythema nodosum (v) Dermatological diseases that are accompanied by inflammatory, allergic and/or proliferative processes:
    Atopic dermatitis (primarily in children)
    Psoriasis
    Pityriasis rubra pilaris
    Erythematous diseases, triggered by different noxae, e.g., radiation, chemicals, burns, etc.
    Bullous dermatoses
    Diseases of the lichenoid group,
    Pruritis (e.g., of allergic origin)
    Seborrheal eczema
    Rosacea
    Pemphigus vulgaris
    Erythema exudativum multiforme
    Balanitis
    Vulvitis
    Hair loss such as alopecia areata
    Cutaneous T-cell lymphoma (vi) Kidney diseases that are accompanied by inflammatory, allergic and/or proliferative processes:
    Nephrotic syndrome
    All nephritides (vii) Liver diseases that are accompanied by inflammatory, allergic and/or proliferative processes:
    Acute liver cell decomposition
    Acute hepatitis of different origins, e.g., viral, toxic, pharmaceutical agent-induced
    Chronic aggressive hepatitis and/or chronic intermittent hepatitis (viii) Gastrointestinal diseases that are accompanied by inflammatory, allergic and/or proliferative processes:
    Regional enteritis (Crohn's disease)
    Colitis ulcerosa
    Gastritis
    Reflux esophagitis
    Ulcerative colitis of other origins, e.g., native sprue (ix) Proctologic diseases that are accompanied by inflammatory, allergic and/or proliferative processes:
    Anal eczema
    Fissures
    Hemorrhoids
    Idiopathic proctitis (x) Eye diseases that are accompanied by inflammatory, allergic and/or proliferative processes:
    Allergic keratitis, uveitis, iritis
    Conjunctivitis
    Blepharitis
    Optic neuritis
    Chorioiditis
    Sympathetic ophthalmia (xi) Diseases of the ear-nose-throat area that are accompanied by inflammatory, allergic and/or proliferative processes:
  Allergic rhinitis, hay fever
  Otitis externa, e.g., caused by contact dermatitis, infection, etc.
  Otitis media
(xii) Neurological diseases that are accompanied by inflammatory, allergic and/or proliferative processes:
  Cerebral edema, primarily tumor-induced cerebral edema
  Multiple sclerosis
  Acute encephalomyelitis
  Meningitis
  Various forms of convulsions, e.g., infantile nodding spasms
(xiii) Blood diseases that are accompanied by inflammatory, allergic and/or proliferative processes:
  Acquired hemolytic anemia
  Idiopathic thrombocytopenia
(xiv) Tumor diseases that are accompanied by inflammatory, allergic and/or proliferative processes:
  Acute lymphatic leukemia
  Malignant lymphoma
  Lymphogranulomatoses
  Lymphosarcoma
  Extensive metastases, mainly in breast, bronchial and prostate cancers
(xv) Endocrine diseases that are accompanied by inflammatory, allergic and/or proliferative processes:
  Endocrine orbitopathy
  Thyreotoxic crisis
  De Quervain's thyroiditis
  Hashimoto's thyroiditis
  Basedow's disease
(xvi) Organ and tissue transplants, graft-versus-host disease
(xvii) Severe shock conditions, e.g., anaphylactic shock, systemic inflammatory response syndrome (SIRS)
(xviii) Substitution therapy in:
  Innate primary suprarenal insufficiency, e.g., congenital adrenogenital syndrome
  Acquired primary suprarenal insufficiency, e.g., Addison's disease, autoimmune adrenalitis, meta-infective tumors, metastases, etc.
  Innate secondary suprarenal insufficiency, e.g., congenital hypopituitarism
  Acquired secondary suprarenal insufficiency, e.g., meta-infective tumors, etc.
(xix) Vomiting that is accompanied by inflammatory, allergic and/or proliferative processes:
  e.g., in combination with a 5-HT3 antagonist in cytostatic-agent-induced vomiting
(xx) Pains of inflammatory origins, e.g., lumbago.

Moreover, the compounds of general formula I according to the invention can be used for treatment and prophylaxis of additional pathologic conditions that are not mentioned above, for which synthetic glucocorticoids are now used (see in this respect Hatz, H. J., Glucocorticoide: Immunologische Grundlagen, Pharmakologie und Therapierichtlinien, Wissenschaftliche Verlagsgesellschaft mbH, Stuttgart, 1998).

All previously mentioned indications (i) to (xx) are described in more detail in Hatz, H. J., Glucocorticoide: Immunologische Grundlagen, Pharmakologie und Therapierichtlinien, Wissenschaftliche Verlagsgesellschaft mbH, Stuttgart, 1998.

For the therapeutic actions in the above-mentioned pathologic conditions, the suitable dose varies and depends on, for example, the active strength of the compound of general formula I, the host, the type of administration, and the type and severity of the conditions that are to be treated, as well as the use as a prophylactic agent or therapeutic agent.

In addition, the invention provides:
(i) The use of one of the compounds of formula I according to the invention or mixture thereof for the production of a medication for treating a DISEASE;
(ii) A process for treating a DISEASE, said process comprises an administration of an amount of the compound according to the invention, in which the amount suppresses the disease and in which the amount of compound is given to a patient who requires such a medication;
(iii) A pharmaceutical composition for treating a DISEASE, said treatment comprises one of the compounds according to the invention or mixture thereof and at least one pharmaceutical adjuvant and/or vehicle.

In general, satisfactory results can be expected in animals when the daily doses comprise a range of 1 µg to 100,000 µg of the compound according to the invention per kg of body weight. In the case of larger mammals, for example the human, a recommended daily dose lies in the range of 1 µg to 100,000 µg per kg of body weight. Preferred is a dose of 10 to 30,000 µg per kg of body weight, and more preferred is a dose of 10 to 10,000 µg per kg of body weight. For example, this dose is suitably administered several times daily. For treating acute shock (e.g., anaphylactic shock), individual doses can be given that are significantly above the above-mentioned doses.

The formulation of the pharmaceutical preparations based on the new compounds is carried out in a way that is known in the art by the active ingredient being processed with the vehicles that are commonly used in galenicals, fillers, substances that influence decomposition, binding agents, moisturizers, lubricants, absorbents, diluents, flavoring correctives, coloring agents, etc., and converted into the desired form of administration. In this case, reference is made to Remington's Pharmaceutical Science, $15^{th}$ Edition, Mack Publishing Company, East Pennsylvania (1980).

For oral administration, especially tablets, coated tablets, capsules, pills, powders, granulates, lozenges, suspensions, emulsions or solutions are suitable.

For parenteral administration, injection and infusion preparations are possible.

For intra-articular injection, correspondingly prepared crystal suspensions can be used.

For intramuscular injection, aqueous and oily injection solutions or suspensions and corresponding depot preparations can be used.

For rectal administration, the new compounds can be used in the form of suppositories, capsules, solutions (e.g., in the form of enemas) and ointments both for systemic and for local treatment.

For pulmonary administration of the new compounds, the latter can be used in the form of aerosols and inhalants.

For local application to eyes, outer ear channels, middle ears, nasal cavities, and paranasal sinuses, the new compounds can be used as drops, ointments and tinctures in corresponding pharmaceutical preparations.

For topical application, formulations in gels, ointments, fatty ointments, creams, pastes, powders, milk and tinctures are possible. The dosage of the compounds of general formula I should be 0.01%-20% in these preparations to achieve a sufficient pharmacological action.

The invention also comprises the compounds of general formula I according to the invention as therapeutic active ingredients.

In addition, the compounds of general formula I according to the invention are part of the invention as therapeutic active ingredients together with pharmaceutically compatible and acceptable adjuvants and vehicles.

The invention also comprises a pharmaceutical composition that contains one of the pharmaceutically active compounds according to the invention or mixtures thereof or a pharmaceutically compatible salt thereof and a pharmaceutically compatible salt or pharmaceutically compatible adjuvants and vehicles.

The compounds of general formula (I) according to the invention can optionally also be formulated and/or administered in combination with other active ingredients.

The invention therefore also relates to combination therapies or combined compositions, in which a compound of general formula (I) or a pharmaceutically acceptable salt thereof, or a pharmaceutical composition that contains a compound of general formula (I) or a pharmaceutically acceptable salt thereof, is administered either simultaneously (optionally in the same composition) or in succession together with one or more pharmaceutical agents for treating one of the above-mentioned pathologic conditions. For example, for treatment of rheumatoid arthritis, osteoarthritis, COPD (chronic obstructive lung disease), asthma or allergic rhinitis, a compound of general formula (I) of this invention can be combined with one or more pharmaceutical agents for treating such a condition. When such a combination is administered by inhalation, the pharmaceutical agent that is to be combined can be selected from the following list:

A PDE4 inhibitor including an inhibitor of the PDE4D isoform,

A selective β.sub2.adrenoceptor agonist, such as, for example, metaproterenol, isoproterenol, isoprenaline, albuterol, salbutamol, formoterol, salmeterol, terbutaline, orcipresnaline, bitolterol mesylate, pirbuterol or indacaterol;

A muscarine receptor antagonist (for example, an M1, M2 or M3 antagonist, such as, for example, a more selective M3 antagonist), such as, for example, ipratropium bromide, tiotropium bromide, oxitropium bromide, pirenzepine or telenzepine;

A modulator of the chemokine receptor function (such as, for example, a CCR1 receptor antagonist); or An inhibitor of the p38 kinase function.

For another object of this invention, such a combination with a compound of general formula (I) or a pharmaceutically acceptable salt thereof is used for treatment of COPD, asthma or allergic rhinitis and can be administered by inhalation or orally in combination with xanthine (such as, for example, aminophylline or thyeophylline), which also can be administered by inhalation or orally.

EXPERIMENTAL PART

The various aspects of the invention described in this application are illustrated by the following examples which are not meant to limit the invention in any way.

Example 1

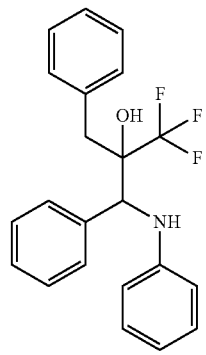

α-Benzyl-β-[(phenyl)amino)-α-(trifluoromethyl) benzeneethanol

N-{Phenyl[2-(trifluoromethyl)oxiranyl] methyl}anilin 0.63 ml (7.4 mmol) 1,1,1-trifluoroepoxypropane in 35 ml THF and are cooled to −104° C. and 5.1 ml of a 1.6 M n-butyl lithium solution in hexane are added over 3 hours while the temperature does not exceed −99° C. 10 Minutes after complete addition 2.0 g (11 mmol) N-benzylideneanilin in 10 ml THF are added over 0.5 hours while the temperature does not exceed −99° C. After 10 minutes at −100° C. 7.4 ml diethyl ether are added and the reaction mixture is warmed to 20° C. over one hour. The reaction is quenched by addition of saturated ammonium chloride solution. The phases are separated and the aqueous layer is extracted twice with diethyl ether, the combined organic phases washed with brine, dried over sodium sulphate and then evaporated. Flash chromatography on silica gel (aceton in hexane 30 to 40%) yields 1.8 g of the desired epoxide.

$^1$H-NMR (CDCl$_3$); δ=2.58 (m, 1H), 3.06 (d, 1H), 3.77 (s, 3H), 4.42 (d, 1H), 5.06 (d, 1H), 6.56 (d, 2H), 6.71 (t, 1H), 7.09-7.56 (m, 5H), 7.89 (d, 2H).

To 0.49 g (3.9 mmol) aluminium chloride in 3 ml benzene at 5° C. are added 0.9 mg (3.1 mmol) N-{Phenyl[2-(trifluoromethy)loxiranyl]methyl}aniline in 3 ml benzene. The reaction mixture is stirred for 2 hours at 25° C. and then poured into a saturated sodium hydrogen carbonate solution and ice. The mixture is vigorously stirred, phases are separated the aqueous layer is extracted twice with ethyl acetate. The combined organic phases are washed with brine, died over sodium sulphate and evaporated. Flash chromatography on silica gel (ethyl acetate in hexane 25%) yields 250 mg of the desired product as a single diastereomer.

$^1$H-NMR (CD$_3$OD); δ=3.59 (d, 1H), 3.76 (d, 1H), 4.77 (br, 1H), 4.96 (s, 1H), 6.65 (d, 2H), 6.75 (t, 1H), 7.10-7.20 (m, 4H), 7.30-7.42 (m, 6H), 7.46 (d, 2H).

Example 2

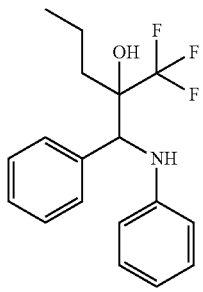

α-Propyl-β-[(phenyl)amino]-α-(trifluoromethyl) benzeneethanol

To 175 mg (0.92 mmol) copper(I) iodide in 4 ml THF at −30° C. are added 4 ml of a 3M ethyl magnesium bromid in diethyl ether. After 30 minutes at −30° C. 0.9 g (3.1 mmol) N-{Phenyl [2-(trifluoromethy)loxiranyl]methyl}anilin in 3 ml THF are added. The reaction mixture is stirred for 4 hours at −30° C. and then poured into a saturated ammonium chloride solution. Phases are separated and the aqueous layer is extracted twice with ethyl acetate. The combined organic phases are washed with brine, died over sodium sulphate and evaporated. Flash chromatography on silica gel (ethyl acetate in hexane 5% to 30%) yields 335 mg of the desired product as a single diastereomer.

$^1$H-NMR (CD$_3$OD); δ=0.86 (t, 3H), 1.44-1.53 (m, 3H), 1.70 (ddd, 1H), 4.65 (d, 1H), 4.72 (d, 1K), 6.58 (d, 2H), 6.68 (t, 1H), 7.07 (d, 2H), 7.26-7.57 (m, 5H).

Example 3

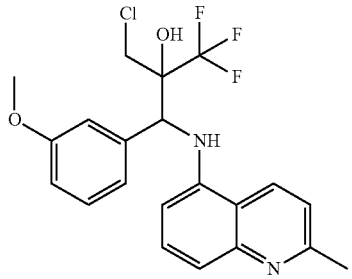

α-Chloromethyl-2-methoxy-β-[(2-methylquinolin-5-yl)amino]-α-(trifluoromethyl)benzeneethanol {[3-Methoxyphenyl][2-(trifluoromethy)loxiranyl] methyl}-2-methylquinolin-5-amine To 1.17 g (7.4 mmol) 5-amino-2-methylquinolin and 1 g (7.4 mmol) 3-methoxybenzaldehyde in 39 ml toluene are added 1 ml acetic acid. The mixture is heated over 3 hours under reflux while water is trapped in a Dean Stark apparatus. The solvent is evaporated and the residue is two times azeotrophed with small portions of toluene. 2.1 g of [(3-methoxyphenyl)methylene]-2-methylquinolin-5-amine are obtained as product. 0.31 ml (3.6 mmol) 1,1,1-trifluoroepoxypropane in 17 ml THF and are cooled to −104° C. and 1.59 ml of a 2.5 M n-butyl lithium solution in hexane are added over 3 hours while the temperature does not exceed −99° C. 10 Minutes after complete addition 1.5 g (5.4 mmol) [(3-methoxyphenyl)methylene]-2-methylquinolin-5-amine in 5 ml THF are added over 0.5 hours while the temperature temperature does not exceed −99° C. After 0.5 hours at −100° C. 4 ml diethyl ether are added and the reaction mixture is warmed to 20° C. over one hour. The reaction was quenched by addition of saturated ammonium chloride solution. The phases were separated and the aqueous layer was extracted twice with diethyl ether, the combined organic phases washed with brine, dried over sodium sulphate and then evaporated. Flash chromatography on silica gel (aceton in hexane 30 to 40%) yields 800 mg of the desired epoxide.

$^1$H-NMR (CDCl$_3$); δ=2.64 (m, 1H), 2.72 (s, 3H), 3.13 (d, 1H), 3.77 (s, 3H), 5.14 (d, 1H), 5.20 (d, 1H), 6.38 (d, 1H), 6.84 (d, 1H), 6.90 (s, 1H), 6.95 (d, 1H), 7.26-7.29 (m, 2H), 7.35 (t, 1H), 7.41 (d, 1H), 8.19 (d, 1H).

To 128 mg (0.96 mmol) aluminium chloride in 4 ml benzene at 5° C. are added 310 mg (0.8 mmol) {[3-methoxyphenyl] [2-(trifluoromethyl)oxiranyl]methyl}-2-methylquinolin-5-amine in 2 ml benzene. The reaction mixture is stirred for 3 at 25° C. and then poured into a saturated sodium hydrogen carbonate solution. The mixture is vigorously stirred, phases are separated the aqueous layer is extracted twice with ethyl acetate. The combined organic phases are washed with brine, died over sodium sulphate and evaporated. Flash chromatography on silica gel (acetone in hexane 0% to 35%) yields 140 mg of the desired product as a single diastereomer.

$^1$H-NMR (CD$_3$OD); δ=2.65 (s, 3H), 3.13 (dq, 1H), 3.68 (d, 1H), 3.73 (s, 3H), 5.12 (s, 1H), 6.49 (d, 1H), 6.85 (d, 1H), 7.18-7.24 (m, 4H), 7.35 (d, 1H), 7.36 (t, 1H), 8.42 (d, 1H).

Example 4

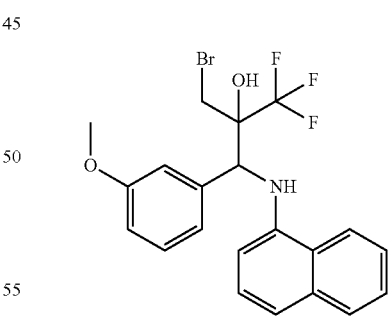

α-Bromomethyl-3-methoxy-β-[(naphth-1-yl)amino]-α-(trifluoromethyl)benzeneethanol {(3-Methoxyphenyl)[2-(trifluoromethyl)oxiranyl] methyl}naphthalene-1-amine Analogously to Example 3, the corresponding imine is produced starting from 5.0 g (34.9 mmol) 1-aminonaphthalene and 4.24 ml (34.9 mmol) 3-methoxybenzaldehyde in toluene.

To 2.11 g (8.1 mmol) [(3-methoxyphenyl)methylene]naphthalene-1-amine in THF are added 0.63 ml (7.4 mmol) of the lithiated 1,1,1-trifluoroepoxypropane at −100° C. analogously to example 3. Typical work up and chromatographic purification on silica gel (ethyl acetate in hexane 5%) yield 1.29 g {[3-methoxyphenyl][2-(trifluoromethyl)oxiranyl]methyl}naphthalene-5-amine as yellow oil.

1H-NMR (CDCl3); δ=2.68 (m, 1H), 3.14 (d, 1H), 3.77 (s, 3H), 5.22 (s, 2H), 6.40 (d, 1H), 6.84 (d, 1H), 6.94 (s, 1H), 6.99 (d, 1H), 7.16-7.28 (m, 3H), 7.50 (m, 2H), 7.79 (d, 1H), 7.95 (d, 1H).

To 30 mg (0.16 mmol) copper(I) iodide in 2 ml THF at −30° C. are added 0.71 ml of a 3-Methyl magnesium bromid in diethyl ether. After 30 minutes at −30° C. 200 mg (0.54 mmol) {[3-methoxyphenyl][2-(trifluoromethyl)oxiranyl]methyl}naphthalene-5-amine in 0.5 ml THF are added. The reaction mixture is stirred for 2 hours at 0° C., 14 hours at 25° C. and then poured into a saturated ammonium chloride solution. Phases are separated and the aqueous layer is extracted twice with ethyl acetate. The combined organic phases are washed with brine, died over sodium sulphate and evaporated. Flash chromatography on silica gel (ethyl acetate in hexane 5%) yields 50 mg of the title compound and 4 mg α-chloromethyl-3-methoxy-β-[(naphth-1-yl)amino]-β-(trifluoromethyl)benzeneethanol (example 6).

$^1$H-NMR (CDCl3); δ=3.57 (d, 1H), 3.77 (d, 1H), 3.78 (s, 3H), 5.15 (s, 1H), 5.55 (br, 1H), 6.52 (d, 1H), 6.86 (d, 1H), 7.11 (s, 1H), 7.14 (m, 2H), 7.28 (m, 2H), 7.50 (m, 2H), 7.79 (d, 1H), 7.98 (d, 1H).

Example 5

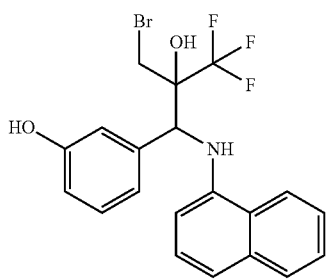

α-Bromomethyl-3-hydroxy-β-[(naphth-1-yl)amino]-α-(trifluoromethyl)benzeneethanol To 20 mg (0.04 mmol) of α-Bromomethyl-3-methoxy-β-[(naphth-1-yl)amino]-α-(trifluoromethyl)benzeneethanol in 2 ml dichloromethane at −20° C. are added 0.44 ml of a 1 M solution of boron tribromide in dichloromethane under argon. The reaction mixture is stirred for 16 hours in a temperature range of between 0° C. and 25° C. The reaction mixture is mixed at 0° C. with saturated sodium bicarbonate solution. After dilution with ethyl acetate the batch is allowed to come to room temperature, stirred for 10 minutes and extracted twice with ethyl acetate. The combined organic extracts are washed with saturated NaCl solution and dried over sodium sulfate. The solvent is evaporated and the residue purified by preparative thin layer chromatography on silica gel (ethyl acetate in hexane 33%). 6.5 mg of the desired compound are isolated.

$^1$H-NMR (CDCl$_3$); δ=3.56 (d, 1H), 3.77 (d, 1H), 4.98 (br, 1H), 5.14 (s, 1H), 6.48 (d, 1H), 6.78 (d, 1H), 7.02 (s, 1H), 7.14-7.30 (m, 4H), 7.50 (m, 2H), 7.79 (d, 1H), 7.96 (d, 1H).

Example 6

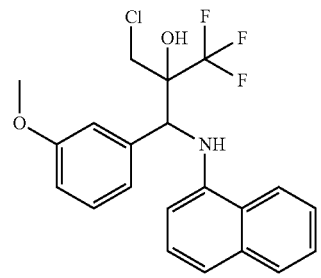

α-Chloromethyl-3-methoxy-β-[(naphth-1-yl)amino]-α-(trifluoromethyl)benzeneethanol Is isolated as a side product in example 4.

$^1$H-NMR (CDCl$_3$); δ=3.76 (s, 3H), 3.80 (d, 1H), 4.87 (d, 1H), 5.35 (s, 1H), 6.54 (d, 1H), 6.86 (d, 1H), 7.09 (s, 1H), 7.10 (d, 1H), 7.16-7.28 (m, 3H), 7.50 (m, 2H), 7.85 (d, 1H), 8.07 (d, 1H).

Example 7

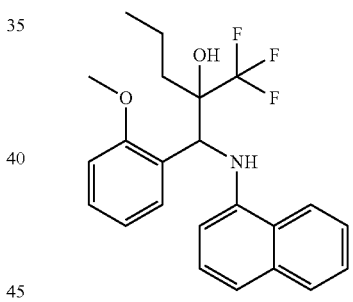

1-(2-Methoxyphenyl-1-[(naphth-1-yl)amino]-2-(trifluormethyl)pentan-2-ol

{[2-Methoxyphenyl][2-(trifluoromethyl)oxiranyl]methyl}naphthalene-1-amine

Analogously to Example 3, the corresponding imine is produced starting from 1-aminonaphthalene and 2-methoxybenzaldehyde in toluene. To 2.11 g (8.1 mmol) [(2-methoxyphenyl)methylene]naphthalene-1-amine in THF are added 0.63 ml (7.4 mmol) of the lithiated 1,1,1-trifluoroepoxypropane at −100° C. analogously to example 3. Typical work up and chromatographic purification on silica gel (ethyl acetate in hexane 10% to 20%) yield 438 mg {[2-methoxyphenyl][2-(trifluoromethyl)oxiranyl]methyl}naphthalene-5-amine as yellow oil.

1H-NMR (CDCl3); δ=2.40 (m, 1H), 3.08 (d, 1H), 3.95 (s, 3H), 5.23 (d, 1H), 5.78 (d, 1H), 6.33 (d, 1H), 6.82 (t, 1H), 6.92-7.05 (m, 2H), 7.20 (m, 2H), 7.28 (m, 1H), 7.50 (m, 2H), 7.84 (d, 1H), 7.98 (d, 1H).

To 30 mg (0.16 mmol) copper(I) iodide in 2 ml THF at −30° C. are added 0.71 ml of a 3-Methyl magnesium bromid in diethyl ether. After 30 minutes at −30° C. 200 mg (0.54 mmol) {[2-methoxyphenyl][2-(trifluoromethyl)oxiranyl]methyl}naphthalene-5-amine in 0.5 ml THF are added. The reaction mixture is stirred for 2 hours while warmed to −10° C. and then poured into a saturated ammonium chloride solution. Phases are separated and the aqueous layer is extracted twice with ethyl acetate. The combined organic phases are washed with brine, died over sodium sulphate and evaporated. Flash chromatography on silica gel (ethyl acetate in hexane 10% to 50%) yields 12 mg of the title compound.

1H-NMR (CDCl3); δ=0.84 (t, 1H), 1.44 (m, 1H), 1.61 (m, 2H), 1.83 (ddd, 1H), 3.98 (s, 3H), 5.37 (s, 1H), 5.67 (br, 1H), 6.39 (m, 1H), 6.91 (t, 1H), 6.95 (d, 1H), 7.18 (m, 2H), 7.26 (d, 1H), 7.40 (d, 1H), 7.49 (m, 2H), 7.76 (d, 1H), 7.91 (d, 1H).

Example 8

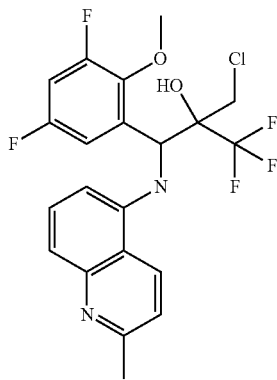

α-Chloromethyl-3,5-difluoro-2-methoxy-β-[(2-methylquinolin-5-yl)amino]-α-(trifluoromethyl)-benzeneethanol {[3,5-Difluoro-2-methoxyphenyl][2-(trifluoromethy)loxiranyl]methyl}-2-methylquinolin-5-amine To 2.0 g (12.6 mmol) 5-amino-2-methylquinolin and 2.2 g (12.6 mmol) 3,5-difluoro-2-methoxybenzaldehyde in 38 ml toluene are added 0.1 ml acetic acid and 5 g molecular sieve. The mixture is heated over 5 hours under reflux and filtrated through a path of cellites after cooling. The solvent is evaporated and the residue is two times azeotrophed with small portions of toluene. 3.43 g of [(3,5-difluoro-2-methoxyphenyl)methylene]-2-methylquinolin-5-amine are obtained as a yellow solid. 1.93 ml (22.3 mmol) 1,1,1-trifluoroepoxypropane in 40 ml THF and 10 ml hexane are cooled to −100° C. and 14 ml of a 1.6 M n-butyl lithium solution in hexane are added over 2 hours while the temperature does not exceed −96° C. 10 Minutes after complete addition 3.44 g (11.2 mmol) [(3,5-difluoro-2-methoxyphenyl)methylene]-2-methylquinolin-5-amine in 50 ml THF are added over 1.5 hours while the temperature temperature does not exceed −95° C. After one hour at −100° C. the reaction mixture is warmed to 0° C. over two hours. The reaction was quenched by addition of saturated ammonium chloride solution. The phases were separated and the aqueous layer was extracted twice with diethyl ether, the combined organic phases washed with brine, dried over sodium sulphate and then evaporated. Flash chromatography on silica gel (isopropanol in hexane 5% to 20%) yields 1.68 g of the desired epoxide.

1H-NMR (CDCl3); δ=2.48 (m, 1H), 2.75 (s, 3H), 3.17 (d, 1H), 4.07 (s, 3H), 5.08 (d, 1H), 5.68 (d, 1H), 6.31 (d, 1H), 6.73 (dd, 1H), 6.83 (ddd, 1H), 7.31 (d, 1H), 7.40 (t, 1H), 7.46 (d, 1H), 8.20 (d, 1H).

To 94 mg (0.74 mmol) aluminium chloride in 3 ml benzene at 5° C. are added 250 mg (0.59 mmol) {[3,5-difluoro-2-methoxyphenyl][2-(trifluoromethyl)oxiranyl]methyl}-2-methylquinolin-5-amine in 2 ml benzene. The reaction mixture is stirred for 3 hours at 25° C. and then poured into a saturated sodium hydrogen carbonate solution. The mixture is vigorously stirred, phases are separated the aqueous layer is extracted twice with ethyl acetate. The combined organic phases are washed with brine, died over sodium sulphate and evaporated. Flash chromatography on silica gel (acetone in hexane 20% to 50%) yields 53 mg of the desired product as a single diastereomer.

1H-NMR (CDCl3); δ=2.73 (s, 3H), 3.70 (d, 1H), 3.81 (d, 1H), 4.04 (s, 3H), 5.50 (d, 1H), 5.55 (d, 1H), 6.44 (d, 1H), 6.85 (ddd, 1H), 7.06 (dd, 1H), 7.30 (d, 1H), 7.41 (t, 1H), 7.44 (d, 1H), 8.13 (d, 1H).

Example 9

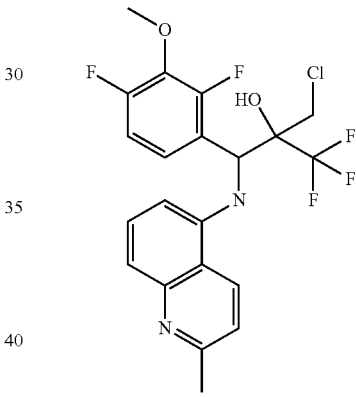

α-Chloromethyl-2,4-difluoro-3-methoxy-β-[(2-methylquinolin-5-yl)amino]-α-(trifluoromethyl)-benzeneethanol {[2,4-Difluoro-3-methoxyphenyl][2-(trifluoromethy)loxiranyl]methyl}-2-methylquinolin-5-amine To 2.0 g (12.6 mmol) 5-amino-2-methylquinolin and 2.18 g (13.6 mmol) 2,3-difluoro-3-methoxybenzaldehyde in 38 ml toluene are added 36 μl acetic acid and 5 g molecular sieve. The mixture is heated over 4 hours under reflux and filtrated through a path of cellites after cooling. The solvent is evaporated and the residue is two times azeotrophed with small portions of toluene. 3.74 g of [(2,4-difluoro-3-methoxyphenyl)methylene]-2-methylquinolin-5-amine are obtained as a yellow solid. 2.06 ml 1,1,1-trifluoroepoxypropane in 35 ml THF and 10 ml hexane are cooled to −100° C. and 15 ml of a 1.6 M n-butyl lithium solution in hexane are added over 2 hours while the temperature does not exceed −95° C. 10 Minutes after complete addition 3.74 g (12 mmol) [1-(2,4-difluoro-3-methoxyphenyl)methylene]-2-methylquinolin-5-amine in 45 ml THF are added over one hour while the temperature does not exceed −95° C. After one hour at −100°

C. 11 ml diethyl ether are added and the reaction mixture is warmed to −10° C. over one hour. The reaction is quenched by addition of saturated ammonium chloride solution. The phases were separated and the aqueous layer was extracted twice with diethyl ether, the combined organic phases washed with brine, dried over sodium sulphate and then evaporated. Flash chromatography on silica gel (ethyl acetate in hexane 10 to 50%) yields 3.66 g of {[2,4-difluoro-3-methoxyphenyl][2-(trifluoromethyl)oxiranyl]methyl}-2-quinolin-5-amine as yellow solid.

¹H-NMR (CDCl₃); δ=2.60 (m, 1H), 2.74 (s, 3H), 3.20 (d, 1H), 4.06 (s, 3H), 5.03 (d, 1H), 5.60 (d, 1H), 6.36 (d, 1H), 6.81 (dd, 1H), 6.89 (dd, 1H), 7.30 (d, 1H), 7.40 (t, 1H), 7.45 (d, 1H), 8.18 (d, 1H).

To 98 mg (0.74 mmol) aluminium chloride in 3 ml benzene at 5° C. are added 261 mg {(2,4-difluoro-3-methoxyphenyl)[2-(trifluoromethyl)oxiranyl]methyl}-(2-methylquinolin-5-yl)amine in 2 ml benzene. The reaction mixture is stirred for 16 hours at 25° C. and then poured into a saturated sodium hydrogen carbonate solution. The mixture is vigorously stirred, phases are separated the aqueous layer is extracted twice with ethyl acetate. The combined organic phases are washed with brine, died over sodium sulphate and evaporated. Flash chromatography on silica gel (acetone in hexane 10%) yields 184 mg of the desired product as a single diastereomer.

¹H-NMR (CDCl₃); δ=2.72 (s, 3H), 3.76 (d, 1H), 3.85 (d, 1H), 4.02 (s, 3H), 5.42 (d, 1H), 5.56 (s, 1H), 6.46 (d, 1H), 6.86 (dd, 1H), 7.20 (dd, 1H), 7.27 (d, 1H), 7.39 (t, 1H), 7.43 (d, 1H), 8.13 (d, 1H).

Example 10

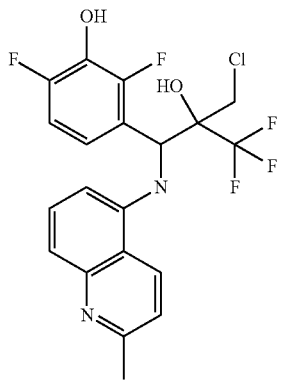

α-Chloromethyl-2,4-difluoro-3-hydroxy-β-[(2-methylquinolin-5-yl)amino]-α-(trifluoromethyl)-benzeneethanol To 50 mg (0.11 mmol) of α-Chloromethyl-2,4-difluoro-3-methoxy-β-[(2-methylquinolin-5-yl)amino]-α-(trifluoromethyl)benzeneethanol in 4.9 dichloromethane at 0° C. are added 2.1 ml of a 1 M solution of boron tribromide in dichloromethane under argon. The reaction mixture is stirred for 16 hours in a temperature range of between 0° C. and 25° C. The reaction mixture is mixed at 0° C. with saturated sodium bicarbonate solution. After dilution with ethyl acetate the batch is allowed to come to room temperature, stirred for 10 minutes and extracted twice with ethyl acetate. The combined organic extracts are washed with saturated NaCl solution and dried over sodium sulfate. The solvent is partially evaporated and the remaining residue is passed through a short path of silica gel (ethyl acetate 100%). 43 mg of the desired compound are isolated.

¹H-NMR (CD₃OD); δ=2.65 (s, 3H), 3.25 (d, 1H), 3.72 (d, 1H), 5.45 (s, 1H), 6.53 (d, 1H), 6.85 (dd, 1H), 7.13 (ddd, 1H), 7.24 (d, 1H), 7.35 (d, 1H), 7.41 (t, 1H), 8.39 (d, 1H).

Example 11

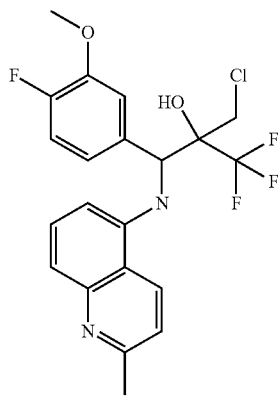

α-Chloromethyl-4-fluoro-3-methoxy-β-[(2-methylquinolin-5-yl)amino]-α-(trifluoromethyl)-benzeneethanol {[4-Fluoro-3-methoxypheny])[2-(trifluoromethl) oxiranyl]methyl}-2-methylquinolin-5-amine Analogously to Example 9, the corresponding imine is produced starting from 2.0 g (12.6 mmol) 5-amino-2-methylquinolin and 1.95 g (13.6 mmol) 4-fluoro-3-methoxybenzaldehyde in toluene. To 3.49 g [(4-fluoro-3-methoxyphenyl)methylene]-2-methylquinolin-5-amine in THF are added 2.04 ml of the lithiated 1,1,1-trifluoroepoxypropane at −100° C. analogously to example 9. Typical work up and chromatographic purification on silica gel (isopropanol in hexane 10% to 20%) yield 3.59 g {(4-fluoro-3-methoxyphenyl)[2-(trifluoromethyl)oxiranyl}methyl]quinolin-5-ylamine as yellow solid.

¹H-NMR (CDCl₃); δ=2.63 (m, 1H), 2.77 (s, 3H), 3.16 (d, 1H), 3.84 (s, 3H), 5.14 (d, 1H), 5.17 (d, 1H), 6.34 (d, 1H), 6.92 (ddd, 1H), 6.96 (dd, 1H), 7.06 (dd, 1H), 7.29 (d, 1H), 7.35 (t, 1H), 7.42 (d, 1H), 8.18 (d, 1H).

To 98 mg (0.74 mmol) aluminium chloride in 3 ml benzene at 5° C. are added 250 mg (0.62 mmol) {[4-fluoro-3-methoxyphenyl][2-(trifluoromethyl)oxiranyl]methyl}-(2-methylquinolin-5-yl)amine in 2 ml benzene. The reaction mixture is stirred for 16 hours at 25° C. and then poured into a saturated sodium hydrogen carbonate solution. The mixture is vigorously stirred, phases are separated the aqueous layer is extracted twice with ethyl acetate. The combined organic phases are washed with brine, died over sodium sulphate and evaporated. Flash chromatography on silica gel (acetone in hexane 10%) yields 125 mg of the desired product as a single diastereomer.

¹H-NMR (CDCl₃); δ=2.69 (s, 3H), 3.49 (d, 1H), 3.79 (d, 1H), 3.87 (s, 3H), 5.09 (d, 1H), 5.78 (d, 1H), 6.43 (d, 1H), 7.06 (dd, 1H), 7.10 (m, 2H), 7.21 (d, 1H), 7.36 (t, 1H), 7.38 (d, 1H), 8.29 (d, 1H).

Example 12

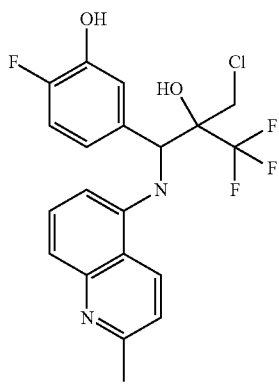

α-Chloromethyl-4-fluoro-3-methoxy-β-[(2-methylquinolin-5-yl)amino]-α-(trifluoromethyl)-benzeneethanol To 50 mg (0.11 mmol) of α-chloromethyl-4-fluoro-3-methoxy-β-[(2-methylquinolin-5-yl)amino]-α-(trifluoromethyl)-benzeneethanol in 5.1 dichloromethane at −20° C. are added 1.9 ml of a 1 M solution of boron tribromide in dichloromethane under argon. The reaction mixture is stirred for 16 hours in a temperature range of between −20° C. and 25° C. The reaction mixture is mixed at 0° C. with saturated sodium bicarbonate solution. After dilution with ethyl acetate the batch is allowed to come to room temperature, stirred for 15 minutes and extracted twice with ethyl acetate. The combined organic extracts are washed with saturated NaCl solution and dried over sodium sulfate. The solvent is evaporated and the residue is purified by preparative thin layer chromatography on silica gel (acetone in hexane 50%). 19 mg of the desired compound are isolated.

¹H-NMR (CD₃OD); δ=2.67 (s, 3H), 3.14 (d, 1H), 3.70 (d, 1H), 5.06 (s, 1H), 6.48 (d, 1H), 7.00 (dd, 1H), 7.08 (m, 1H), 7.20 (d, 2H), 7.36 (d, 1H), 7.37 (t, 1H), 8.42 (d, 1H).

Example 13

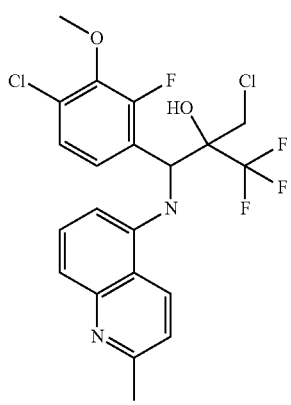

α-Chloromethyl-4-chloro-2-fluoro-3-methoxy-β-[(2-methylquinolin-5-yl)-amino]-α-(trifluoromethyl)-benzeneethanol {[4-Chloro-2-fluoro-3-methoxyphenyl][2-(trifluoromethyl)oxiranyl]methyl}-2-methylquinolin-5-amine Analogously to Example 9, the corresponding imine is produced starting from 0.84 g (5.3 mmol) 5-amino-2-methylquinolin and 1.0 g (5.0 mmol) 4-chloro-2-fluoro-3-methoxybenzaldehyde in toluene. 1.35 g [(4-chloro-2-fluoro-3-methoxyphenyl)methylene]-2-methylquinolin-5-amine in THF are added to 0.71 ml of the lithiated 1,1,1-trifluoroepoxypropane at −100° C. analogously to example 9. Typical work up and chromatographic purification on silica gel (ethyl acetate in hexane 10% to 50%) yield 1.11 g {[4-chloro-2-fluoro-3-methoxyphenyl][2-(trifluoromethyl)oxiranyl]methyl]quinolin-5-ylamine as yellow solid.

¹H-NMR (CDCl₃); δ=2.63 (m, 1H), 2.74 (s, 3H), 3.21 (d, 1H), 4.02 (s, 3H), 5.04 (d, 1H), 5.61 (d, 1H), 6.34 (d, 1H), 6.91 (dd, 1H), 7.07 (d, 1H), 7.29 (d, 1H), 7.40 (t, 1H), 7.46 (d, 1H), 8.17 (d, 1H).

To 90 mg (0.68 mmol) aluminium chloride in 2.8 ml benzene at 5° C. are added 250 mg (0.57 mmol) {(4-chloro-2-fluoro-3-methoxyphenyl)[2-(trifluoromethyl)oxiranyl]methyl}-(2-methylquinolin-5-yl)amine in 2 ml benzene. The reaction mixture is stirred for 4 hours at 25° C. and then poured into a saturated sodium hydrogen carbonate solution. The mixture is vigorously stirred, phases are separated the aqueous layer is extracted twice with ethyl acetate. The combined organic phases are washed with brine, died over sodium sulphate and evaporated. Flash chromatography on silica gel (acetone in hexane 10%) yields 115 mg of the desired product as a single diastereomer.

$^1$H-NMR (CDCl$_3$); δ=2.72 (s, 3H), 3.81 (s, 2H), 3.98 (s, 3H), 5.45 (d, 1H), 5.56 (d, 1H), 6.46 (d, 1H), 7.12 (dd, 1H), 7.22 (d, 1H), 7.28 (d, 1H), 7.40 (t, 1H), 7.44 (d, 1H), 8.13 (d, 1H).

Example 14

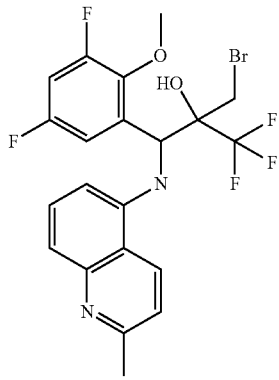

α-Bromomethyl-3,5-difluoro-2-methoxy-β-[(2-methylquinolin-5-yl)-amino]-α-(trifluoromethyl)-benzeneethanol To 151 mg (0.57 mmol) aluminium bromide in 2.3 ml benzene at 5° C. are added 200 mg (0.47 mmol) {[3,5-difluoro-2-methoxyphenyl][2-(trifluoromethyl)oxiranyl]methyl}-2-methylquinolin-5-amine in 2 ml benzene. The reaction mixture is stirred for 3 hours at 25° C. and then poured into a saturated sodium hydrogen carbonate solution. The mixture is vigorously stirred, phases are separated the aqueous layer is extracted twice with ethyl acetate. The combined organic phases are washed with brine, died over sodium sulphate and evaporated. Flash chromatography on silica gel (acetone in hexane 20% to 50%) yields 44 mg of the desired product as a single diastereomer.

$^1$H-NMR (CDCl$_3$); δ=2.75 (s, 3H), 3.63 (d, 1H), 3.72 (d, 1H), 4.07 (s, 3H), 5.51 (d, 1H), 5.56 (d, 1H), 6.42 (d, 1H), 6.83 (ddd, 1H), 7.04 (d, 1H), 7.28 (d, 1H), 7.42 (t, 1H), 7.46 (d, 1H), 8.15 (d, 1H).

Example 15

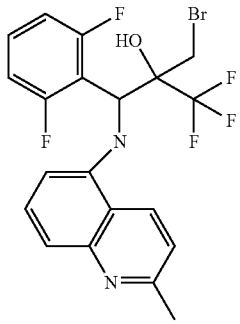

α-Bromomethyl-2,6-difluoro-β-[(2-methylquinolin-5-yl-amino]-α-(trifluoromethyl)-benzeneethanol {(2,6-Difluorophenyl)[2-(trifluoromethyl)oxiranyl]methyl}-2-methylquinolin-5-amine Analogously to Example 9, the corresponding imine is produced starting from amino-2-methylquinolin and 2,6-difluorobenzaldehyde in toluene. To 3.08 g (10.9 mmol) [(2,6-difluorophenyl)methylene]-2-methylquinolin-5-amine in THF are added 1.88 ml (21.8 mmol) of the lithiated 1,1,1-trifluoroepoxypropane at −100° C. analogously to example 9. Typical work up and chromatographic purification on silica gel (ethyl acetate in hexane 10% to 50%) yield 3.1 g {[2,6-difluorophenyl][2-(trifluoromethyl)oxiranyl]methyl}quinolin-5-amine as brown solid.

$^1$H-NMR (CDCl$_3$); δ=2.72 (s, 3H), 2.86 (m, 1H), 3.21 (d, 1H), 5.05 (d, 1H), 5.17 (d, 1H), 5.87 (d, 1H), 6.64 (dd, 1H), 6.90 (d, 1H), 6.92 (d, 1H), 7.26 (m, 2H), 7.46 (m, 2H), 8.12 (d, 1H).

Analogously to example 14 250 mg (0.63 mmol) {[2,4-difluorophenyl][2-(trifluoromethyl)oxiranyl]methyl}-2-methylquinolin-5-amine are reacted with 203 mg (0.76 mmol) aluminium bromide in benzen. The typical work up after 3 hours and chromatography on silica gel (acetone in hexane 10 to 50%) yields 141 mg of the title compound as a single diastreomer.

$^1$H-NMR (CDCl$_3$); δ=2.75 (s, 3H), 3.85 (d, 1H), 3.96 (d, 1H), 5.60 (d, 1H), 5.71 (d, 1H), 6.63 (d, 1H), 6.88 (dd, 1H), 6.93 (m, 2H), 7.26 (m, 2H), 7.46 (t, 1H), 7.51 (d, 1H) 8.15 (d, 1H).

Example 16

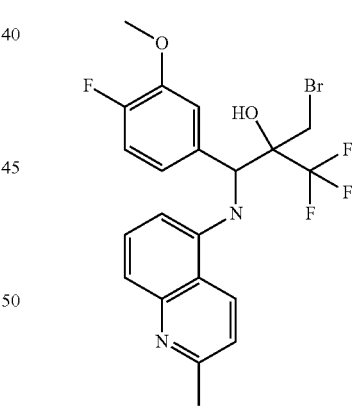

α-Bromomethyl-4-fluoro-3-methoxy-β-[(2-methylquinolin-5-yl)amino]-α-(trifluoromethyl)benzeneethanol Analogously to example 13 250 mg (0.62 mmol) {[4-fluoro-3-methoxyphenyl][2-(trifluoromethyl)oxiranyl]methyl}-2-methylquinolin-5-amine are reacted with 197 mg (0.74 mmol) aluminium bromide in benzen. The typical work up after 3 hours and chromatography on silica gel (acetone in hexane 10 to 50%) yields 112 mg of the title compound as a single diastreomer.

¹H-NMR (CDCl₃); δ=2.71 (s, 3H), 3.37 (d, 1H), 3.66 (d, 1H), 3.88 (s, 3H), 5.11 (d, 1H), 5.77 (d, 1H), 6.44 (d, 1H), 7.06 (dd, 1H), 7.13 (m, 1H), 7.24 (d, 1H), 7.27 (m, 1H), 7.36 (t, 1H), 7.42 (d, 1H), 8.33 (d, 1H).

Example 17

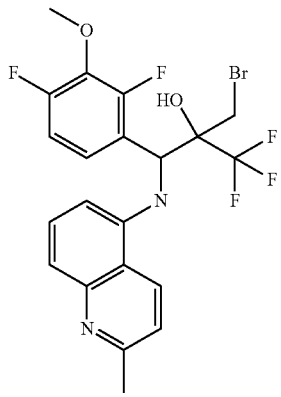

α-Bromomethyl-2,4-difluoro-3-methoxy-β-[(2-methylquinolin-5-yl)amino]-α-(trifluoromethyl)-benzeneethanol Analogously to example 14 261 mg (0.63 mmol) {[2,4-difluorophenyl][2-(trifluoromethyl)oxiranyl]methyl}-2-methylquinolin-5-amine are reacted with 197 mg (0.76 mmol) aluminium bromide in benzen. The typical work up after 3 hours and chromatography on silica gel (isopropanol in hexane 5 to 20%) yields 121 mg of the title compound as a single diastreomer.

¹H-NMR (CDCl₃); δ=2.74 (s, 3H), 3.67 (s, 2H), 4.02 (s, 3H), 5.45 (d, 1H), 5.58 (d, 1H), 6.46 (d, 1H), 6.86 (dd, 1H), 7.20 (m, 1H), 7.27 (d, 1H), 7.42 (t, 1H), 7.43 (d, 1H) 8.17 (d, 1H).

Example 18

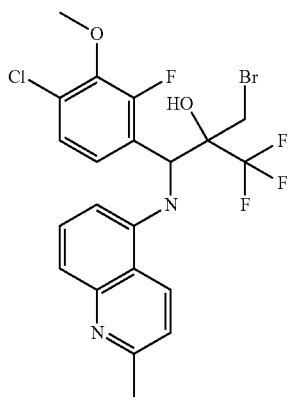

α-Bromomethyl-4-chloro-2-fluoro-3-methoxy-β-[(2-methylquinolin-5-yl)amino]-α-(trifluoromethyl)-benzeneethanol Analogously to example 14 250 mg (0.57 mmol) {[4-chloro-2-fluorophenyl][2-(trifluoromethyl)oxiranyl]methyl}-2-methylquinolin-5-amine are reacted with 181 mg (0.68 mmol) aluminium bromide in benzen. The typical work up after 3 hours and chromatography on silica gel (isopropanol in hexane 10 to 50%) yields 129 mg of the title compound as a single diastreomer.

¹H-NMR (CDCl₃); δ=2.74 (s, 3H), 3.67 (s, 2H), 4.02 (s, 3H), 5.45 (d, 1H), 5.58 (d, 1H), 6.46 (d, 1H), 6.86 (dd, 1H), 7.20 (m, 1H), 7.27 (d, 1H), 7.42 (t, 1H), 7.43 (d, 1H) 8.17 (d, 1H).

Example 19

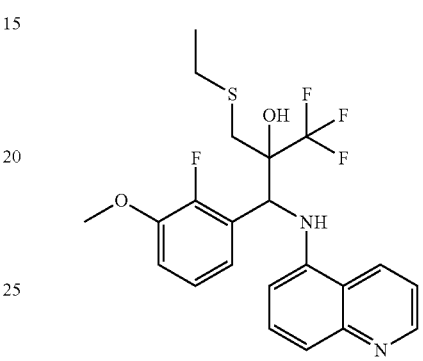

α-[(Ethylsulfanyl)methyl]-2-fluoro-3-methoxy-β-[(quinolin-5-yl)amino]-α-trifluoromethyl)benzeneethanol {12-Fluoro-3-methoxyphenyl][2-(trifluoromethyl)oxiranyl]methyl}quinolin-5-amine Analogously to Example 9, the corresponding imine is produced starting from 2.0 g (12.6 mmol) 5-aminoquinolin and 1.95 g (13.6 mmol) 2-fluoro-2-methoxbenzaldehyde in toluene, which is reacted with the lithiated 1,1,1-trifluoroepoxypropane at −100° C.

1H-NMR (DMSO-d6); δ=2.92 (m, 1H), 3.29 (d, 1H), 3.85 (s, 3H), 5.64 (d, 1H), 6.53 (d, 1H), 6.59 (d, 1H, NH), 7.07-7.23 (m, 3H), 7.31 (d, 1H), 7.45 (t, 1H), 7.49 (d, 1H), 8.76 (dm, 1H), 8.83 (dd, 1H).

[(2-Fluoro-3-methoxyphenyl)-2-(2-trifluoromethyl-oxiranyl)ethyl]quinolin-5-yl-amine (97 mg, 0.25 mmol) was dissolved in DMF (0.5 mL). Caesium carbonate (161 mg, 0.5 mmol) was added followed by ethanethiol (75 µL, 1 mmol). The mixture was vigorously stirred at ambient temperature for 90 minutes. The reaction mixture was partitioned between diethylether and water. The organic phase was washed trice with water and then with brine and evaporated. The residue was dissolved in methylene chloride, filtered through a plug of glass wool to remove residual NaCl and again evaporated. The crude product was dissolved in methylene chloride and flash-chromatographed on a column of silica using a gradient of heptane-ethyl acetate (10→90% ethyl acetate) to yield the title product (60 mg, 53%) as an amorphous solid.

¹H-NMR (DMSO-d₆); δ=1.09 (t, 3H), 2.47 (dd, 1H), 2.93 (d, 1H), 3.82, (s, 3H), 5.43 (d, 1H), 6.39 (d, 1H, NH), 6.47 (d, 1H), 7.04-7.12 (m, 3H, incl. OH), 7.24 (d, 1H), 7.30 (m, 1H), 7.45 (t, 1H), 7.50 (dd, 1H), 8.55 (d, 1H), 8.83 (dd, 1H).

¹⁹F-NMR (dmso-d₆); −72.8, −137.8

Example 20

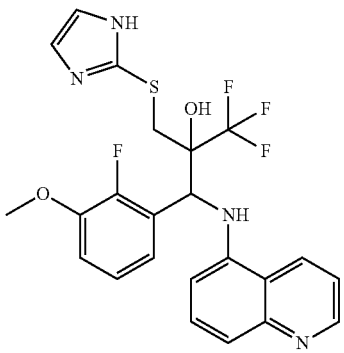

2-Fluoro-α-{[(imidazole-2-yl)sulfanyl]methyl}-3-methoxy-β-[(quinolin-5-yl)amino)-α-(trifluoromethyl)benzeneethanol {[2-(2-Fluoro-3-methoxyphenyl][2-(trifluoromethyl)oxiranyl]methyl}quinolin-5-amine (100 mg, 0.25 mmol) is dissolved in DMF (0.5 mL). Caesium carbonate (136 mg, 0.4 mmol) is added followed by 1H-imidazole-2-thiol (98 mg, 0.5 mmol). The mixture is stirred for 90 min and then partitioned between ethyl acetate and water. The organic phase is washed with water, followed by brine and then evaporated. Flash chromatography using SiO₂ and a gradient of heptane-ethyl acetate (10→90% ethyl acetate) gives somewhat impure title product (113 mg). Part of the material (75 mg) was subjected to preparative HPLC (RP C-18 column, gradient CH₃CN/Water, 0.1% trifluoroacetic acid) followed by lyophilization gives pure, amorphous title compound di-trifluoroacetic acid salt as a single diastereomer (77 mg, 55%).

¹H-NMR (DMSO-d₆, D₂O added); δ=3.42 (d, 1H), 3.72 (d, 1H), 3.81 (s, 3H), 5.40 (s, 1H), 6.62, (d, 1H), 7.07 (s, 1H), 7.09 (m, 1H), 7.26 (m, 2H), 7.38 (d, 1H), 7.46 (s, 2H), 7.75 (t, 1H), 7.85 (d, 1H), 9.08 (dd, 1H), 9.20 (m, 1H).

¹⁹F-NMR (DMSO-d₆, D₂O added); δ=−73.2, −74.1, −138.5.

Example 21

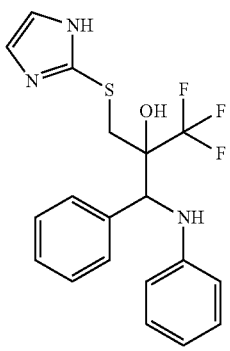

α-{[(Imidazole-2-yl)sulfanyl]methyl}-β-(Phenylamino)-α-(trifluoromethyl)benzeneethanol N-{Phenyl[2-(trifluoromethy)loxiranyl]methyl}aniline (73 mg, 0.25 mmol) is dissolved in DMF (0.5 mL). Caesium carbonate (135 mg, 0.4 mmol) and 1H-imidazole-2-thiol (100 mg, 0.5 mmol) are added, the mixture is stirred for 90 min at ambient temperature and then partitioned between ethyl acetate and water. The organic phase is washed with water, followed by brine and then evaporated to give pure title compound as a white amorphous powder (diastereomeric mixture, ratio 1:3.3).

¹H-NMR (DMSO-d₆); δ=3.19 (d, 1H), 3.49 (d, 0.77H), 3.82 (d, 0.23H), 4.86 (d, 1H), 5.95 (d, 0.77H, NH), 6.14 (d, 0.23H, NH), 6.48 (t, 1H), 6.59-6.67 (m, 2H), 6.88-7.02 (m, 3H), 7.04-7.31 (m, 4H), 7.49 (t, 1H), 8.48 (d, 1H), 8.43 (s, 0.77H), 8.54 (s, 0.23H), 12.44 (s, 1H).

¹⁹F-NMR (DMSO-d₆, D₂O added); δ=−72.2, −72.5.

Example 22

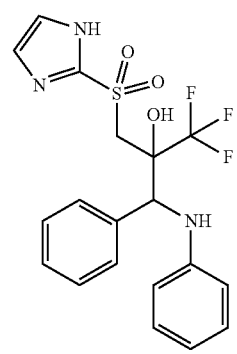

α-{[(Imidazole-2-yl)sulfonyl]methyl}-β-(phenyl)amino)-α-(trifluoromethyl)benzeneethanol α-{[(Imidazole-2-yl)sulfanyl]methyl}-β-(phenylamino)-α-(trifluoromethyl)benzeneethanol (diastereomeric mixture 1:3.3) 50 mg, 0.13 mmol) is dissolved in ethyl acetate (10 mL). Saturated aqueous sodiumhydrogen carbonate (2.4 mL) is added followed by m-chloroperbenzoic acid (74%, 70 mg, 0.3 mmol). The mixture is stirred at ambient temperature for 1 h and dimethylsulphide (100 L) is then added. Stirring is continued for a couple of minutes and the phases are then separated. The organic phase is washed twice with water, once with brine and then evaporated. Flash chromatography (SiO2, heptane-ethyl acetate gradient) gives the pure title compound as a pale yellow solid (45 mg, 83%, diastereomeric ratio 1:3.3)

¹H-NMR (DMSO-d₆); δ=3.41 (d, 0.77H), 3.68 (d, 0.23H), 3.88 (d, 0.77H), 4.41 (d, 0.23H), 5.09 (d, 0.23H), 5.29 (d, 0.77H), 6.08 (d, 0.8H, NH), 2.09 (d, 0.2H, NH), 6.46-6.55 (m, 1H), 6.64 (t, 2H), 7.00 (m, 3H), 7.16-7.64 (m, 6H), 13.81 (s, 1H).

¹⁹F-NMR (DMSO-d₆); δ=−71.5, −71.7.

Example 23

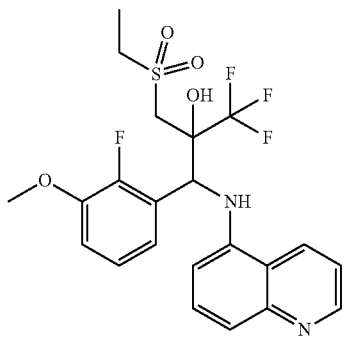

α-[(Ethylsulfonyl)methyl]-2-fluoro-3-methoxy-β-[(quinolin-5-yl)amino]-α-(trifluoromethyl)benzeneethanol α-[(Ethylsulfanyl)methyl]-2-fluoro-3-methoxy-β-[(quinolin-5-yl)amino]-α-(trifluoromethyl)benzeneethanol (36 mg, 0.08 mmol) is dissolved in ethyl acetate (15 mL). Saturated aqueous sodiumhydrogen carbonate (2.5 mL) is added followed by m-chloroperbenzoic acid (74%, 51 mg, 0.22 mmol). The mixture is stirred at ambient temperature for 2.5 h and dimethylsulphide (100 µL) is added. Stirring is continued for 20 minutes and the phases were then separated. The organic phase is washed trice with water, once with brine and then evaporated. Flash chromatography (SiO2, heptane-ethyl acetate gradient) and lyophilization ratio from dioxane gave the title compound as a single diastereomer (15 mg, 39%).

$^{1}$H-NMR (DMSO-$d_6$); δ=1.24 (t, 3H), 3.72 (s, 2H), 3.83 (s, 3H), 5.52 (d, 1H), 6.36 (d, 1H), 6.79 (d, 1H), 7.06-7.16 (m, 2H), 7.21 (dd, 1H), 7.28 (d, 1H), 7.46 (t, 1H), 7.55 (dd, 1H), 7.62 (s, 1H), 8.68 (d, 1H), 8.86 (dd, 1H).

$^{1}$H-NMR (DMSO-$d_6$), D$_2$O added); δ=δ=1.19 (t, 3H), 3.29 (m, 2H), 3.67 (s, 2H), 3.83 (s, 3H), 5.53 (s, 1H), 6.37 (d, 1H), 7.03-7.21 (m, 3H), 7.27 (d, 1H), 7.44 (t, 1H), 7.52 (dd, 1H), 8.62 (d, 1H), 8.80 (dd, 1H).

$^{19}$F-NMR (DMSO-$d_6$, D$_2$O added); δ=−73.7, −138.0.

Example 24

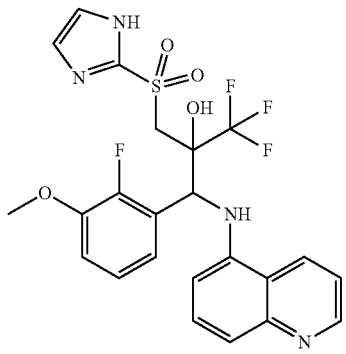

2-Fluoro-α-{[(imidazole-2-yl)sulfonyl]methyl}-3-methoxy-β-[(quinolin-5-yl)amino]-α-(trifluoromethyl)benzeneethanol 2-Fluoro-α-{[(imidazole-2-yl)sulfanyl]methyl}-3-methoxy-β-[(quinolin-5-yl)amino]-α-(trifluoromethyl)benzeneethanol di-trifluoroacetic acid salt (52 mg, 0.07 mmol) is dissolved in ethyl acetate (10 mL). Saturated aqueous sodiumhydrogen carbonate (2.5 mL) is added and the mixture is cooled to 0° C. m-chloroperbenzoic acid (74%, 35 mg, 0.15 mmol) is added and the mixture was stirred at 0° C. for 1 h and dimethylsulphide (100 µL) was then added. The cooling bath was removed and stirring was continued for additional 10 minutes. Ethyl acetate is added and the phases were separated. The organic phase was washed trice with water, once with brine and then evaporated. Flash chromatography (SiO2, heptane-ethyl acetate gradient) and lyophilization ratio from dioxane gave the title compound as a single diastereomer (24 mg, 63%).

$^{1}$H-NMR (DMSO-$d_6$); δ=3.83 (s, 3H), 3.86 (d, 1H), 4.27 (d, 1H), 5.45 (d, 1H), 6.37 (d, 1H), 6.40 (d, 1H, NH), 7.03-7.14 (m, 2H), 7.15-7.59 (7H), 8.71 (d, 1H), 8.85 (dd, 1H), 13.74 (s, 1H, imidazole NH).

$^{19}$F-NMR (DMSO-$d_6$); δ=−74.6, −137.9.

Example 25

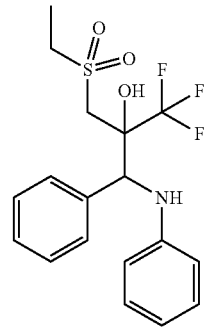

α[(Ethylsulfonyl)methyl]-β(Phenylamino)-α(trifluoromethyl)benzeneethanol

α-[(Ethylsulfanyl)methyl]-β-[(phenyl)amino]-α-(trifluoromethyl)benzeneethanol (46 mg, 0.13 mmol, diastereomeric mixture, ratio 1:5) was dissolved in ethyl acetate (10 mL). Saturated aqueous sodiumhydrogen carbonate (2.5 mL) was added followed by m-chloroperbenzoic acid (74%, 70 mg, 0.3 mmol). After stirring for 70 min at ambient temperature, additional m-chloroperbenzoic acid (10 mg) was added and the mixture was stirred for additional 10 min. Dimethylsulphide (100 L) was added and stirring was continued for 5 min. The phases were separated and the organic phase was washed trice with water, once with brine and then evaporated. Flash chromatography (SiO2, heptane-ethyl acetate gradient) gave the title compound as a diastereomeric mixture (19 mg, 38%, diastereomeric ratio 1:5).

$^{1}$H-NMR (DMSO-$d_6$); δ=1.03 (t, 0.5H), 1.12 (t, 2.5H), 3.01-3.22 (m, 3H), 3.64 (d, 0.84H), 4.01 (d, 0.16H), 5.12 (d, 0.16H), 5.22 (d, 0.84H), 6.07 (d, 0.16H), 6.13 (d, 0.84H), 6.46-6.56 (m, 1H), 6.58-6.68 (m, 2H), 6.96-7.05 (m, 3H), 7.20-7.37 (m, 3H), 7.49 (d, 0.3H), 7.57 (d, 1.7H).

$^{19}$F-NMR (DMSO-$d_6$); δ=−70.9, −71.7.

Example 26

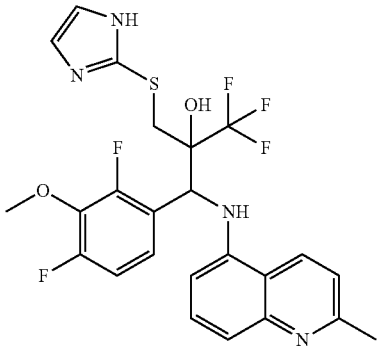

2,4-Difluoro-α-{[(imidazole-2-yl)sulfanyl]methyl}-3-methoxy-β-[(quinolin-5-yl)amino)-α-(trifluoromethyl)benzeneethanol 200 mg (0.47 mmol) {[2,4-difluoro-3-methoxyphenyl][2-(trifluoromethyl)oxiranyl]methyl}-2-quinolin-5-amine (example 9) are dissolved in 2.0 ml DMF. 307 mg (0.94 mmol) caesium carbonate are added followed by 189 mg (1.89 mmol) 2-mercaptoimidazole. The mixture is vigorously stirred at ambient temperature for 4 hours. The reaction mixture is partitioned between ethyl acetate and water. The organic phase is washed with water and brine and evaporated. Flash chromatography on silica gel (acetone in hexane 10% to 50%) yields 132 mg of the title compound as one single diastereomer.

$^1$H-NMR (CDCl$_3$); δ=2.71 (s, 3H), 3.24 (d, 1H), 3.43 (d, 1H), 4.00 (s, 3H), 5.30 (d, 1H), 5.95 (d, 1H), 6.32 (d, 1H), 6.80 (t, 1H), 6.99 (s, 2H), 7.20 (dd, 1H), 7.26 (d, 1H), 7.35 (t, 1H), 7.38 (d, 1H), 8.21 (d, 1H).

Example 27

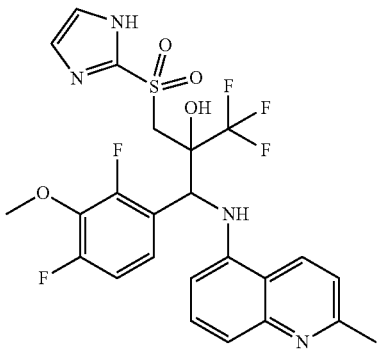

2,4-Difluoro-α-{[(imidazole-2-yl)sulfonyl]methyl}-3-methoxy-β-[(quinolin-5-yl)amino)-α-(trifluoromethyl)benzeneethanol 30 mg (0.06 mmol) 2,4-difluoro-α-{[(imidazole-2-yl)sulfanyl]methyl}-3-methoxy-β-[(2-methylquinolin-5-yl)amino)-α-(trifluoromethyl)benzeneethanol are dissolved in 6 ml ethyl acetate and 1.5 ml saturated aqueous sodium hydrogen carbonate is added followed by 32 mg (0.14 mmol) m-chloroperbenzoic acid. The two phased mixture is stirred vigorously for one hour at ambient temperature. The reaction is diluted with water, the phases are separated and the organic layer is washed with water and brine. After evaporation the residue is purified by preparative thin layer chromatography on silica gel (ethyl acetate/hexane/methanol 4:4:1). to give 3 mg of the desired sulfone as an amorphous solid.

$^1$H-NMR (CD$_3$OD); δ=2.67 (s, 3H), 3.93 (d, 1H), 3.93 (s, 3H), 5.50 (s, 1H), 6.30 (d, 1H), 6.93 (dd, 1H), 7.28 (s, 1H), 7.38 (t, 1H), 7.42 (d, 1H), 7.52 (dd, 1H), 7.88 (d, 1H), 7.94 (s, 1H), 8.65 (d, 1H).

Example 28

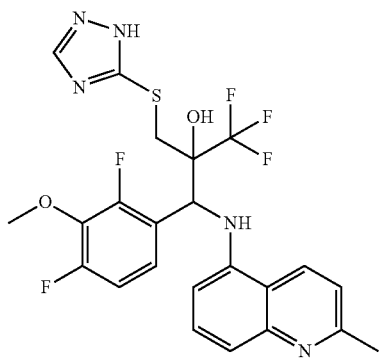

2,4-Difluoro-α-{[(1,2,4-triazol-3-yl)sulfanyl]methyl}-3-methoxy-β-[(quinolin-5-yl)amino)-α-(trifluoromethyl)benzeneethanol 200 mg (0.47 mmol) {[2,4-difluoro-3-methoxyphenyl][2-(trifluoromethyl)oxiranyl]methyl}-2-methylquinolin-5-amine (example 9) are dissolved in 2.0 ml DMF. 307 mg (0.94 mmol) Caesium carbonate are added followed by 190 mg (1.89 mmol) 3-mercapto-1,2,4-triazole. The mixture is vigorously stirred at ambient temperature for 4 hours. The reaction mixture is partitioned between ethyl acetate and water. The organic phase is washed with water and brine and evaporated. Flash chromatography on silica gel (acetone in hexane 10% to 50%) yields 66 mg of the title compound as one single diastereomer.

$^1$H-NMR (DMSO d$_6$); δ=2.57 (s, 3H), 3.35 (d, 1H), 3.67 (d, 1H), 3.81 (s, 3H), 5.31 (d, 1H), 6.29 (d, 1H), 6.33 (d, 1H), 7.06 (dd, 1H), 7.14 (d, 1H), 7.35 (d, 1H), 7.36 (t, 1H), 8.38 (s, 1H), 8.45 (d, 1H).

Example 29

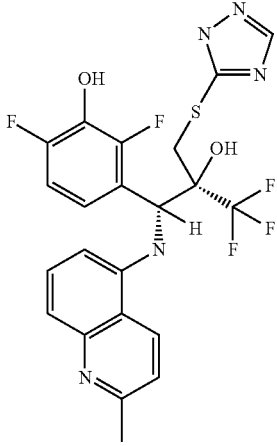

2,4-Difluoro-3-methoxy-α-{[(1,2,4-triazol-3-yl)sulfanyl]methyl}-β-[(2-methylquinolin-5-yl)amino]-α-(trifluoromethyl)-benzeneethanol 50 mg (0.09 mmol) 2,4-difluoro-α-{[(1,2,4-triazol-3-yl)sulfanyl]methyl}-3-methoxy-β-[(2-methylquinolin-5-yl) amino)-α-(trifluoromethyl)benzeneethanol are dissolved in 10 ml ethyl acetate and 2.5 ml saturated aqueous sodium hydrogen carbonate is added followed by 53 mg (0.24 mmol) m-chloroperbenzoic acid. The two phased mixture is stirred vigorously for one hour at ambient temperature. The reaction is diluted with water, the phases are separated and the organic layer is washed with water and brine. After evaporation the residue is purified by preparative thin layer chromatography on silica gel (methanol in dichloromethan 10%). to give 6 mg of the desired sulfone as an amorphous solid.

$^1$H-NMR (CD$_3$OD); δ=2.66 (s, 3H), 3.86 (d, 1H), 3.92 (s, 3H), 3.95 (d, 1H), 5.51 (s, 1H), 6.36 (d, 1H), 6.92 (dd, 1H), 7.24 (d, 1H), 7.37 (t, 1H), 7.41 (d, 1H), 7.45 (dd, 1H), 8.00 (s, 1H), 8.66 (d, 1H).

Example 30

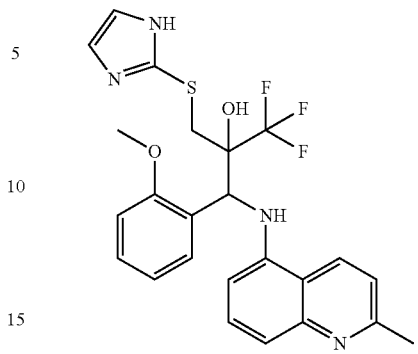

α-{[(Imidazole-2-yl)sulfanyl]methyl}-3-methoxy-β-[(quinolin-5-yl)amino)-α-(trifluoromethyl)benzeneethanol {(2-Methoxyphenyl)[2-(trifluoromethyl)oxiranyl]methyl}-2-methylquinolin-5-amine To 1.74 g (11 mmol) 5-amino-2-methylquinolin and 1.33 ml (11 mmol) 2-methoxybenzaldehyde in 33 ml toluene are added 50 μl acetic acid and 2 g molecular sieve. The mixture is heated over 2 hours under reflux and filtrated through a path of cellites after cooling. The solvent is evaporated and the residue is two times azeothrophed with small portions of toluene. 3.6 g of [1-(2-methoxyphenyl)methylidene]-(2-methylquinolin-5-yl)amine are obtained as a yellow oil. 2.25 ml (26 mmol) 1,1,1-Trifluoroepoxypropane in 38 ml THF and 11 ml hexane are cooled to −100° C. and 15 ml of a 1.6 M n-butyl lithium solution in hexane are added over one hours while the temperature does not exceed −95° C. 10 Minutes after complete addition 3.6 g (11 mmol) raw [1-(2-methoxyphenyl)methylidene]-(2-methylquinolin-5-yl)amine in 49 ml THF are added over one hour while the temperature does not exceed −95° C. After one hour at −100° C. 12 ml diethyl ether are added and the reaction mixture is warmed to −10° C. over one hour. The reaction was quenched by addition of saturated ammonium chloride solution. The phases were separated and the aqueous layer was extracted twice with diethyl ether, the combined organic phases washed with brine, dried over sodium sulphate and then evaporated. Flash chromatography on silica gel (acetone in hexane 0 to 30%) yields 4.27 g {(2-methoxyphenyl)[2-(trifluoromethyl)oxiranyl]methyl}-2-methylquinolin-5-amine as mixture of diastereomers.

Diastereomer 1: $^1$H-NMR (CDCl$_3$); δ=2.38 (m, 1H), 2.74 (s, 3H), 3.09 (d, 1H), 3.95 (s, 3H), 5.15 (d, 1H), 5.74 (d, 1H), 6.31 (d, 1H), 6.84 (t, 1H), 6.94 (d, 1H), 7.16 (d, 1H), 7.28 (d, 1H), 7.29 (t, 1H), 7.36 (t, 1H), 7.40 (d, 1H), 8.23 (d, 1H).

Diastereomer 2: $^1$H-NMR (CDCl$_3$); δ=2.74 (s, 3H), 3.03 (m, 1H), 3.12 (d, 1H), 3.89 (s, 3H), 4.79 (d, 1H), 5.65 (d, 1H), 6.56 (d, 1H), 6.93 (d, 1H), 6.96 (t, 1H), 7.23 (d, 1H), 7.27-7.45 (m, 3H), 7.53 (d, 1H), 8.05 (d, 1H).

260 mg (0.67 mmol) [2-(2-methoxyphenyl)-2-(2-trifluoromethyloxiranyl)ethyl]-(2-methylquinolin-5-yl)amine are dissolved in 2.8 ml DMF. 436 mg (1.34 mmol) Caesium carbonate are added followed by 268 mg (2.68 mmol) 2-mercaptoimidazole. The mixture is vigorously stirred at ambient temperature for 1.5 hours. The reaction mixture is partitioned between ethyl acetate and water. The organic phase is washed with water and brine and evaporated. Flash chromatography on silica gel (acetone in hexane 0 to 65%) yields 286 mg of the title compound as a mixture of diastereomers which can be separated by preparative thin layer chromatography on silica gel (ethyl acetate).

Diastereomer 1: $^1$H-NMR (CDCl$_3$); δ=2.56 (s, 3H), 3.22 (s, 2H), 3.89 (s, 3H), 5.40 (d, 1H), 6.21 (d, 1H), 6.37 (d, 1H), 6.83 (t, 1H), 7.00 (s, 2H), 7.01-7.08 (m, 2H), 7.21 (t, 1H), 7.30 (m, 2H), 7.55 (d, 1H), 8.40 (d, 1H).

Diastereomer 2: $^1$H-NMR (CDCl$_3$); δ=2.72 (s, 3H), 3.20 (d, 1H), 3.34 (d, 1H), 3.97 (s, 3H), 5.46 (d, 1H), 6.26 (d, 1H), 6.87 (t, 1H), 6.89 (d, 1H), 6.95 (s, 2H), 7.20-7.33 (m, 4H), 7.54 (d, 1H), 8.30 (s, 1H).

Example 31

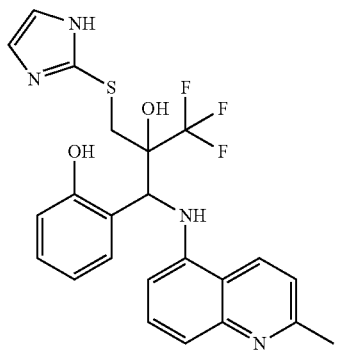

α-{[(Imidazole-2-yl)sulfanyl]methyl}-3-hydroxy-β-[(2-methylquinolin-5-yl)amino)-α-(trifluoromethyl)benzeneethanol Analogously to example 10 266 mg (0.54 mmol) β-{[(Imidazole-2-yl)sulfanyl]methyl}-3-methoxy-α-[(2-methylquinolin-5-yl)amino)-α-(trifluoromethyl)benzeneethanol in 22 ml dichloromethane are treated with 4.3 ml of a 1 M solution of boron tribromide in dichloromethane at −30° C. The typical work up after 21 hours at room temperature and chromatography on silica gel (ethyl acetate 100%) yields 78 mg and 16 mg of two diastreomers.

Diastereomer 1: $^1$H-NMR (CD$_3$OD); δ=2.65 (s, 3H), 3.35 (s, 2H), 5.44 (s, 1H), 6.41 (d, 1H), 6.72 (t, 1H), 6.79 (d, 1H) 6.93 (s, 2H), 7.05 (t, 1H), 7.15 (d, 1H), 7.32 (t, 1H), 7.34 (d, 1H), 7.41, (d, 1H), 8.41 (d, 1H).

Diastereomer 2: $^1$H-NMR (CD$_3$OD); δ=2.64 (s, 3H), 3.59 (d, 1H), 3.67 (d, 1H), 5.44 (s, 1H), 6.49 (d, 1H), 6.72 (t, 1H), 6.78 (d, 1H), 6.92 (s, 2H), 7.04 (t, 1H), 7.19 (d, 1H), 7.32 (d, 1H), 7.33 (d, 1H), 7.42 (d, 1H), 8.39 (d, 1H).

Example 32

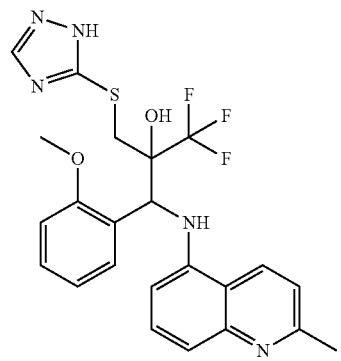

3-Methoxy-β-[(2-methylquinolin-5-yl)amino)-α-{[(1,2,4-triazol-3-yl)sulfanyl]methyl}-α-(trifluoromethyl)benzeneethanol Analogously to example 30 257 mg (0.66 mmol) {[2-methoxyphenyl][2-(trifluoromethyl)oxiranyl]methyl}-2-methylquinolin-5-amine are reacted with 3-mercapto-1,2,4-triazole under the presence of 431 mg Caesium carbonate in DMF. The typical work up after 1.5 hours and chromatography on silica gel (acetone in hexane 0-75%) yields 293 mg of the title compound as a mixture of two diastreomers. The major diastereomer can be purified by preparative thin layer chromatography on silica gel (ethyl acetate).

$^1$H-NMR (DMSO d$_6$); δ=2.56 (s, 3H), 3.22 (d, 1H), 3.49 (d, 1H), 3.86 (s, 3H), 5.48 (d, 1H), 6.30 (d, 1H), 6.33 (d, 1H), 6.84 (t, 1H), 7.00 (d, 1H), 7.07 (d, 1H), 7.21-7.35 (m, 4H), 7.56 (d, 1H), 8.46 (d, 1H).

Example 33

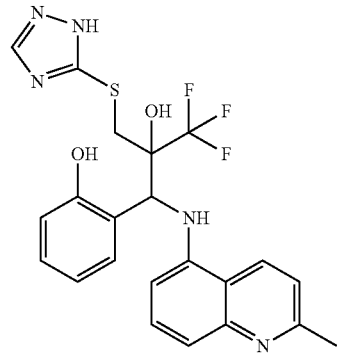

3-Hydroxy-β-[(2-methylquinolin-5-yl)amino)-α-{[(1,2,4-triazol-3-yl)sulfanyl]methyl}-α-(trifluoromethyl)benzeneethanol Analogously to example 10 271 mg (0.55 mmol) 3-methoxy-α-[(quinolin-5-yl)amino)-β-{[(1,2,4-triazol-3-yl)sulfanyl]methyl}-α-(trifluoromethyl)benzeneethanol in 22 ml dichloromethane are treated with 4.4 ml of a 1 M solution of boron tribromide in dichloromethane at −30° C. The typical work up after 22 hours at room temperature and chromatography on silica gel (methanol in dichloromethane 10%) yields 14 mg of the major diastreomer.

$^1$H-NMR (CD$_3$OD); δ=2.70 (s, 3H), 3.57 (d, 1H), 3.66 (d, 1H), 5.53 (s, 1H), 6.49 (d, 1H), 6.78 (t, 1H), 6.85 (d, 1H), 7.12 (t, 1H), 7.22 (d, 1H), 7.37 (t, 1H), 7.39 (d, 1H), 7.47 (d, 1H), 8.24 (s, 1H), 8.46 (d, 1H).

Example 34

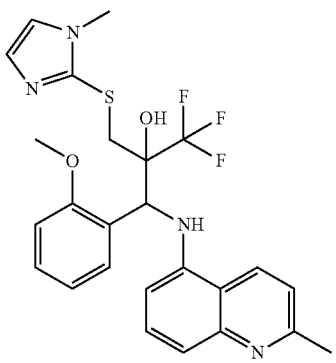

3-Methoxy-α-{[(1-Methylimidazole-2-yl)sulfanyl]methyl}-β-[(2-methylquinolin-5-yl)amino)-α-(trifluoromethyl)benzeneethanol Analogously to example 30 264 mg (0.68 mmol) {[2-methoxyphenyl][2-(trifluoromethyl)oxiranyl]methyl}-2-methylquinolin-5-amine are reacted with 310 mg (2.7 mmol) 2-mercapto-1-methylindazole under the presence of 443 mg Caesium carbonate in DMF. The typical work up after 1.5 hours and chromatography on silica gel (acetone in hexane 0-65%) yields 294 mg of the title compound as a mixture of two diastreomers which can be purified by preparative thin layer chromatography on silica gel (ethyl acetate).

Diastereomer 1: $^1$H-NMR (CDCl$_3$); δ=2.73 (s, 3H), 3.18 (d, 1H), 3.33 (d, 1H), 3.48 (s, 3H), 3.99 (s, 3H), 5.45 (d, 1H), 6.23 (d, 1H), 6.26 (d, 1H), 6.79 (s, 1H), 6.87-6.93 (m, 2H), 6.91 (s, 1H), 7.21-7.27 (m, 2H), 7.33 (m, 2H), 7.56 (d, 1H), 8.30 (d, 1H).

Diastereomer 2: $^1$H-NMR (DMSO$_6$); δ=2.62 (s, 3H), 3.57 (d, 1H), 3.46 (s, 3H), 3.82 (d, 1H), 3.94 (s, 3H), 5.48 (d, 1H), 6.16 (d, 1H), 6.32 (d, 1H), 6.81 (s, 1H), 6.80-6.93 (m, 2H), 7.01-7.11 (m, 2H), 7.21-7.33 (m, 3H), 7.56 (d, 1H), 8.31 (s, 1H), 8.45 (d, 1H).

Example 35

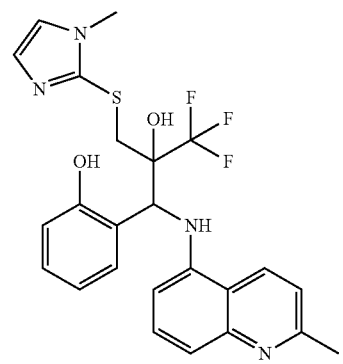

3-Hydroxy-α-{[(imidazole-211)sulfanyl]methyl}-β-[(2-methylquinolin-5-yl)amino)-α-(trifluoromethyl)benzeneethanol Analogously to example 10 271 mg (0.55 mmol) 3-methoxy-α-[(quinolin-5-yl)amino)-β-{[(1-methylindazol-2-yl)sulfanyl]methyl}-α-(trifluoromethyl)benzeneethanol in 22 ml dichloromethane are treated with 4.4 ml of a 1 M solution of boron tribromide in dichloromethane at –30° C. The typical work up after 5 hours at room temperature yields quantitatively the title compound as a mixture of two diastereomers which can be purified by preparative thin layer chromatography on silica gel (ethyl acetate).

Diastereomer 1: $^1$H-NMR (CD$_3$OD); δ=2.67 (s, 3H), 3.40 (s, 2H), 3.53 (s, 3H), 5.46 (s, 1H), 6.44 (d, 1H), 6.75 (t, 1H), 6.82 (d, 1H), 6.89 (s, 1H), 7.01 (s, 1H), 7.08 (t, 1H), 7.17 (d, 1H), 7.34 (t, 1H), 7.35 (d, 1H), 7.45 (d, 1H), 8.42 (d, 1H).

Diastereomer 2: $^1$H-NMR (CD$_3$OD); δ=2.64 (s, 3H), 3.56 (s, 3H), 3.62 (d, 1H), 3.70 (d, 1H), 5.46 (s, 1H), 6.50 (d, 1H), 6.71 (t, 1H), 6.78 (d, 1H), 6.83 (s, 1H), 6.95 (s, 1H), 7.05 (t, 1H), 7.18 (d, 1H), 7.31 (t, 1H), 7.32 (d, 1H), 7.42 (d, 1H), 8.39 (d, 1H).

Example 36

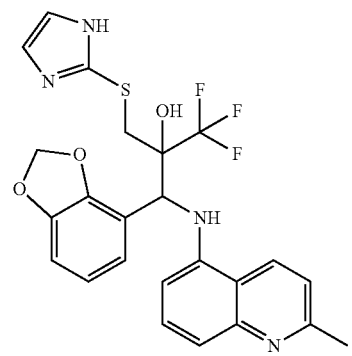

α-{[(Imidazole-2-yl)sulfanyl]methyl}-β-[(2-methylquinolin-5-yl-amino)-α-(trifluoromethyl)-1,3-benzodioxol-4-ethanol {[1,3-Benzodioxo-4-yl][2-(trifluoromethyl)oxiranyl]methyl}-2-methylquinolin-5-amine Analogously to example 9, the corresponding imine is produced starting from 1.08 g (6.8 mmol) 5-amino-2-methylquinolin and 1.02 g (6.8 mmol) 4-formyl-1,3-benzodioxol in toluene. 1.9 g [(1,3-benzodioxol-4-yl)methylene]-2-methylquinolin-5-amine in THF are added to 1.14 ml (13.2 mmol) of the lithiated 1,1,1-trifluoroepoxypropane at −100° C. analogously to example 9. Typical work up and chromatographic purification on silica gel (acetone in hexane 10% to 50%) yield 2.32 g {[1,3-benzodioxol-4-yl][2-(trifluoromethyl)oxiranyl]methyl}-2-methylquinolin-5-amine as a mixture of two diastereomers.

Diastereomer 1: $^1$H-NMR (CDCl$_3$); δ=2.73 (s, 3H), 2.79 (m, 1H), 3.17 (d, 1H), 5.09 (d, 1H), 5.44 (d, 1H), 5.97 (s, 1H), 6.03 (s, 1H), 6.49 (d, 1H), 6.77 (m, 3H), 7.27 (d, 1H), 7.41 (t, 1H), 7.44 (d, 1H), 8.18 (d, 1H).

Diastereomer 2: $^1$H-NMR (CDCl$_3$); δ=2.74 (s, 3H), 3.09 (m, 1H), 3.16 (d, 1H), 4.85 (d, 1H), 5.34 (d, 1H), 5.98 (s, 1H), 5.99 (s, 1H), 6.61 (d, 1H), 6.78 (m, 2H), 7.04 (d, 1H), 7.24 (d, 1H), 7.40 (t, 1H), 7.47 (d, 1H), 8.05 (d, 1H).

Analogously to example 30 203 mg (0.50 mmol) {[1,3-benzodioxol-4-yl][2-(trifluoromethyl)oxiranyl}methyl]-2-methylquinolin-5-amine are reacted with 202 mg (2.0 mmol) 2-mercaptoindazole under the presence of 329 mg Caesium carbonate in DMF. The typical work up after 1.5 hours and chromatography on silica gel (acetone in hexane 0-50%) yields 294 mg of the title compound as a mixture of two diastereomers. The major diastereomer can be purified by preparative thin layer chromatography on silica gel (ethyl acetate).

$^1$H-NMR (CDCl$_3$); δ=2.74 (s, 3H), 3.43 (s, 2H), 5.16 (d, 1H), 5.89 (s, 1H), 5.98 (s, 1H), 5.99 (d, 1H), 6.42 (t, 1H), 6.73 (d, 1H), 6.76 (t, 1H), 7.00 (s, 2H), 7.02 (d, 1H), 7.25 (d, 1H), 7.39 (m, 2H), 8.26 (d, 1H).

Example 37

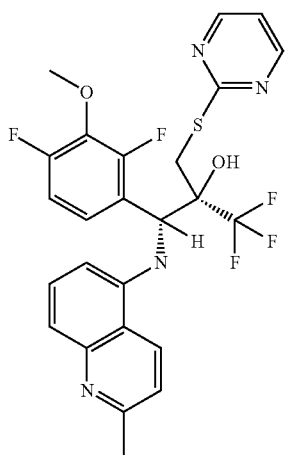

2,4-Difluoro-α-{[(pyrimidin-2-yl)sulfanyl]methyl}-3-methoxy-β-[(2-methylquinolin-5-yl)amino]-α-(trifluoromethyl)benzeneethanol Analogously to example 30 200 mg (0.47 mmol) {[2,4-difluoro-3-methoxyphenyl][2-(trifluoromethyl)oxiranyl]methyl}-2-methylquinolin-5-amine are reacted with 211 mg (1.9 mmol) 2-mercaptopyrimidine under the presence of 307 mg Caesium carbonate in DMF. The typical work up after 4 hours and chromatography on silica gel (acetone in hexane 0-50%) yields 179 mg of the title compound as a single diastreomer.

$^1$H-NMR (CD$_3$OD); δ=2.65 (s, 3H), 3.69 (d, 1H), 3.80 (d, 1H), 3.86 (s, 3H), 5.41 (s, 1H), 6.40 (d, 1H), 6.88 (dd, 1H), 7.06 (t, 1H), 7.22 (d, 1H), 7.35-7.40 (m, 3H), 8.39-8.42 (m, 3H).

Example 38

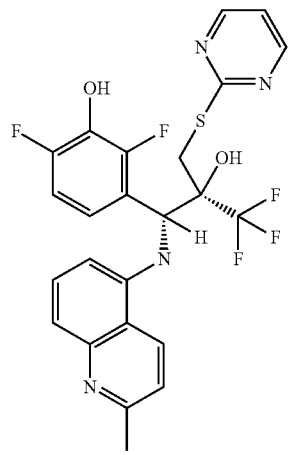

2,4-Difluoro-α-{[(pyrimidin-2-yl)sulfanyl]methyl}-3-hydroxy-β-[(2-methylquinolin-5-yl)amino]-α-(trifluoromethyl)-benzeneethanol Analogously to example 10 59 mg 2,4-Difluoro-α-{[(pyrimidin-2-yl)sulfanyl]methyl}-3-methoxy-β-[(2-methylquinolin-5-yl)amino]-α-(trifluoromethyl)-benzeneethanol in 5 ml dichloromethane are treated with 4.4 ml of a 1 M solution of boron tribromide in dichloromethane at −30° C. The typical work up after 22 hours at room temperature and chromatography on silica gel (acetone in hexane 10-50%) yields 44 mg of the desired product.

$^1$H-NMR (CD$_3$OD); δ=2.65 (s, 3H), 3.69 (d, 1H), 3.78 (d, 1H), 5.38 (s, 1H), 6.41 (d, 1H), 6.80 (dd, 1H), 7.06 (t, 1H), 7.10 (dd, 1H), 7.21 (d, 1H), 7.35 (d, 1H), 7.37 (t, 1H), 8.39 (d, 1H), 7.41 (d, 2H).

Example 39

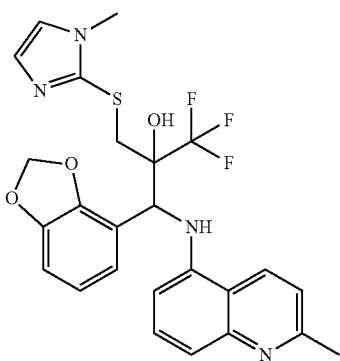

α-{[(1-Methylimidazole-2-yl)sulfanyl]methyl}-β-
[(2-methylquinolin-5-yl)amino)-α-(trifluoromethyl)-
1,3-benzodioxol-4-ethanol Analogously to example 30 206 mg (0.51 mmol) {[1,3-benzodioxol-4-yl][2-(trifluoromethyl)oxiranyl]methyl}-2-methylquinolin-5-amine are reacted with 234 mg (2.1 mmol) 2-mercapto-1-methylindazole under the presence of 334 mg Caesium carbonate in DMF. The typical work up after 1.5 hours yields 230 mg of the raw title compound as a mixture of two diastreomers. The major diastereomer can be purified by preparative thin layer chromatography on silica gel (ethyl acetate).

$^1$H-NMR (CDCl$_3$); δ=2.74 (s, 3H), 3.42 (s, 2H), 3.54 (s, 3H), 5.13 (d, 1H), 5.92 (s, 1H), 6.00 (s, 1H), 6.01 (d, 1H), 6.39 (t, 1H), 6.72 (d, 1H), 6.76 (t, 1H), 6.84 (s, 1H), 6.94 (s, 1H), 7.02 (d, 1H), 7.25 (d, 1H), 7.38 (m, 2H), 8.25 (d, 1H).

Example 40

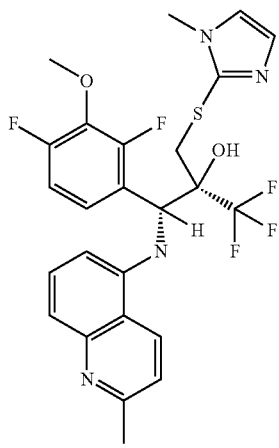

2,4-Difluoro-3-methoxy-α-{[(1-methylimidazol-2-yl)sulfanyl]methyl}-β-[(2-methylquinolin-5-yl)amino]-α-(trifluoromethyl)benzeneethanol Analogously to example 30 200 mg (0.47 mmol) {[2,4-difluoro-3-methoxyphenyl][2-(trifluoromethyl)oxiranyl]methyl}-2-methylquinolin-5-amine are reacted with 215 mg (1.9 mmol) 2-mercapto-1-methylindazole under the presence of 307 mg Caesium carbonate in DMF. The typical work up after 4 hours and chromatography on silica gel (acetone in hexane 0-50%) yields 132 mg of the title compound as a single diastreomer.

$^1$H-NMR (CD$_3$OD); δ=2.65 (s, 3H), 3.38 (d, 1H), 3.50 (d, 1H), 3.57 (s, 1H), 3.92 (s, 3H), 5.34 (s, 1H), 6.38 (d, 1H), 6.88 (dd, 1H), 6.89 (s, 1H), 7.04 (s, 1H), 7.24 (d, 1H), 7.35 (dd, 1H), 7.36 (t, 1H), 7.38 (d, 1H), 8.42 (d, 1H).

Example 41

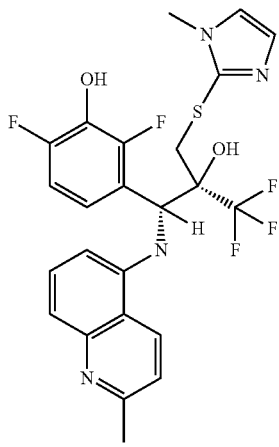

2,4-Difluoro-3-hydroxy-α-{[(1-methylimidazol-2-yl)sulfanyl]methyl}-β-[(2-methylquinolin-5-yl)amino]-α-(trifluoromethyl)benzeneethanol Analogously to example 10 39 mg 2,4-Difluoro-α-{[(1-methylimidazol-2-yl)sulfanyl]methyl}-3-methoxy-β-[(2-methylquinolin-5-yl)amino]-α-(trifluoromethyl)-benzeneethanol in 3.5 ml dichloromethane are treated with 0.7 ml of a 1 M solution of boron tribromide in dichloromethane at −10° C.

The typical work up after 22 hours at room temperature and preparative thin layer chromatography on silica gel (acetone in hexane 50%) yields 4 mg of the desired product.

¹H-NMR (CD₃OD); δ=2.66 (s, 3H), 3.35 (d, 1H), 3.45 (d, 1H), 3.58 (s, 1H), 5.30 (s, 1H), 6.38 (d, 1H), 6.80 (dd, 1H), 6.89 (s, 1H), 7.04 (s, 1H), 7.05 (dd, 1H), 7.23 (d, 1H), 7.37 (d, 1H), 7.38 (t, 1H), 8.41 (d, 1H).

Example 42

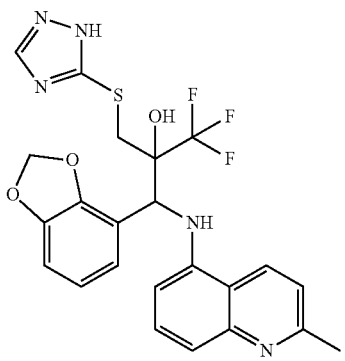

β-[(2-Methylquinolin-5-yl)amino]-α-{[(1,2,4-triazole-3-yl)sulfanyl]methyl}-α-(trifluoromethyl)-1,3-benzodioxol-4-ethanol Analogously to example 30 209 mg (0.52 mmol) {[1,3-benzodioxol-4-yl][2-(trifluoromethyl)oxiranyl]methyl}-2-methylquinolin-5-amine are reacted with 210 mg (2.1 mmol) 3-mercapto-1,2,4-triazole under the presence of 338 mg Caesium carbonate in DMF. The typical work up after 1.5 hours yields 250 mg of the raw title compound as a mixture of two diastreomers. The major diastereomer can be purified by preparative thin layer chromatography on silica gel (ethyl acetate).

¹H-NMR (DMSO d₆); δ=2.57 (s, 3H), 3.35 (d, 1H), 3.69 (d, 1H), 5.16 (d, 1H), 5.78 (s, 1H), 6.06 (s, 1H), 6.24 (d, 1H), 6.40 (d, 1H), 6.72 (t, 1H), 6.77 (d, 1H), 7.10 (d, 1H), 7.12 (d, 1H), 7.34 (t, 1H), 7.35 (d, 1H), 8.39 (s, 1H), 8.42 (d, 1H).

Example 43

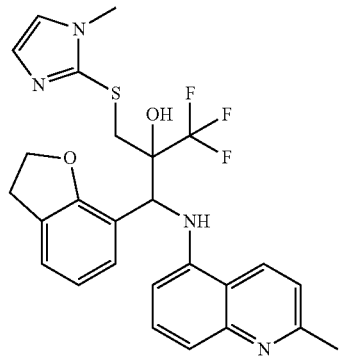

α-{[(1-Methylimidazol-2-yl)sulfanyl]methyl}-β-[(2-methylquinolin-5-yl)amino)-α-(trifluoromethyl)-1,3-benzodioxol-4-ethanol {[Benzo-2,3-dihydrofuran-7-yl][2-(trifluoromethl)oxiranyl]methyl}-2-methylquinolin-5-amine Analogously to example 9, the corresponding imine is produced starting from 1.05 g (6.6 mmol) 5-amino-2-methylquinolin and 0.98 g (6.6 mmol) 7-formylbenzo-2,3-dihdrofuran in toluene. 1.85 g (6.4 mmol) [(benzo-2,3-dihdrofuran-7-yl)methylene]-2-methylquinolin-5-amine in THF are added to 1.11 ml (13.2 mmol) of the lithiated 1,1,1-trifluoroepoxypropane at −100° C. analogously to example 9. Typical work up and chromatographic purification on silica gel (acetone in hexane 10% to 50%) yield 2.37 g {[benzo-2,3-dihydrofuran-7-yl][2-(trifluoromethyl)oxiranyl]methyl}-2-methylquinolin-5-amine as a mixture of two diastereomers.

Diastereomer 1: ¹H-NMR (CDCl₃); δ=2.70 (m, 1H), 2.72 (s, 3H), 3.12 (d, 1H), 3.24 (m, 2H), 4.63 (ddd, 1H), 4.69 (ddd, 1H), 5.21 (d, 1H), 5.50 (d, 1H), 6.48 (m, 1H), 6.76 (t, 1H), 7.00 (d, 1H), 7.14 (d, 1H), 7.26 (d, 1H), 7.41 (m, 2H), 8.18 (d, 1H).

Diastereomer 2: ¹H-NMR (CDCl₃); δ=2.73 (s, 3H), 3.08 (m, 1H), 3.12 (d, 1H), 3.22 (m, 1H), 4.58-4.72 (m, 2H), 5.06 (d, 1H), 5.36 (d, 1H), 6.62 (d, 1H), 6.85 (t, 1H), 7.16 (d, 1H), 7.24-7.29 (m, 2H), 7.46 (t, 1H), 7.48 (d, 1H), 8.06 (d, 1H).

Analogously to example 30 204 mg (0.51 mmol) {[1,3-benzo-2,3-dihydro-7-yl][2-(trifluoromethyl)oxiranyl}methyl]-2-methylquinolin-5-amine are reacted with 232 mg (2.0 mmol) 2-mercapto-1 methylindazole under the presence of 332 mg Caesium carbonate in DMF. The typical work up after 1.5 hours yields 220 mg of the raw title compound as a mixture of two diastreomers. The diastereomers can be separated by preparative thin layer chromatography on silica gel (ethyl acetate).

Diastereomer 1: ¹H-NMR (CDCl₃); δ=2.73 (s, 3H), 3.23 (t, 2H), 3.51 (s, 3H), 4.60 (ddd, 1H), 4.68 (ddd, 1H), 5.18 (d, 1H), 6.17 (d, 1H), 6.37 (d, 1H), 6.76 (t, 1H), 6.82 (s, 1H), 6.93 (s, 1H), 7.09 (d, 1H), 7.24 (d, 1H), 7.30 (d, 1H), 7.36 (m, 2H), 8.28 (d, 1H)

Diastereomer 2: ¹H-NMR (CDCl₃); δ=2.71 (s, 3H), 3.28 (t, 2H), 3.58 (s, 2H), 3.59 (s, 3H), 4.66 (ddd, 1H), 4.71 (ddd, 1H), 5.22 (br, 1H), 5.90 (br, 1H), 6.26 (m, 1H), 6.76 (t, 1H), 6.84 (s, 1H), 6.95 (s, 1H), 7.10 (d, 1H), 7.23 (d, 1H), 7.32 (m, 2H) 7.38 (d, 1H), 8.30 (d, 1H).

Example 44

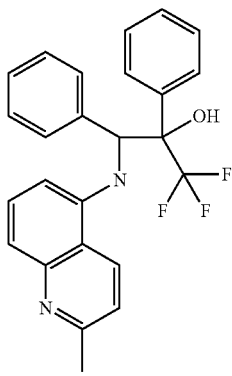

β-[(2-Methylquinolin-5-yl)amino]-α-phenyl-α-(trifluoromethyl)benzeneethanol 484 mg (2 mmol) Diethyl(phenyloxomethyl)phosphonate and 2,2,2-trifluoroacetophenone are stirred in 3 ml DMF together with 14 mg (0.22 mmol) potassium cyanide for 3 hours (Demir et al. *J. Org. Chem.* 2005, 70, 10584-87). Direct chromatographic purification on silica gel (ethyl acetate in hexane 33%) yields 580 mg phosphoric acid (1-benzoyl-2,2,2-trifluoro-1-phenylethyl)diethyl ester. 250 mg (0.6 mmol) of the phosphoric acid ester are stirred for 18 hours in 10 ml diethyl amine and 1 ml water. Evaporation and flash chromatography on silica gel (ethyl acetate in hexane 33%) yield 80 mg 3,3,3-trifluoro-2-hydroxy-1,2-diphenylpropan-1-one. 80 mg (0.29 mmol) 3,3,3-trifluoro-2-hydroxy-1,2-diphenylpropan-1-one, 0.2 ml tetra t.-butyl othotitanate and 45 mg (0.29 mmol) 5-amino-2-methylquinolin are refluxed for 18 hours in 3 ml toluene and 0.1 ml acetic acid. The reaction mixture is poured into water after cooling and filtrated through a path of cellites after stirring for 15 minutes and diluting with ethyl acetate. The phases were separated and the aqueous layer was extracted twice with ethyl acetate, the combined organic phases washed with brine, dried over sodium sulphate and then evaporated to yield 90 mg of raw β-[(2-methylquinolin-5-yl)imino]-α-phenyl-α-(trifluoromethyl)benzeneethanol. To 30 mg of the raw imine in 2 ml methanol and 0.5 ml THF are added 20 mg sodium borohydride in two portions. The mixture is stirred over 2 hours, after that period quenched by addition of acetone and saturated ammonium chloride solution and diluted with ethyl acetate. The phases are separated and the aqueous layer is extracted twice with ethyl acetate, the combined organic phases washed with brine, dried over sodium sulphate and then evaporated. Preparative thin layer chromatography on silica gel (ethyl acetate in hexane 50%) yields 2 mg of the title compound and 8 mg of the starting material.

$^1$H-NMR (CDCl$_3$); δ=2.72 (s, 3H), 5.08 (br, 1H), 5.24 (d, 1H), 6.33 (d, 1H), 7.07 (d, 1H), 7.31-7.45 (m, 8H), 7.56 (d, 2H), 7.75 (m, 3H).

Example 45

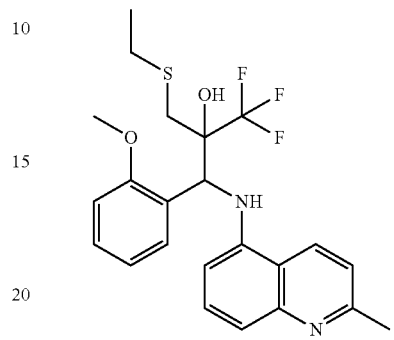

α-[(Ethylsulfanyl)methyl]-2-methoxy-β-[(2-methylchinolin-5-yl)amino]-α-(trifluoromethyl)-benzeneethanol 100 mg (0.26 mmol) {[2-methoxyphenyl][2-(trifluoromethyl)oxiranyl]methyl}-2-methylquinolin-5-amine (example 29) are dissolved in 1 ml DMF. 168 mg (0.51 mmol) Caesium carbonate are added followed by 0.26 ml of a 1M ethanethiol solution in DMF. The mixture is vigorously stirred at ambient temperature for 4 hours. The reaction mixture is partitioned between ethyl acetate and water. The organic phase is washed with water and brine and evaporated. The crude product is purified by preparative thin layer chromatography on silica gel (three 20×20 cm plates, acetone in hexane 50%). 51 mg of the title compound are obtained as a single diastereomer.

$^1$H-NMR (CD$_3$OD); δ=1.08 (t, 3H), 2.40 (dq, 2H), 2.64 (s, 3H), 2.80 (d, 1H), 2.82 (d, 1H), 3.95 (s, 3H), 5.52 (s, 1H), 6.39 (d, 1H), 6.86 (t, 1H), 7.00 (d, 1H), 7.15 (d, 1H), 7.24 (t, 1H), 7.31 (t, 1H), 7.33 (d, 1H), 7.51 (d, 1H), 8.39 (d, 1H).

Example 46

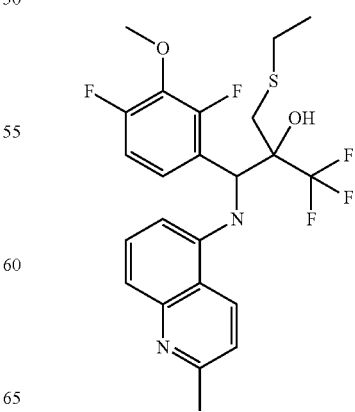

2,4-Difluoro-α-[(ethylsulfanyl)methyl]-3-methoxy-β-[(2-methylquinolin-5-yl)amino]-α-(trifluoromethyl)benzeneethanol 100 mg (0.24 mmol) {[2,4-difluoro-3-methoxyphenyl][2-(trifluoromethyl)oxiranyl]methyl}-2-methylquinolin-5-amine are dissolved in 2 ml DMF. Caesium carbonate (161 mg, 0.5 mmol) was added followed by 0.26 ml of a 1M ethanethiol solution in DMF. The mixture is vigorously stirred at ambient temperature for 2 hours. The reaction mixture was partitioned between ethyl acetate and water. The organic phase was washed with water and then with brine and evaporated. The crude product is purified by preparative thin layer chromatography on silica gel (five 20×20 cm plates, acetone in hexane 50%). 50 mg of the title compound are obtained as a single diastereomer.

$^1$H-NMR (CDCl$_3$); δ=1.15 (t, 3H), 2.42 (dq, 2H), 2.73 (s, 3H), 2.85 (d, 1H), 3.06 (d, 1H), 4.03 (s, 3H), 5.24 (d, 1H), 5.81 (d, 1H), 6.35 (d, 1H), 6.82 (dd, 1H), 7.12 (dd, 1H), 7.28 (d, 1H), 7.40 (m, 2H), 8.17 (d, 1H).

Example 47

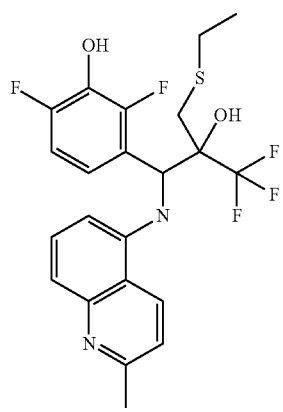

2,4-Difluoro-α-[(ethylsulfanyl)methyl]-3-hydroxy-β-[(2-methylquinolin-5-yl)amino]-α-(trifluoromethyl)benzeneethanol Analogously to example 10 40 mg (0.08 mmol) 2,4-difluoro-α-[(ethylsulfanyl)methyl]-3-methoxy-β-[(2-methylquinolin-5-yl)amino]-α-(trifluoromethyl)benzeneethanol in 1.6 ml dichloromethane are treated with 0.8 ml of a 1 M solution of boron tribromide in dichloromethane at −20° C. The typical work up after 22 hours at room temperature and chromatography on silica gel (acetone in hexane 50%) yields 26 mg of the desired product.

$^1$H-NMR (CDCl$_3$); δ=1.13 (t, 3H), 2.39 (dq, 2H), 2.74 (s, 3H), 2.82 (d, 1H), 3.06 (d, 1H), 5.20 (d, 1H), 5.82 (d, 1H), 6.35 (d, 1H), 6.79 (dd, 1H), 6.89 (dd, 1H), 7.29 (d, 1H), 7.31 (t, 1H), 7.37 (d, 1H), 8.17 (d, 1H).

Example 48

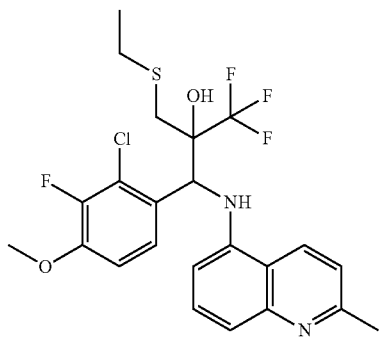

2-Chloro-3-fluoro-α-[(ethylsulfanyl)methyl]-4-methoxy-β-[(2-methylquinolin-5-yl)amino]-α-(trifluoromethyl)benzenethanol {[2-Chloro-3-fluoro-4-methoxyphenyl][2-(trifluoromethyl)oxiranyl]methyl}-2-methylquinolin-5-amine 1 g (6.2 mmol) 3-Chloro-2-fluoroanisole in 20 ml THF are cooled to −70° C. and 2.7 ml of a 2.5 M n-butyl lithium solution in hexane are added. After one hour at −70° 3.93 ml DMF in 7 ml THF are added at −70° C. and the mixture is stirred another hour at −70° C. 15 ml of a 1 M aqueous HCl are added and the reaction is warmed to ambient temperature over 18 hours. The reaction mixture is partitioned between diethyl ether and water. The aqueous phase is extracted with diethyl ether, the combined organic phases are washed with brine, dried over sodium sulfate and evaporated. The crude product is purified by chromatography on silica gel to yield 0.25 g 2-chloro-3-fluoro-4-methoxybenzaldehyde. Analogously to example 9, the corresponding imine is produced starting from 411 mg (2.6 mmol) 5-amino-2-methylquinolin and 490 mg (2.6 mmol) 2-chloro-3-fluoro-4-methoxybenzaldehyde in toluene. 800 mg (2.4 mmol) [(2-chloro-3-fluoro-4-methoxyphenyl)methylene]-2-methylquinolin-5-amine in THF are added to 0.42 ml (4.8 mmol) of the lithiated 1,1,1-trifluoroepoxypropane at −100° C. analogously to example 9. Typical work up and chromatographic purification on silica gel (acetone in hexane 0% to 50° A)) yield 796 mg and 100 mg of two diastereomers of {[2-chloro-3-fluoro-4-methoxyphenyl][2-(trifluoromethyl)oxiranyl]methyl}-2-methylquinolin-5-amine.

Diastereomer 1: 1H-NMR(CDCl3); δ=2.29 (m, 1H), 2.74 (s, 3H), 3.16 (d, 1H), 3.85 (s, 3H), 5.18 (d, 1H), 5.71 (d, 1H), 6.20 (d, 1H), 6.76 (dd, 1H), 7.00 (d, 1H), 7.31 (d, 1H), 7.36 (t, 1H), 7.43 (d, 1H), 8.22 (d, 1H).

Diastereomer 2: 1H-NMR (CDCl3); δ=2.73 (s, 3H), 3.00 (m, 1H), 3.16 (d, 1H), 3.89 (s, 3H), 4.63 (d, 1H), 5.63 (d, 1H), 6.87 (dd, 1H), 7.23 (d, 1H), 7.42 (d, 1H), 7.40 (m, 2H), 8.05 (d, 1H).

Analogously to example 45 100 mg (0.23 mmol) {[2-chloro-3-fluoro-4-methoxyphenyl][2-(trifluoromethyl)oxiranyl]methyl}-2-methylquinolin-5-amine (diastereomer 1) are reacted with 0.22 ml of the 1 M ethanthiol solution under the presence of 148 mg Caesium carbonate in DMF. The typical work up after 18 hours yields 47 mg of the raw title compound after preparative thin layer chromatography on silica gel (aceton in hexane 50° A)).

¹H-NMR (CD₃OD); δ=1.09 (t, 3H), 2.42 (dq, 2H), 2.65 (s, 3H), 2.84 (d, 1H), 2.91 (d, 1H), 3.81 (s, 3H), 5.43 (s, 1H), 6.36 (d, 1H), 6.99 (dd, 1H), 7.20 (d, 1H), 7.25 (d, 1H), 7.37 (t, 1H), 7.48 (dd, 1H), 8.39 (d, 1H).

Example 49

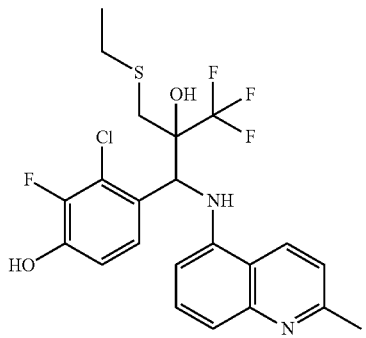

2-Chloro-3-fluoro-α-[(ethylsulfanyl)methyl]-4-hydroxy-β-[(2-methylquinolin-5-yl)amino]-α-(trifluoromethyl)benzeneethanol Analogously to example 10 100 mg (0.20 mmol) 2-Chloro-3-fluoro-α-[(ethylsulfanyl)methyl]-4-methoxy-β-[(2-methylquinolin-5-yl)amino]-α-(trifluoromethyl)benzenethanol in 8 ml dichloromethane are treated with 2 ml of a 1 M solution of boron tribromide in dichloromethane at −30° C. The typical work up after 22 hours at room temperature and chromatography on silica gel (acetone in hexane 50%) yields 26 mg of the desired product.

¹H-NMR (CD₃OD); δ=1.08 (t, 3H), 2.41 (dq, 2H), 2.65 (s, 3H), 2.82 (d, 1H), 2.90 (d, 1H), 5.38 (s, 1H), 6.37 (d, 1H), 6.79 (dd, 1H), 7.20 (d, 1H), 7.34 (dd, 1H), 7.35 (d, 1H), 7.37 (t, 1H), 8.38 (d, 1H).

Example 50

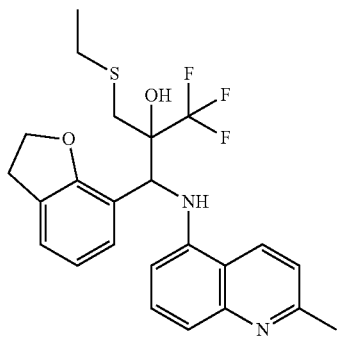

α-[(Ethylsulfanyl)methyl]-β-[(2-methylquinolin-5-yl)amino]-α-(trifluoromethyl)-2,3-dihydrobenzofuran-7-ethanol Analogously to example 45 100 mg (0.25 mmol) {[benzo-2,3-dihydrofuran-7-yl][2-(trifluoromethyl)oxiranyl]methyl}-2-methylquinolin-5-amine (example 43) are reacted with 0.24 ml of the 1 M ethanthiol solution under the presence of 162 mg Caesium carbonate in DMF. The typical work up after 18 hours yields 50 mg of the title compound after preparative thin layer chromatography on silica gel (aceton in hexane 50%).

¹H-NMR (CD₃OD); δ=1.12 (t, 3H), 2.45 (dq, 2H), 2.64 (s, 3H), 2.78 (d, 1H), 2.96 (d, 1H), 3.17 (t, 2H), 4.52 (ddd, 1H), 4.62 (ddd, 1H), 5.25 (s, 1H), 6.49 (d, 1H), 6.75 (t, 1H), 7.09 (d, 1H), 7.17 (d, 1H), 7.29 (d, 1H), 7.32 (m, 2H), 8.39 (d, 1H).

Example 51

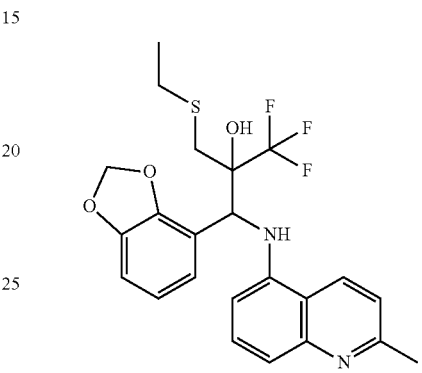

α-[(Ethylsulfanyl)methyl]-β-[(2-methylchinolin-5-yl)amino]-α-(trifluoromethyl)-1,3-benzodioxol-4-ethanol Analogously to example 45 100 mg (0.25 mmol) {[1,3-benzodioxol-4-yl][2-(trifluoromethyl)oxiranyl]methyl}-2-methylquinolin-5-amine (example 36) are reacted with 0.24 ml of the 1 M ethanthiol solution under the presence of 148 mg Caesium carbonate in DMF. The typical work up after 18 hours yields 41 mg of the title compound after preparative thin layer chromatography on silica gel (aceton in hexane 50%).

¹H-NMR (CD₃OD); δ=1.16 (t, 3H), 2.52 (q, 2H), 2.65 (s, 3H), 2.76 (d, 1H), 3.00 (d, 1H), 5.25 (s, 1H), 5.82 (s, 1H), 5.98 (s, 1H), 6.50 (d, 1H), 6.71 (d, 1H), 6.77 (t, 1H), 7.08 (d, 1H), 7.20 (d, 1H), 7.34 (d, 1H), 7.37 (t, 1H), 8.38 (d, 1H).

Example 52

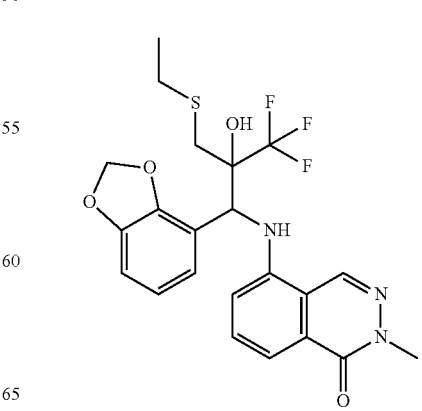

5-{[1-(1-(1,3-Benzodioxol-4-yl)-3-(ethylsulfanyl)-2-hydroxy-2-(trifluoromethyl)-propan-1-yl]amino}-2-methylphthalazin-1-on 5-({[1,3-Benzodioxo-4-yl][2-(trifluoromethl)oxiranyl]methyl}amino)-2-methylphthalazin-1-on Analogously to example 9, the corresponding imine is produced starting from 1.2 g (6.8 mmol) 5-amino-2-methylphthalazin-1-on and 1.03 g (6.8 mmol) 4-formyl-1,3-benzodioxol in toluene. 2.07 g (6.7 mmol) 5-{[(1,3-benzodioxol-4-yl)methylene]amino}-2-methylphthalazin-1-on in THF are added to 1.16 ml (13.5 mmol) of the lithiated 1,1,1-trifluoroepoxypropane at −100° C. analogously to example 9. Typical work up and chromatographic purification on silica gel (acetone in hexane 0% to 50%) yield 2.0 g 5-({[1,3-benzodioxo-4-yl][2-(trifluoromethyl)oxiranyl]methyl}amino)-2-methylphthalazin-1-on as a single diastereomer.

$^1$H-NMR (CDCl$_3$); δ=2.78 (m, 1H), 3.18 (d, 1H), 3.83 (s, 3H), 5.15 (d, 1H), 5.37 (d, 1H), 5.97 (s, 1H), 6.04 (s, 1H), 6.76 (d, 1H), 6.80 (m, 2H), 6.83 (d, 1H), 7.48 (t, 1H), 7.79 (d, 1H), 8.24 (s, 1H).

Analogously to example 45 100 mg (0.24 mmol) 5-({[1,3-benzodioxo-4-yl][2-(trifluoromethyl)oxiranyl]methyl}amino)-2-methylphthalazin-1-on are reacted with 0.24 ml of a 1 M ethanthiol solution under the presence of 155 mg Caesium carbonate in DMF. The typical work up after 18 hours yields 47 mg of the title compound after preparative thin layer chromatography on silica gel (aceton in hexane 50%).

$^1$H-NMR (CD$_3$OD); δ=1.15 (t, 3H), 2.55 (q, 2H), 2.73 (d, 1H), 2.99 (d, 1H), 3.75 (s, 3H), 5.22 (s, 1H), 5.87 (s, 1H), 6.00 (s, 1H), 6.72 (d, 1H), 6.79 (t, 1H), 6.90 (d, 1H), 7.1 (d, 1H), 7.46 (t, 1H), 7.51 (d, 1H), 8.45 (s, 1H).

Example 53

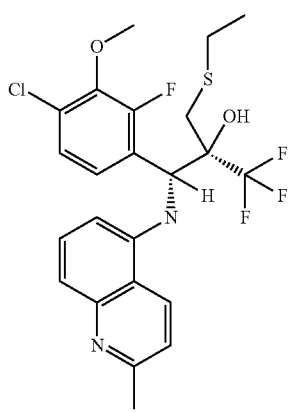

4-Chloro-2-fluoro-α-[(ethylsulfanyl)methyl]-3-methoxy-β-[(2-methylquinolin-5-yl)-amino]-α-(trifluoromethyl)benzeneethanol Analogously to example 45 100 mg (0.25 mmol) {[4-chloro-2-fluoro-3-methoxyphenyl][2-(trifluoromethyl)oxiranyl]methyl}-(2-methylquinolin-5-yl)amine (example 13) are reacted with 0.24 ml of the 1 M ethanthiol solution under the presence of 148 mg Caesium carbonate in DMF. The typical work up after 2 hours yields 54 mg of the title compound after preparative thin layer chromatography on silica gel (aceton in hexane 50%).

$^1$H-NMR (CDCl$_3$); δ=1.16 (t, 3H), 2.45 (dq, 2H), 2.73 (s, 3H), 2.86 (d, 1H), 3.07 (d, 1H), 4.00 (s, 3H), 5.26 (d, 1H), 5.83 (d, 1H), 6.33 (d, 1H), 7.07 (d, 1H), 7.12 (dd, 1H), 7.28 (d, 1H), 7.37 (t, 1H), 7.41 (d, 1H), 8.17 (d, 1H).

Example 54

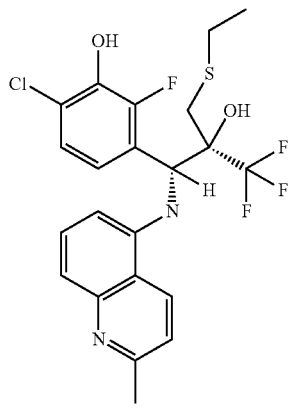

4-Chloro-2-fluoro-α-[(ethylsulfanyl)methyl]-3-hydroxy-β-[(2-methylquinolin-5-yl)amino]-α-(trifluoromethyl)benzeneethanol Analogously to example 10 44 mg (0.087 mmol) 4-chloro-2-fluoro-α-[(ethylsulfanyl)methyl]-3-methoxy-β-[(2-methylquinolin-5-yl)amino]-α-(trifluoromethyl)benzeneethanol in 1.7 ml dichloromethane are treated with 0.87 ml of a 1 M solution of boron tribromide in dichloromethane at −20° C. The typical work up after 22 hours at room temperature and chromatography on silica gel (acetone in hexane 50%) yields 30 mg of the desired product.

$^1$H-NMR (CDCl$_3$); δ=1.14 (t, 3H), 2.41 (dq, 2H), 2.73 (s, 3H), 2.82 (d, 1H), 3.05 (d, 1H), 5.21 (d, 1H), 5.83 (d, 1H), 6.33 (d, 1H), 6.93 (dd, 1H), 7.06 (d, 1H), 7.29 (d, 1H), 7.32 (t, 1H), 7.38 (d, 1H), 8.20 (d, 1H).

Example 55

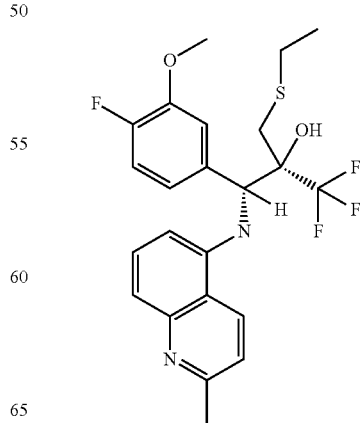

4-Fluoro-α-[(ethylsulfanyl)methyl]-3-methoxy-β-[2-methylquinolin-5-yl-amino]-α-(trifluoromethyl)benzeneethanol Analogously to example 45 100 mg (0.25 mmol) {[4-fluoro-3-methoxyphenyl][2-(trifluoromethyl)oxiranyl]methyl}-(2-methylquinolin-5-yl)amine (example 11) are reacted with 0.27 ml of the 1 M ethanthiol solution under the presence of 160 mg Caesium carbonate in DMF. The typical work up after 2 hours yields 53 mg of the title compound after preparative thin layer chromatography on silica gel (aceton in hexane 50%).

$^1$H-NMR (CDCl$_3$); δ=1.17 (t, 3H), 2.47 (q, 2H), 2.73 (s, 3H), 2.86 (d, 1H), 2.96 (d, 1H), 3.85 (s, 3H), 4.85 (d, 1H), 5.92 (d, 1H), 6.36 (d, 1H), 7.01 (m, 2H), 7.09 (d, 1H), 7.28 (d, 1H), 7.34 (t, 1H), 7.39 (d, 1H), 8.22 (d, 1H).

Example 56

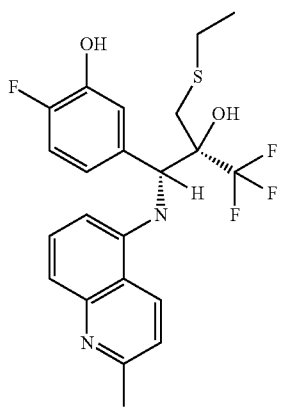

4-Fluoro-α-[(ethylsulfanyl)methyl]-3-hydroxy-β-[(2-methylquinolin-5-yl)amino]-α-(trifluoromethyl)benzeneethanol Analogously to example 10 42 mg (0.09 mmol) 4-fluoro-α-[(ethylsulfanyl)methyl]-3-methoxy-β-[(2-methylquinolin-5-yl)amino]-α-(trifluoromethyl)benzeneethanol in 1.7 ml dichloromethane are treated with 0.9 ml of a 1 M solution of boron tribromide in dichloromethane at −20° C. The typical work up after 22 hours at room temperature and chromatography on silica gel (acetone in hexane 50%) yields 28 mg of the desired product.

$^1$H-NMR (CDCl$_3$); δ=1.15 (t, 3H), 2.44 (dq, 2H), 2.64 (s, 3H), 2.87 (d, 1H), 2.95 (d, 1H), 4.76 (d, 1H), 5.78 (d, 1H), 6.26 (d, 1H), 6.92 (ddd, 1H), 7.04 (dd, 1H), 7.10 (dd, 1H), 7.15 (d, 1H), 7.22 (t, 1H), 7.27 (d, 1H), 8.07 (d, 1H).

Example 57

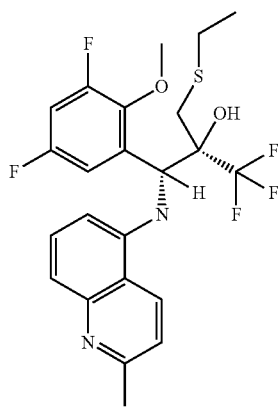

3,5-Difluoro-α-[(ethylsulfanyl)methyl]-2-methoxy-β-[(2-methylquinolin-5-yl)amino]-α-(trifluoromethyl)benzeneethanol Analogously to example 45 100 mg (0.24 mmol) {[3,5-difluoro-2-methoxyphenyl][2-(trifluoromethyl)oxiranyl]methyl}-2-methylquinolin-5-amine (example 14) are reacted with 0.25 ml of the 1 M ethanthiol solution under the presence of 148 mg Caesium carbonate in DMF. The typical work up after 2 hours yields 49 mg of the title compound after preparative thin layer chromatography on silica gel (aceton in hexane 50%).

$^1$H-NMR (CDCl$_3$); δ=1.13 (t, 3H), 2.39 (dq, 2H), 2.75 (s, 3H), 2.89 (d, 1H), 3.02 (d, 1H), 4.03 (s, 3H), 5.40 (d, 1H), 5.76 (d, 1H), 6.34 (d, 1H), 6.81 (ddd, 1H), 6.96 (dd, 1H), 7.29 (d, 1H), 7.39 (t, 1H), 7.41 (d, 1H), 8.18 (d, 1H).

Example 58

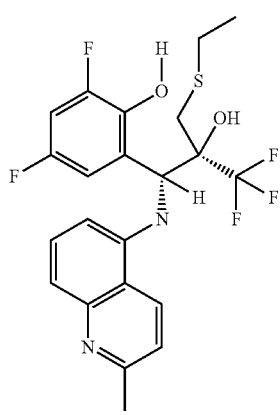

3,5-Difluoro-α-[(ethylsulfanyl)methyl]-2-hydroxy-β-[(2-methylquinolin-5-yl)amino]-α-(trifluoromethyl)-benzeneethanol Analogously to example 10 40 mg (0.20 mmol) 3,5-difluoro-α-[(ethylsulfanyl)methyl]-3-methoxy-β-[(2-methylquinolin-5-yl)amino]-α-(trifluoromethyl)benzeneethanol in 1.6 ml dichloromethane are treated with 0.82 ml of a 1 M solution of boron tribromide in dichloromethane at −20° C. The typical work up after 22 hours at room temperature and chromatography on silica gel (acetone in hexane 50%) yields 29 mg of the desired product.

$^1$H-NMR (CDCl$_3$); δ=1.13 (t, 3H), 2.31 (q, 2H), 2.36 (q, 1H), 2.81 (s, 3H), 3.11 (s, 2H), 5.62 (d, 1H), 5.82 (d, 1H), 6.61 (d, 1H), 6.69 (ddd, 1H), 6.94 (d, 1H), 7.33 (m, 1H), 7.39 (d, 1H), 7.47 (t, 1H), 8.29 (d, 1H).

Example 59

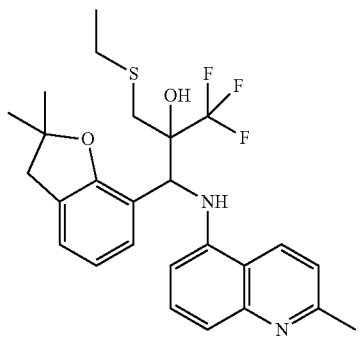

α-[(Ethylsulfanyl)methyl]-β-[(2-methylquinolin-5-yl)amino]-α-(trifluoromethyl)-2,3-dihydro-2,2-dimethylbenzofuran-7-ethanol {[2,2-Dimethylbenzo-2,3-dihydrofuran-7-yl][2-(trifluoromethyl)oxiranyl]methyl}-2-methylquinolin-5-amine Analogously to example 9, the corresponding imine is produced starting from 0.9 g (5.7 mmol) 5-amino-2-methylquinolin and 1.0 g (5.7 mmol) 7-formyl-2,3-dihdro-2,2-dimethylbenzofuran in toluene. 1.72 g (5.44 mmol) [(2,3-dihydro-2,2-dimethylbenzo-furan-7-yl)methylene]-2-methylquinolin-5-amine in THF are added to 0.94 ml (10.9 mmol) of the lithiated 1,1,1-trifluoroepoxypropane at −100° C. analogously to example 9. Typical work up and chromatographic purification on silica gel (ethyl acetate in hexane 10% to 50%) yield 1.07 g {[2,3-dihydro-2,2-dimethylbenzofuran-7-yl][2-(trifluoromethyl)oxiranyl]methyl}-2-methylquinolin-5-amine as a single diastereomer.

$^1$H-NMR (CDCl$_3$); δ=1.47 (s, 3H), 1.54 (s, 3H), 2.72 (s, 3H), 2.78 (m, 1H), 3.02 (s, 2H), 3.11 (d, 1H), 5.26 (d, 1H), 5.45 (d, 1H), 6.51 (m, 1H), 6.74 (t, 1H), 7.00 (d, 1H), 7.08 (d, 1H), 7.23 (d, 1H), 7.40 (m, 2H), 8.17 (d, 1H).

Analogously to example 45 100 mg (0.23 mmol) {[2,3-dihydro-2,2-dimethylbenzo-furan-7-yl][2-(trifluoromethyl)oxiranyl]methyl}-2-methylquinolin-5-amine are reacted with 0.26 ml of the 1 M ethanthiol solution under the presence of 152 mg Caesium carbonate in DMF. The typical work up after 2 hours yields 53 mg of the title compound after preparative thin layer chromatography on silica gel (aceton in hexane 50%).

$^1$H-NMR (CDCl$_3$); δ=1.14 (t, 3H), 1.43 (s, 3H), 1.58 (s, 3H), 2.42 (dq, 2H), 2.72 (s, 3H), 2.94 (d, 1H), 3.00 (s, 2H), 3.07 (d, 1H), 5.15 (d, 1H), 5.92 (d, 1H), 6.48 (d, 1H), 6.75 (t, 1H), 7.04 (d, 1H), 7.16 (d, 1H), 7.25 (d, 1H), 7.37 (m, 2H), 8.21 (d, 1H).

Example 60

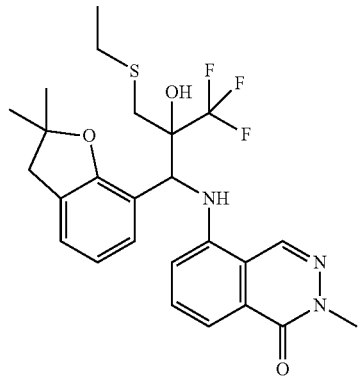

5-{[1-(2,3-Dihydro-2,2-dimethylbenzofuran-7-yl)-3-(ethylsulfanyl)-2-hydroxy-2-(trifluoromethyl)propan-1-yl]amino}-2-methylphthalazin-1-on 5-({[2,3-Dihydro-2,2-dimethylbenzofuran-7-yl][2-(trifluoromethl)oxiranyl]methyl}amino)-2-methylphthalazin-1-on Analogously to example 9, the corresponding imine is produced starting from 0.99 g (5.7 mmol) 5-amino-2-methylphthalazin-1-on and 1.0 g (5.7 mmol) 7-formyl-2,3-dihydro-2,2-dimethylbenzofuran in toluene. 1.95 g (5.7 mmol) 5-{[(2,3-dihydro-2,2-dimethylbenzofuran-7-yl)methylene]amino}-2-methylphthalazin-1-on in THF are added to 1.01 ml (11.7 mmol) of the lithiated 1,1,1-trifluoroepoxypropane at −100° C. analogously to example 9. Typical work up and chromatographic purification on silica gel (ethyl acetate in hexane 10% to 50%) yield 0.68 g 5-({[2,3-dihydro-2,2-dimethylbenzofuran-7-yl][2-(trifluoromethyl)oxiranyl]methyl}amino)-2-methylphthalazin-1-on as a single diastereomer.

$^1$H-NMR (CDCl$_3$); δ=1.47 (s, 3H), 1.53 (s, 3H), 2.72 (s, 3H), 2.78 (m, 1H), 3.01 (s, 2H), 3.11 (d, 1H), 3.82 (s, 3H), 5.36 (d, 1H), 5.41 (d, 1H), 6.79 (t, 1H), 6.88 (d, 1H), 7.02 (d, 1H), 7.11 (d, 1H), 7.48 (t, 1H), 7.75 (d, 1H), 8.21 (s, 1H).

Analogously to example 45 100 mg (0.22 mmol) 5-({[2,3-dihydro-2,2-dimethylbenzofuran-7-yl][2-(trifluoromethyl)oxiranyl]methyl}amino)-2-methylphthalazin-1-on are reacted with 0.25 ml of a 1 M ethanthiol solution under the presence of 146 mg Caesium carbonate in DMF. The typical work up after 2 hours yields 20 mg of the title compound after preparative thin layer chromatography on silica gel (isopropanol in hexane 10%).

$^1$H-NMR (CDCl$_3$); δ=1.13 (t, 3H), 1.47 (s, 3H), 1.57 (s, 3H), 2.40 (dq, 2H), 2.91 (d, 1H), 3.02 (s, 2H), 3.04 (d, 1H), 3.82 (s, 3H), 5.06 (d, 1H), 6.03 (d, 1H), 6.78 (d, 1H), 6.79 (t, 1H), 7.07 (d, 1H), 7.14 (d, 1H), 7.40 (t, 1H), 7.67 (d, 1H), 8.27 (d, 1H).

Analogously to the examples described above the following Examples can be synthesized from the corresponding amine and aromatic aldehyde via the amino trifluoromethyl oxirane, which is opened in the last step by nucleophiles like methanol, water ethanol, thiomethanol, thioethanol, isopropylthiol, diethylamine or nitrile under base catalysis.

Example 61

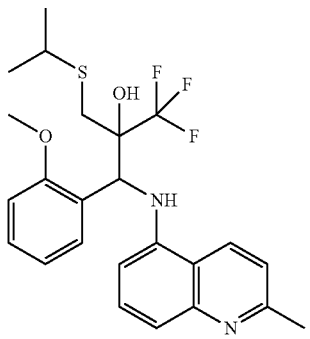

α-[(Isopropylsulfanyl)methyl]-2-methoxy-β-[(2-methylquinolin-5-yl)amino]-α-(trifluoromethyl)benzenethanol $^1$H-NMR (CDCl$_3$); δ=1.08 (d, 3H), 1.10 (d, 3H), 2.58 (m, 1H), 2.81 (s, 3H), 2.85 (d, 1H), 3.05 (d, 1H), 4.03 (s, 3H), 5.49 (d, 1H), 5.95 (d, 1H), 6.37 (d, 1H), 6.91 (dd, 1H), 6.97 (d, 1H), 7.29 (m, 2H), 7.42 (m, 3H), 8.31 (d, 1H).

Example 62

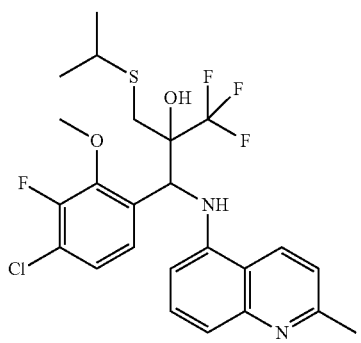

4-Chloro-3-fluoro-α-[(isopropylsulfanyl)methyl]-2-methoxy-β-[(2-methylquinolin-5-yl)amino]-α-(trifluoromethyl)benzenethanol $^1$H-NMR (CD$_3$OD); δ=1.08 (d, 3H), 1.10 (d, 3H), 2.64 (s, 3H), 2.66 (m, 1H), 2.83 (d, 1H), 2.93 (d, 1H), 3.82 (s, 3H), 3.83 (s, 3H), 5.42 (s, 1H), 6.36 (d, 1H), 6.98 (dd, 1H), 7.21 (d, 1H), 7.35 (m, 2H), 7.43 (d, 1H), 8.39 (d, 1H).

Example 63

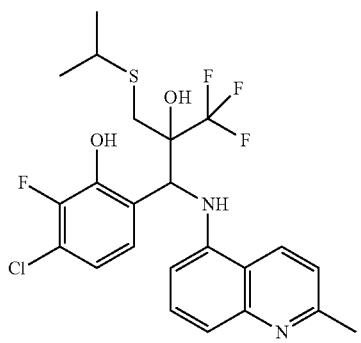

4-Chloro-3-fluoro-α-[(isopropylsulfanyl)methyl]-2-hydroxy-β-[(2-methylquinolin-5-yl)amino]-α-(trifluoromethyl)benzeneethanol $^1$H-NMR (CD$_3$OD); δ=1.08 (d, 3H), 1.10 (d, 3H), 2.64 (s, 3H), 2.66 (m, 1H), 2.83 (d, 1H), 2.93 (d, 1H), 5.45 (s, 1H), 6.50 (d, 1H), 6.74 (dd, 1H), 7.20 (d, 2H), 7.35 (d, 1H), 7.39 (t, 1H), 8.40 (d, 1H).

Example 64

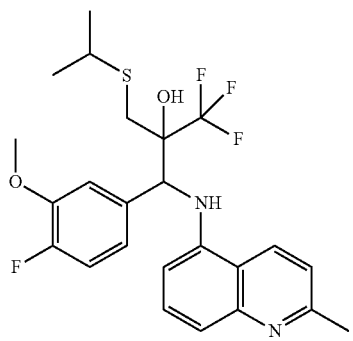

4-Fluoro-α-[(isopropylsulfanyl)methyl]-3-methoxy-β-[(2-methylquinolin-5-yl)amino]-α-(trifluoromethyl)benzeneethanol $^1$H-NMR (CDCl$_3$); δ=1.16 (d, 3H), 1.19 (d, 3H), 2.71 (s, 3H), 2.75 (m, 1H), 2.83 (d, 1H), 2.97 (d, 1H), 3.85 (s, 3H), 4.82 (d, 1H), 5.90 (d, 1H), 6.34 (dd, 1H), 6.70 (dd, 1H), 7.07 (d, 1H), 7.09 (dd, 1H), 7.27 (d, 1H), 7.35 (t, 1H), 7.37 (d, 1H), 8.21 (d, 1H).

Example 65

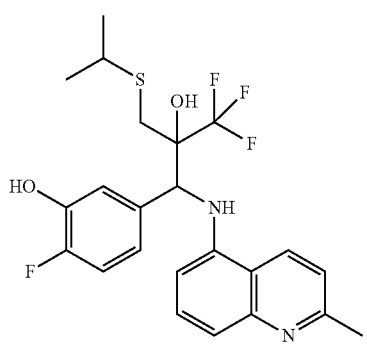

4-Fluoro-α-[(isopropylsulfanyl)methyl]-3-hydroxy-β-[(2-methylquinolin-5-yl)amino]-α-(trifluoromethyl)benzeneethanol $^1$H-NMR (CD$_3$OD); δ=1.18 (d, 3H), 1.20 (d, 3H), 2.47 (d, 1H), 2.65 (s, 3H), 2.80 (m, 1H), 2.93 (d, 1H), 4.97 (s, 1H), 6.42 (d, 1H), 6.97 (dd, 1H), 7.07 (ddd, 1H), 7.18 (d, 1H), 7.23 (dd, 1H), 7.35 (m, 2H), 8.38 (d, 1H).

Example 66

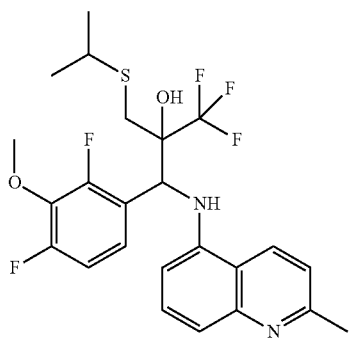

2,4-Difluoro-α-[(isopropylsulfanyl)methyl]-3-methoxy-β-[(2-methylquinolin-5-yl)amino]-α-(trifluoromethyl)-benzenethanol $^1$H-NMR (CDCl$_3$); δ=1.15 (d, 3H), 1.16 (d, 3H), 2.72 (m, 1H), 2.73 (s, 3H), 2.81 (d, 1H), 3.07 (d, 1H), 4.03 (s, 3H), 5.22 (d, 1H), 5.80 (d, 1H), 6.32 (d, 1H), 6.82 (dd, 1H), 7.10 (ddd, 1H), 7.27 (d, 1H), 7.39 (m, 2H), 8.17 (d, 1H).

Example 67

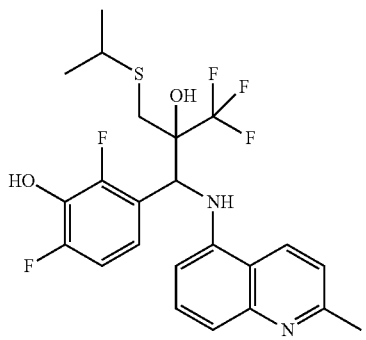

2,4-Difluoro-3-hydroxy-α-[(isopropylsulfanyl)methyl]-β-[(2-methylquinolin-5-yl)amino]-α-(trifluoromethyl)benzeneethanol $^1$H-NMR (CDCl$_3$); δ=1.14 (d, 6H), 2.67 (m, 1H), 2.73 (s, 3H), 2.80 (d, 1H), 3.07 (d, 1H), 5.19 (d, 1H), 5.79 (d, 1H), 6.34 (d, 1H), 6.79 (dd, 1H), 6.88 (ddd, 1H), 7.29 (d, 1H), 7.35 (m, 2H), 8.22 (d, 1H).

Example 68

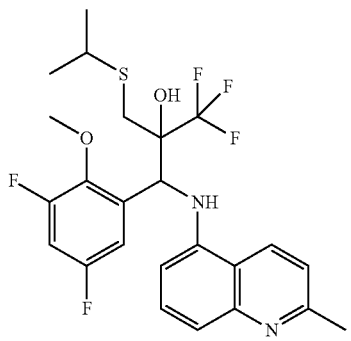

3,5-Difluoro-α-[(isopropylsulfanyl)methyl]-2-methoxy-β-[(2-methylquinolin-5-yl)amino]-α-(trifluoromethyl)-benzeneethanol $^1$H-NMR (CDCl$_3$); δ=1.14 (d, 6H), 2.64 (m, 1H), 2.82 (s, 3H), 2.84 (d, 1H), 3.02 (d, 1H), 4.11 (d, 3H), 5.38 (d, 1H), 5.83 (d, 1H), 6.36 (d, 1H), 6.82 (ddd, 1H), 6.96 (ddd, 1H), 7.33 (d, 1H), 7.44 (t, 1H), 7.62 (m, 1H), 8.29 (d, 1H).

Example 69

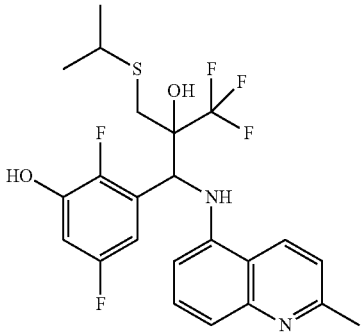

3,5-Difluoro-2-hydroxy-α-[(isopropylsulfanyl)methyl]-β-[2-methylquinolin-5-yl)amino]-α-(trifluoromethyl)benzeneethanol $^1$H-NMR (CDCl$_3$); δ=1.13 (d, 6H), 2.60 (m, 1H), 2.80 (s, 3H), 2.96 (d, 1H), 3.04 (d, 1H), 5.42 (d, 1H), 5.90 (d, 1H), 6.55 (d, 1H), 6.78 (ddd, 1H), 6.94 (dd, 1H), 7.33 (d, 1H), 7.42 (t, 1H), 7.50 (m, 1H), 8.34 (d, 1H).

Example 70

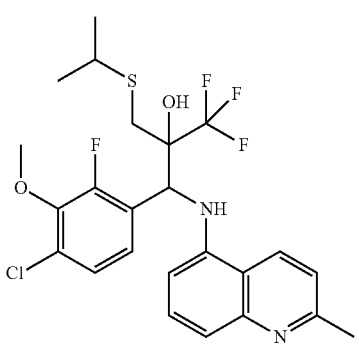

4-Chloro-2-fluoro-α-[(isopropylsulfanyl)methyl]-3-methoxy-β-[2-methylquinolin-5-yl)amino]-α-(trifluoromethyl)-benzeneethanol $^1$H-NMR (CDCl$_3$); δ=1.16 (d, 6H), 2.73 (m, 1H), 2.73 (s, 3H), 2.83 (d, 1H), 3.08 (d, 1H), 3.99 (s, 3H), 5.25 (d, 1H), 5.81 (d, 1H), 6.31 (dd, 1H), 7.10 (m, 2H), 7.28 (d, 1H), 7.39 (m, 2H), 8.17 (d, 1H).

Example 71

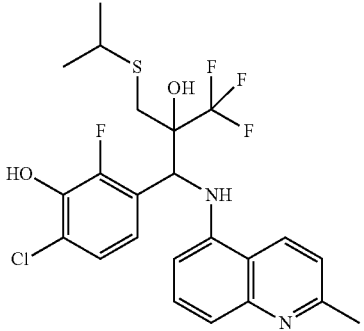

4-Chloro-2-fluoro-3-hydroxy-α-[(isopropylsulfanyl)methyl]-β-[(2-methylquinolin-5-yl)amino]-α-(trifluoromethyl)benzeneethanol ¹H-NMR (CDCl₃); δ=1.15 (d, 6H), 2.70 (m, 1H), 2.78 (s, 3H), 2.79 (d, 1H), 3.05 (d, 1H), 5.24 (d, 1H), 5.86 (d, 1H), 6.35 (d, 1H), 6.94 (dd, 1H), 7.06 (d, 1H), 7.36 (m, 2H), 7.50 (d, 1H), 8.17 (d, 1H).

Example 72

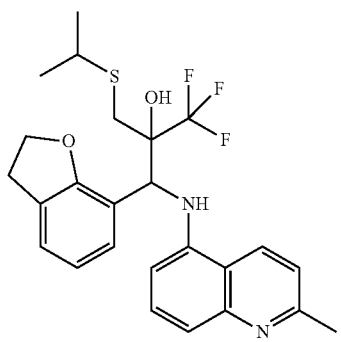

α[(Isopropylsulfanyl)methyl]-β-[(2-methylquinolin-5-yl)amino]-α-(trifluoromethyl)-2,3-dihydrobenzofuran-7-ethanol ¹H-NMR (CDCl₃); δ=1.16 (d, 6H), 2.63 (s, 3H), 2.73 (m, 1H), 2.80 (d, 1H), 2.95 (d, 1H), 3.23 (ddd, 2H), 4.64 (ddd, 2H), 5.21 (d, 1H), 5.92 (d, 1H), 6.49 (d, 1H), 6.79 (t, 1H), 7.12 (d, 1H), 7.16 (d, 1H), 7.28 (d, 1H), 7.40 (m, 2H), 8.22 (d, 1H).

Example 73

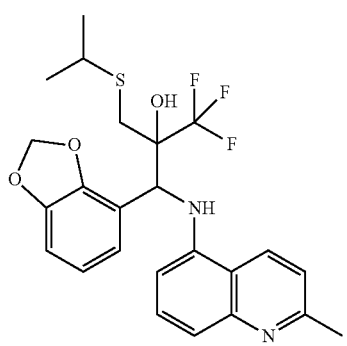

α-[(Isopropylsulfanyl)methyl]-β-[(2-methylchinolin-5-yl)amino]-α-(trifluoromethyl)-1,3-benzodioxol-4-ethanol ¹H-NMR (CD₃OD); δ=1.15 (d, 6H), 2.63 (s, 3H), 2.73 (d, 1H), 2.80 (m, 1H), 2.98 (d, 1H), 5.21 (s, 1H), 5.83 (s, 1H), 6.00 (s, 1H), 6.48 (d, 1H), 6.72 (m, 2H), 7.07 (d, 1H), 7.23 (d, 1H), 7.34 (d, 1H), 7.39 (t, 1H), 8.39 (d, 1H).

Example 74

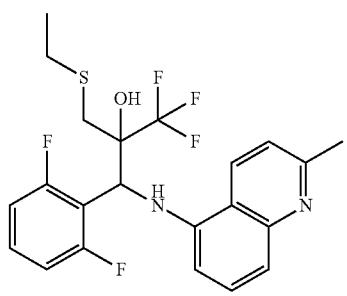

2,6-Difluoro-α-(ethylsulfanyl)methyl]-β-[(2-methylchinolin-5-yl)amino]-α-(trifluoromethyl)-benzenethanol ¹H-NMR (CDCl₃); δ=1.16 (t, 3H), 2.49 (q, 2H), 2.72 (s, 3H), 3.04 (d, 1H), 3.08 (d, 1H), 5.44 (d, 1H), 5.82 (d, 1H), 6.45 (dd, 1H), 6.78 (dd, 1H), 6.96 (t, 1H), 7.24 (dd, 1H), 7.27 (d, 1H), 7.40 (m, 2H), 8.17 (d, 1H).

Example 75

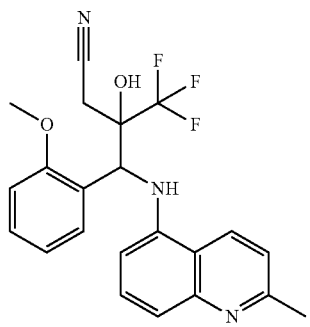

3-Hydroxy-4-(2-methoxyphenyl)-4-[(2-methylquinolin-5-yl)amino]-3-(trifluoromethyl)butyronitril 1H-NMR (CDCl₃); δ=2.71 (s, 3H), 2.83 (d, 1H), 2.89 (d, 1H), 4.00 (s, 3H), 5.41 (d, 1H), 5.94 (br, 1H), 6.53 (d, 1H), 6.97 (d, 2H), 7.26 (d, 1H), 7.35 (t, 1H), 7.42 (m, 3H), 8.30 (d, 1H).

Example 76

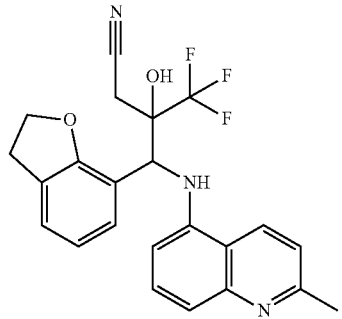

3-Hydroxy-4-(2,3-dihydrobenzofuran-7-yl)-4-[(2-methylquinolin-5-yl)amino]-3-(trifluoromethyl)butyronitril 1H-NMR (CDCl₃); δ=2.72 (s, 3H), 2.81 (d, 1H), 2.96 (d, 1H), 3.24 (ddd, 2H), 4.61 (ddd, 1H), 4.75 (ddd, 1H), 5.16 (d, 1H), 5.87 (d, 1H), 6.67 (d, 1H), 6.88 (t, 1H), 7.19 (m, 2H), 7.28 (d, 1H), 7.43 (t, 1H), 7.49 (d, 1H), 8.22 (d, 1H).

Example 77

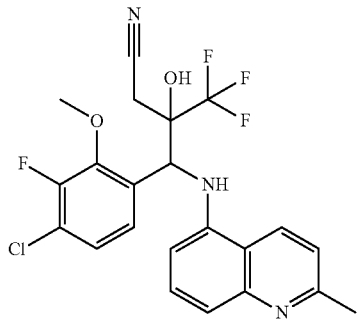

4-(4-Chloro-3-fluoro-2-methoxyphenyl-4-[(2-methylquinolin-5-yl)amino]-3-(trifluoromethyl)-7-yl-3-hydroxybutyronitril 1H-NMR (CDCl₃); δ=2.74 (s, 3H), 2.77 (d, 1H), 2.96 (d, 1H), 3.84 (s, 3H), 5.43 (d, 1H), 5.88 (d, 1H), 6.30 (d, 1H), 6.86 (t, 1H), 7.29 (d, 1H), 7.40 (m, 3H), 8.39 (d, 1H).

Example 78

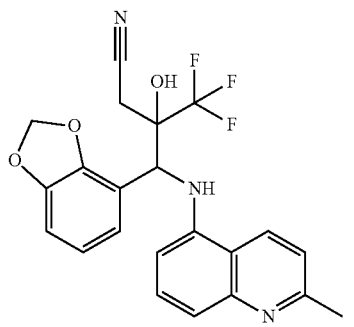

4-(1,3-Benzodioxol-4-yl)-4-[(2-methylquinolin-5-yl)amino]-3-(trifluoromethyl)-3-hydroxybutyronitril 1H-NMR (CDCl₃); δ=2.73 (s, 3H), 2.88 (d, 1H), 2.97 (d, 1H), 5.19 (d, 1H), 5.73 (d, 1H), 5.94 (s, 1H), 6.08 (s, 1H), 6.58 (d, 1H), 6.84 (m, 2H), 6.99 (d, 1H), 7.25 (d, 1H), 7.40 (t, 1H), 7.49 (d, 1H), 8.39 (d, 1H).

Example 79

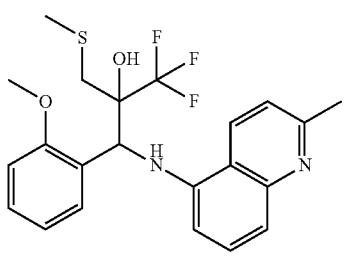

2-Methoxy-β-[(2-methylquinolin-5-yl)amino]-α-[(methylsulfanyl)methyl]-α-(trifluoromethyl)benzenethanol 1H-NMR (CDCl₃); δ=2.73 (s, 3H), 2.91 (1, 2H), 2.97 (d, 1H), 3.98 (s, 3H), 5.49 (d, 1H), 5.92 (d, 1H), 6.35 (d, 1H), 6.89 (t, 1H), 6.93 (d, 1H), 7.27 (m, 2H), 7.37 (t, 1H), 7.40 (m, 2H), 8.22 (d, 1H).

Example 80

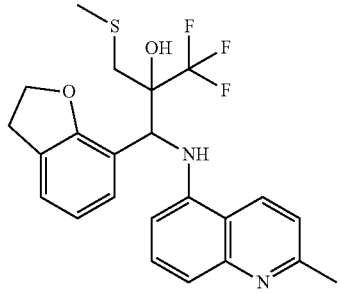

β-[(2-Methylquinolin-5-yl)amino]-α-[(methylsulfanyl)methyl]-α-(trifluoromethyl)-2,3-dihydrobenzofuran-7-ethanol ¹H-NMR (CDCl₃); δ=2.04 (s, 3H), 2.74 (s, 3H), 2.91 (d, 1H), 3.08 (d, 1H), 3.23 (ddd, 2H), 4.64 (ddd, 2H), 5.21 (d, 1H), 5.92 (d, 1H), 6.49 (d, 1H), 6.79 (t, 1H), 7.12 (d, 1H), 7.16 (d, 1H), 7.28 (d, 1H), 7.40 (m, 2H), 8.22 (d, 1H).

Example 81

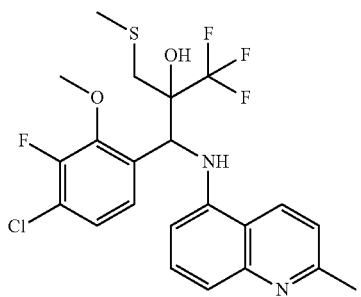

4-Chloro-3-fluoro-2-methoxy-β-[(2-methylquinolin-5-yl)amino]-α-[(methylsulfanyl)methyl]-α-(trifluoromethyl)benzenethanol ¹H-NMR (CDCl₃); δ=1.94 (s, 3H), 2.75 (d, 1H), 2.76 (s, 3H), 3.10 (d, 1H), 3.85 (s, 3H), 5.36 (d, 1H), 5.93 (d, 1H), 6.27 (dd, 1H), 6.82 (dd, 1H), 7.28 (m, 2H), 7.41 (m, 2H), 8.22 (d, 1H).

Example 82

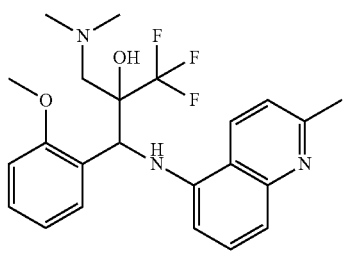

71

α-[(Dimethylamono)methyl]-2-methoxy-β-[2-methylquinolin-5-yl)amino]-α-(trifluoromethyl)benzenethanol ¹H-NMR (CDCl₃); δ=2.02 (br, 6H), 2.42 (d, 1H), 2.67 (d, 1H), 2.73 (s, 3H), 4.00 (s, 3H), 5.34 (d, 1H), 5.95 (d, 1H), 6.31 (dd, 1H), 6.86 (t, 1H), 7.23 (m, 2H), 7.33 (m, 2H), 7.50 (d, 1H), 8.24 (d, 1H).

Example 83

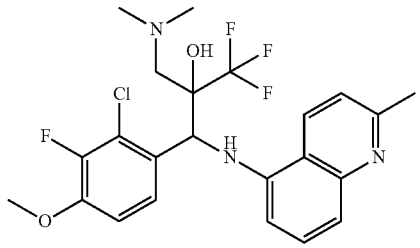

2-Chloro-α-[(dimethylamino)methyl]-3-fluoro-4-methoxy-β-[(2-methylquinolin-5-yl)amino]-α-(trifluoromethyl)benzenethanol ¹H-NMR (CDCl₃); δ=2.02 (br, 6H), 2.42 (d, 1H), 2.67 (d, 1H), 2.73 (s, 3H), 3.81 (s, 3H), 5.43 (s, 1H), 6.36 (d, 1H), 6.99 (dd, 1H), 7.20 (d, 1H), 7.25 (d, 1H), 7.37 (t, 1H), 7.48 (dd, 1H), 8.39 (d, 1H).

Example 84

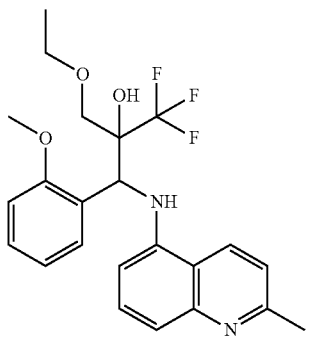

2-Methoxy-β-[(2-methylquinolin-5-yl)amino]-α-(ethoxymethyl)-α-(trifluoromethyl)benzenethanol ¹H-NMR (CDCl₃); δ=2.73 (s, 3H), 2.91 (1, 2H), 2.97 (d, 1H), 3.98 (s, 3H), 5.49 (d, 1H), 5.92 (d, 1H), 6.35 (d, 1H), 6.89 (t, 1H), 6.93 (d, 1H), 7.27 (m, 2H), 7.37 (t, 1H), 7.40 (m, 2H), 8.22 (d, 1H).

Example 85

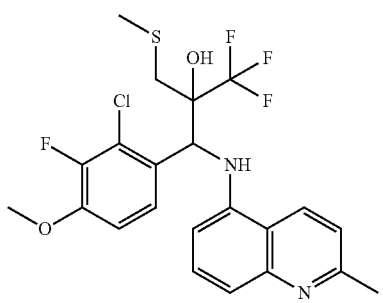

2-Chloro-3-fluoro-4-methoxy-β-[(2-methylquinolin-5-yl)amino]-α-[(methylsulfanyl)methyl]-α-(trifluoromethyl)benzenethanol ¹H-NMR (CDCl₃); δ=1.12 (t, 3H), 2.35 (dq, 2H), 2.79 (d, 1H), 2.82 (s, 3H), 3.04 (d, 1H), 3.81 (s, 3H), 5.43 (s, 1H), 6.36 (d, 1H), 6.99 (dd, 1H), 7.20 (d, 1H), 7.25 (d, 1H), 7.37 (t, 1H), 7.48 (dd, 1H), 8.39 (d, 1H).

Example 86

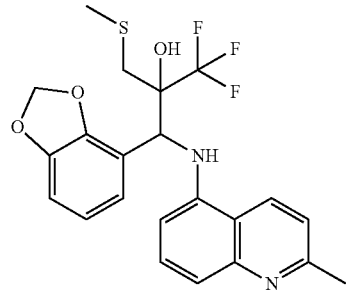

α-[(Methylsulfanyl)methyl]-β-[(2-methylchinolin-5-yl)amino]-α-(trifluoromethyl)-1,3-benzodioxol-4-ethanol ¹H-NMR (CDCl₃); δ=2.73 (s, 3H), 2.91 (1, 2H), 2.97 (d, 1H), 3.98 (s, 3H), 5.49 (d, 1H), 5.92 (d, 1H), 6.35 (d, 1H), 6.89 (t, 1H), 6.93 (d, 1H), 7.27 (m, 2H), 7.37 (t, 1H), 7.40 (m, 2H), 8.22 (d, 1H).

Example 87

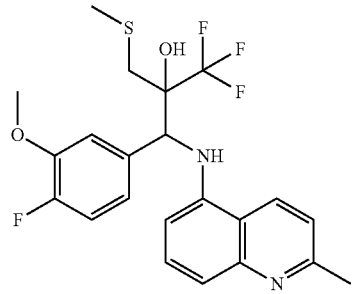

4-Fluoro-α-[(methylsulfanyl)methyl]-3-methoxy-β-[(2-methylchinolin-5-yl)amino]-α-(trifluoromethyl)benzenethanol ¹H-NMR (CDCl₃); δ=2.10 (s, 3H), 2.72 (s, 3H), 2.91 (s, 2H), 3.85 (s, 3H), 4.89 (d, 1H), 5.92 (d, 1H), 6.37 (d, 1H), 7.06 (m, 3H), 7.28 (d, 1H), 7.37 (t, 1H), 7.40 (d, 1H), 8.22 (d, 1H).

Example 88

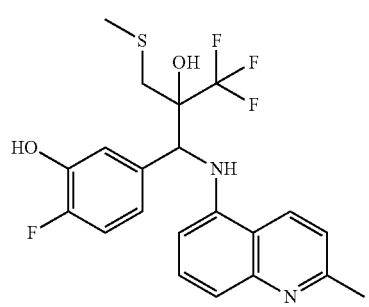

4-Fluoro-3-hydroxy-α-[(methylsulfanyl)methyl]-β-
[(2-methylchinolin-5-yl)amino]-α-(trifluoromethyl)-
benzenethanol $^{1}$H-NMR (CDCl$_{3}$); δ=2.07 (s, 3H), 2.67 (s, 3H), 2.92 (s, 2H), 4.82 (d, 1H), 5.78 (d, 1H), 6.28 (d, 1H), 6.93 (m, 1H), 7.05 (dd, 1H), 7.11 (d, 1H), 7.19 (d, 1H), 7.27 (m, 2H), 8.22 (d, 1H).

Example 89

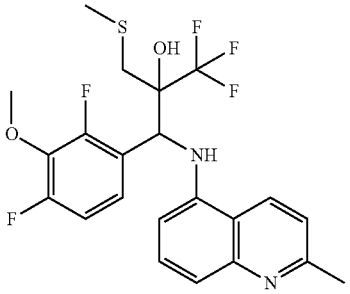

2,4-Difluoro-α-[(methylsulfanyl)methyl]-3-meth-
oxy-β-[(2-methylchinolin-5-yl)amino]-α-(trifluo-
romethyl)benzenethanol $^{1}$H-NMR (CDCl$_{3}$); δ=2.06 (s, 3H), 2.74 (s, 3H), 2.86 (d, 1H), 3.04 (d, 1H), 4.02 (s, 3H), 5.26 (d, 1H), 5.85 (d, 1H), 6.35 (d, 1H), 6.83 (ddd, 1H), 7.11 (ddd, 1H), 7.28 (d, 1H), 7.38 (t, 1H), 7.43 (d, 1H), 8.18 (d, 1H).

Example 90

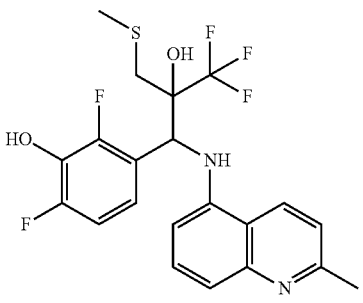

2,4-Difluoro-3-hydroxy-α-[(methylsulfanyl)methyl]-
β-[(2-methylchinolin-5-yl)amino]-α-(trifluorom-
ethyl)-benzenethanol $^{1}$H-NMR (CDCl$_{3}$); δ=2.02 (s, 3H), 2.73 (s, 3H), 2.83 (d, 1H), 3.04 (d, 1H), 5.22 (d, 1H), 5.84 (d, 1H), 6.36 (d, 1H), 6.79 (dd, 1H), 6.89 (ddd, 1H), 7.28 (d, 1H), 7.30 (t, 1H), 7.37 (d, 1H), 8.21 (d, 1H).

Example 91

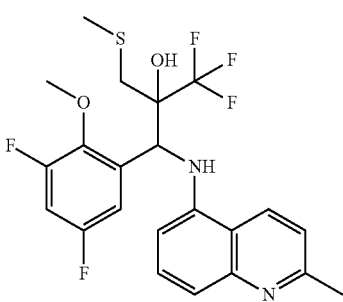

3,5-Difluoro-α-[(methylsulfanyl)methyl]-2-meth-
oxy-β-[(2-methylchinolin-5-yl)amino]-α-trifluorom-
ethyl)-benzenethanol $^{1}$H-NMR (CDCl$_{3}$); δ=2.02 (s, 3H), 2.73 (s, 3H), 2.90 (d, 1H), 3.00 (d, 1H), 4.12 (s, 3H), 5.42 (d, 1H), 5.75 (d, 1H), 6.34 (d, 1H), 6.81 (ddd, 1H), 6.97 (dd, 1H), 7.29 (d, 1H), 7.39 (m, 2H), 8.15 (d, 1H).

Example 92

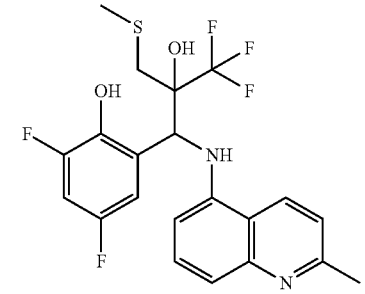

3,5-Difluoro-2-hydroxy-α-[(methylsulfanyl)methyl]-
β-[(2-methylchinolin-5-yl)amino]-α-(trifluorom-
ethyl)benzenethanol $^{1}$H-NMR (CDCl$_{3}$); δ=1.99 (s, 3H), 2.80 (s, 3H), 3.09 (s, 2H), 5.62 (d, 1H), 5.82 (d, 1H), 6.59 (d, 1H), 6.70 (ddd, 1H), 6.94 (d, 1H), 7.35 (d, 1H), 7.38 (d, 1H), 7.44 (t, 1H), 8.15 (d, 1H).

Example 93

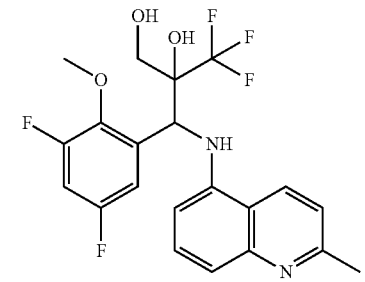

2-{(3,5-Difluoro-2-methoxyphenyl)[(2-methylquino-
lin-5-yl)amino]methyl}-3,3,3-trifluoropropane-1,2-
diol $^{1}$H-NMR (CD$_{3}$OD); δ=2.64 (s, 3H), 3.52 (d, 1H), 3.75 (d, 1H), 4.05 (s, 3H), 5.58 (s, 1H), 6.51 (d, 1H), 6.90 (ddd, 1H), 7.19 (d, 1H), 7.21 (dd, 1H), 7.33 (d, 1H), 7.39 (t, 1H), 8.35 (d, 1H).

Example 94

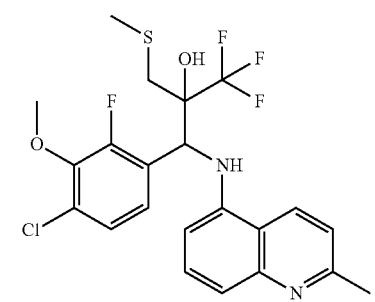

4-Chloro-2-fluoro-α-[(methylsulfanyl)methyl]-3-methoxy-β-[(2-methylquinolin-5-yl)amino]-α-(trifluoromethyl)benzenethanol ¹H-NMR (CDCl₃); δ=2.08 (s, 3H), 2.74 (s, 3H), 2.88 (d, 1H), 3.04 (d, 1H), 3.99 (s, 3H), 5.28 (d, 1H), 5.88 (d, 1H), 6.34 (d, 1H), 7.08 (d, 1H), 7.13 (dd, 1H), 7.28 (d, 1H), 7.38 (t, 1H), 7.43 (d, 1H), 8.18 (d, 1H).

Example 95

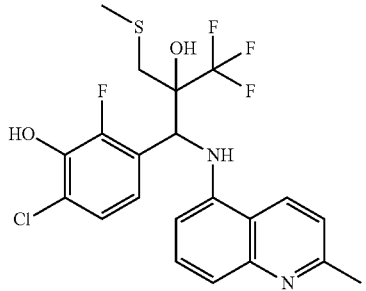

4-Chloro-2-fluoro-3-hydroxy-α-[(methylsulfanyl)methyl]-β-[(2-methylquinolin-5-yl)amino]-α-(trifluoromethyl)benzenethanol ¹H-NMR (CDCl₃); δ=2.04 (s, 3H), 2.73 (s, 3H), 2.83 (d, 1H), 3.03 (d, 1H), 5.23 (d, 1H), 5.85 (d, 1H), 6.34 (d, 1H), 6.93 (dd, 1H), 7.06 (d, 1H), 7.28 (d, 1H), 7.35 (t, 1H), 7.38 (d, 1H), 8.20 (d, 1H).

Example 96

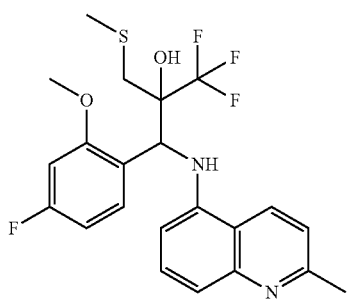

4-Fluoro-2-methoxy-β-[(2-methylquinolin-5-yl)amino]-α-[(methylsulfanyl)methyl]-α-(trifluoromethyl)benzenethanol ¹H-NMR (CDCl₃); δ=1.97 (s, 3H), 2.72 (s, 3H), 2.86 (d, 1H), 2.97 (d, 1H), 3.98 (s, 3H), 5.41 (d, 1H), 5.87 (d, 1H), 6.29 (dd, 1H), 6.60 (ddd, 1H), 6.66 (dd, 1H), 7.27 (d, 1H), 7.37 (m, 2H), 8.18 (d, 1H).

Example 97

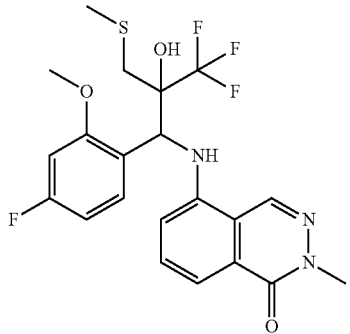

5-{[1-(4-Fluoro-2-methoxyphenyl)-3,3,3-trifluoro-2-hydroxy-2-([methylsulfanyl]methyl)propyl]amino}-2-methyl-2H-phthalazin-1-one ¹H-NMR (CDCl₃); δ=1.96 (s, 3H), 2.81 (d, 1H), 2.94 (d, 1H), 3.82 (s, 3H), 3.98 (s, 3H), 5.32 (d, 1H), 5.99 (d, 1H), 6.57 (d, 1H), 6.60 (dd, 1H), 6.66 (dd, 1H), 7.38 (m, 2H), 7.66 (d, 1H), 8.25 (s, 1H).

Example 98

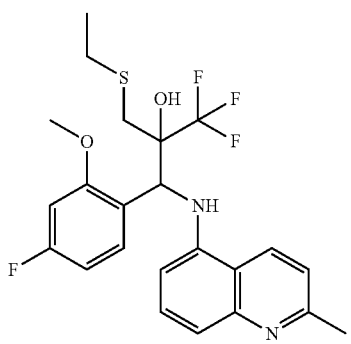

4-Fluoro-2-methoxy-β-[(2-methylquinolin-5-yl)amino]-α-[(ethylsulfanyl)methyl]-α-(trifluoromethyl)benzenethanol ¹H-NMR (CDCl₃); δ=1.10 (t, 3H), 2.33 (dq, 2H), 2.75 (s, 3H), 2.84 (d, 1H), 2.99 (d, 1H), 3.99 (s, 3H), 5.39 (d, 1H), 5.87 (d, 1H), 6.28 (d, 1H), 6.60 (ddd, 1H), 6.67 (dd, 1H), 7.29 (d, 1H), 7.40 (m, 2H), 8.22 (d, 1H).

Example 99

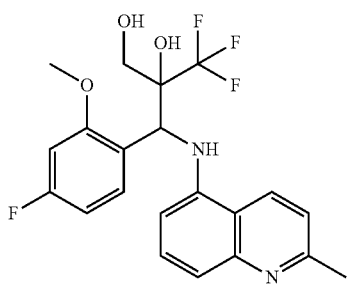

2-{(4-Fluoro-2-methoxyphenyl)[(2-methylquinolin-5-yl)amino]methyl}-3,3,3-trifluoropropane-1,2-diol $^1$H-NMR (CD$_3$OD); δ=2.63 (s, 3H), 3.58 (d, 1H), 3.67 (d, 1H), 3.95 (s, 3H), 5.49 (s, 1H), 6.34 (d, 1H), 6.59 (ddd, 1H), 6.79 (dd, 1H), 7.13 (d, 1H), 7.30 (d, 1H), 7.33 (t, 1H), 7.52 (dd, 1H), 8.35 (d, 1H).

Example 100

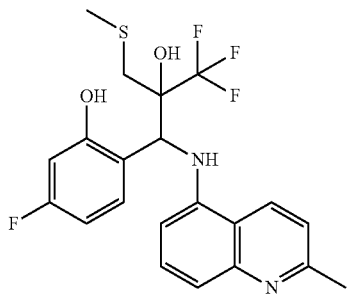

4-Fluoro-2-hydroxy-β-[(2-methylquinolin-5-yl)amino]-α-[(methylsulfanyl)methyl]-α-(trifluoromethyl)benzenethanol $^1$H-NMR (CDCl$_3$); δ=1.95 (s, 3H), 2.84 (s, 3H), 3.12 (s, 1H), 5.54 (d, 1H), 5.86 (d, 1H), 6.45 (ddd, 1H), 6.51 (dd, 1H), 6.72 (d, 1H), 7.33 (dd, 1H), 7.38 (d, 1H), 7.45 (d, 1H), 7.52 (t, 1H), 8.35 (d, 1H).

Example 101

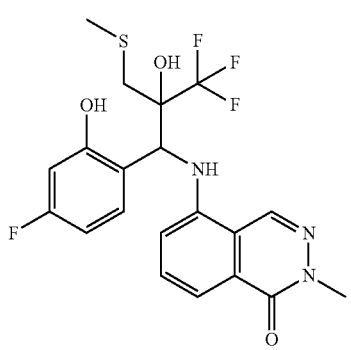

5-{[1-(4-Fluoro-2-hydroxyphenyl)-3,3,3-trifluoro-2-hydroxy-2-([methylsulfanyl]methyl)propyl]amino}-2-methyl-2H-phthalazin-1-one $^1$H-NMR (CDCl$_3$); δ=1.98 (s, 3H), 2.62 (d, 1H), 2.98 (d, 1H), 3.84 (s, 3H), 5.17 (d, 1H), 5.85 (d, 1H), 6.64 (m, 2H), 6.77 (d, 1H), 7.03 (d, 1H), 7.40 (t, 1H), 7.71 (d, 1H), 8.28 (s, 1H).

Example 102

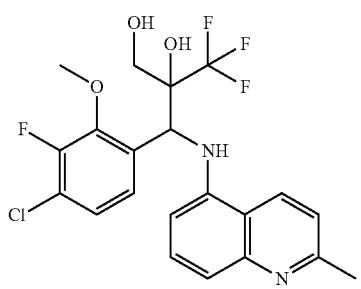

2-{(4-Chloro-3-fluoro-2-methoxyphenyl)[(2-methylquinolin-5-yl)amino]methyl}-3,3,3-trifluoropropane-1,2-diol $^1$H-NMR (CDCl$_3$); δ=2.70 (s, 3H), 3.82 (d, 1H), 3.90 (d, 1H), 4.12 (d, 3H), 5.46 (d, 1H), 6.06 (d, 1H), 6.36 (dd, 1H), 6.99 (dd, 1H), 7.20 (d, 1H), 7.21 (dd, 1H), 7.36 (m, 2H), 8.11 (d, 1H).

Example 103

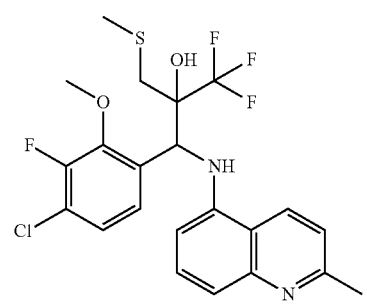

4-Chloro-3-fluoro-2-methoxy-β-[(2-methylquinolin-5-yl)amino]-α-[(methylsulfanyl)methyl]-α-(trifluoromethyl)benzenethanol $^1$H-NMR (CDCl$_3$); δ=2.04 (s, 3H), 2.73 (s, 3H), 2.90 (d, 1H), 2.98 (d, 1H), 4.16 (d, 3H), 5.39 (d, 1H), 5.83 (d, 1H), 6.33 (dd, 1H), 7.00 (dd, 1H), 7.15 (d, 1H), 7.28 (d, 1H), 7.39 (m, 2H), 8.17 (d, 1H).

Example 104

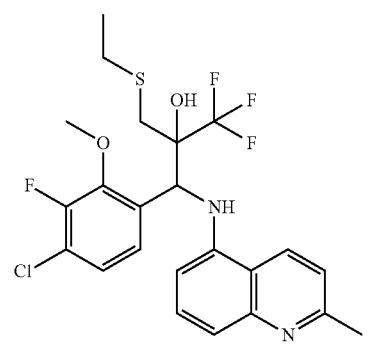

4-Chloro-3-fluoro-2-methoxy-β-[2-methylquinolin-5-yl)amino]-α-[(ethylsulfanyl)methyl]-α-(trifluoromethyl)benzenethanol $^1$H-NMR (CDCl$_3$); δ=1.15 (t, 3H), 2.41 (dq, 2H), 2.73 (s, 3H), 2.90 (d, 1H), 3.02 (d, 1H), 4.18 (d, 3H), 5.39 (d, 1H), 5.80 (d, 1H), 6.31 (dd, 1H), 7.01 (dd, 1H), 7.16 (d, 1H), 7.29 (d, 1H), 7.38 (m, 2H), 8.17 (d, 1H).

Example 105

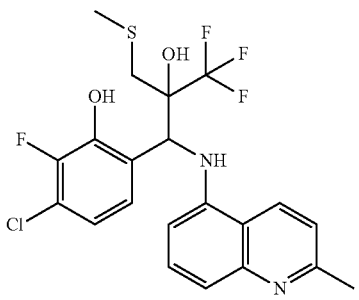

4-Chloro-3-fluoro-2-hydroxy-β-[(2-methylquinolin-5-yl)amino]-α-[(methylsulfanyl)methyl]-α-(trifluoromethyl)benzenethanol $^1$H-NMR (CDCl$_3$); δ=2.00 (s, 3H), 2.80 (s, 3H), 3.05 (d, 1H), 3.11 (d, 1H), 5.59 (br, 1H), 5.91 (br, 1H), 6.63 (d, 1H), 6.74 (dd, 1H), 7.11 (d, 1H), 7.30 (m, 1H), 7.36 (d, 1H), 7.42 (t, 1H), 8.30 (d, 1H).

Example 106

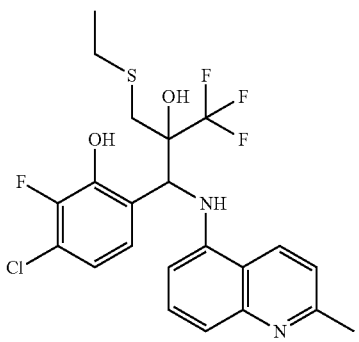

4-Chloro-α-[(ethylsulfanyl)methyl]-3-fluoro-2-hydroxy-β-[(2-methylquinolin-5-yl)amino]-α-(trifluoromethyl)benzenethanol $^1$H-NMR (CD$_3$OD); δ=1.11 (t, 3H), 2.44 (dq, 2H), 2.66 (s, 3H), 2.83 (d, 1H), 2.99 (d, 1H), 5.45 (s, 1H), 6.50 (d, 1H), 6.74 (dd, 1H), 7.20 (d, 2H), 7.35 (d, 1H), 7.39 (t, 1H), 8.40 (d, 1H).

Example 107

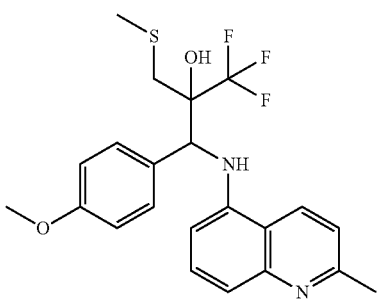

4-Methoxy-β-[(2-methylquinolin-5-yl)amino]-α-[(methylsulfanyl)methyl]-α-(trifluoromethyl)benzenethanol $^1$H-NMR (CDCl$_3$); δ=2.08 (s, 3H), 2.77 (s, 3H), 2.91 (s, 2H), 3.77 (s, 3H), 4.90 (d, 1H), 6.03 (d, 1H), 6.41 (d, 1H), 6.86 (d, 2H), 7.27 (d, 1H), 7.37 (m, 3H), 7.47 (d, 1H), 8.32 (d, 1H).

Example 108

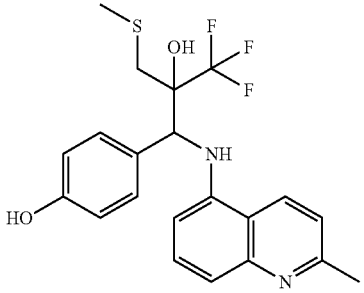

4-Hydroxy-β-[(2-methylquinolin-5-yl)amino]-α-[(methylsulfanyl)methyl]-α-(trifluoromethyl)benzenethanol $^1$H-NMR (CD$_3$OD); δ=2.08 (s, 3H), 2.45 (d, 1H), 2.64 (s, 3H), 2.90 (d, 1H), 5.02 (s, 1H), 6.42 (d, 1H), 6.71 (d, 2H), 7.16 (d, 1H), 7.34 (m, 2H), 7.40 (d, 2H), 8.40 (d, 1H).

Example 109

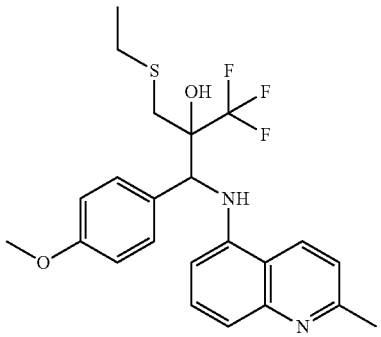

α-[(Ethylsulfanyl)methyl]-4-methoxy-β-[(2-methylquinolin-5-yl)amino]-α-(trifluoromethyl)benzenethanol $^1$H-NMR (CDCl$_3$); δ=1.15 (t, 3H), 2.45 (q, 2H), 2.76 (s, 3H), 2.87 (d, 1H), 2.96 (d, 1H), 3.77 (s, 3H), 4.86 (d, 1H), 6.02 (d, 1H), 6.40 (d, 1H), 6.86 (d, 2H), 7.12 (d, 1H), 7.38 (m, 3H), 7.46 (d, 1H), 8.34 (d, 1H).

Example 110

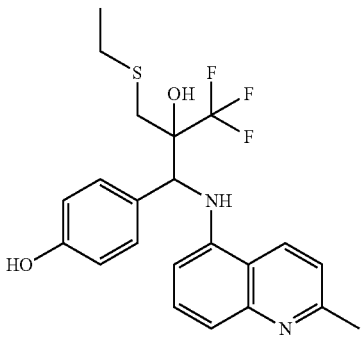

α-[(Ethylsulfanyl)methyl]-4-hydroxy-β-[(2-methylquinolin-5-yl)amino]-α-(trifluoromethyl)benzenethanol $^1$H-NMR (CD$_3$OD); δ=1.17 (t, 3H), 2.44 (d, 1H), 2.51 (q, 2H), 2.64 (s, 3H), 2.91 (d, 1H), 4.99 (s, 1H), 6.42 (d, 1H), 6.71 (d, 2H), 7.16 (d, 1H), 7.33 (m, 2H), 7.41 (d, 2H), 8.39 (d, 1H).

Example 111

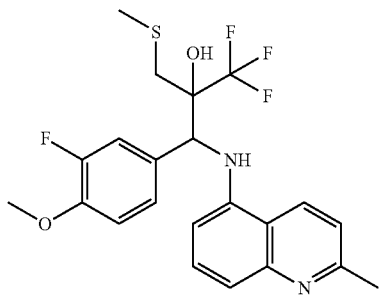

3-Fluoro-4-methoxy-β-[(2-methylquinolin-5-yl)amino]-α-[(methylsulfanyl)methyl]-α-(trifluoromethyl)benzenethanol $^1$H-NMR (CDCl$_3$); δ=2.10 (s, 3H), 2.74 (s, 3H), 2.91 (s, 2H), 3.86 (s, 3H), 4.87 (d, 1H), 5.91 (d, 1H), 6.35 (d, 1H), 6.91 (dd, 1H), 7.18 (d, 1H), 7.24 (dd, 1H), 7.27 (d, 1H), 7.34 (t, 1H), 7.47 (d, 1H), 8.32 (d, 1H).

Example 112

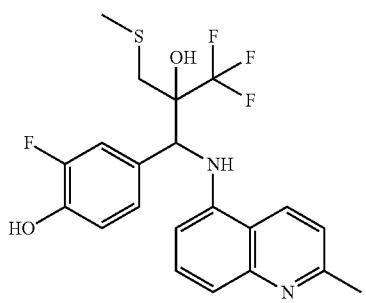

3-Fluoro-4-hydroxy-β-[(2-methylquinolin-5-yl)amino]-α-[(methylsulfanyl)methyl]-α-(trifluoromethyl)benzenethanol $^1$H-NMR (CDCl$_3$); δ=2.07 (s, 3H), 2.72 (s, 3H), 2.92 (s, 2H), 4.82 (d, 1H), 5.84 (d, 1H), 6.30 (d, 1H), 6.94 (dd, 1H), 7.07 (d, 1H), 7.15 (d, 1H), 7.29 (m, 3H), 8.21 (d, 1H).

Example 113

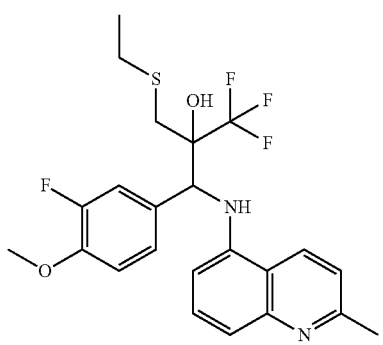

α-[(Ethylsulfanyl)methyl]-3-fluoro-4-methoxy-β-[(2-methylquinolin-5-yl)amino]-α-(trifluoromethyl)benzenethanol $^1$H-NMR (CDCl$_3$); δ=1.18 (t, 3H), 2.47 (q, 2H), 2.73 (s, 3H), 2.88 (d, 1H), 2.95 (d, 1H), 3.86 (s, 3H), 4.84 (d, 1H), 5.90 (d, 1H), 6.35 (d, 1H), 6.92 (dd, 1H), 7.21 (dd, 1H), 7.27 (m, 2H), 7.34 (t, 1H), 7.41 (d, 1H), 8.23 (d, 1H).

Example 114

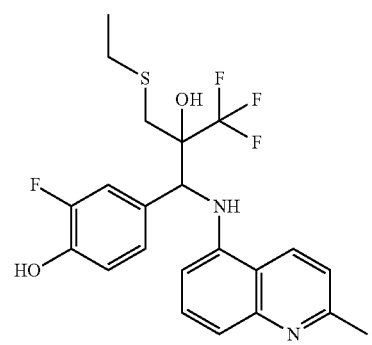

α-[(Ethylsulfanyl)methyl]-3-fluoro-4-hydroxy-β-[(2-methylquinolin-5-yl)amino]-α-(trifluoromethyl)benzenethanol $^1$H-NMR (CDCl$_3$); δ=1.16 (t, 3H), 2.45 (q, 2H), 2.72 (s, 3H), 2.87 (d, 1H), 2.96 (d, 1H), 4.79 (d, 1H), 5.86 (d, 1H), 6.30 (d, 1H), 6.95 (dd, 1H), 7.06 (d, 1H), 7.16 (d, 1H), 7.34 (m, 3H), 8.23 (d, 1H).

Example 115

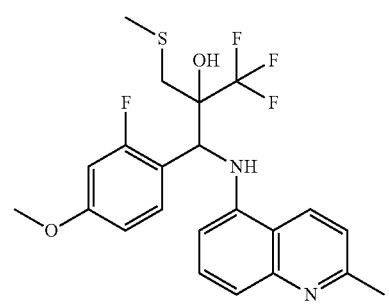

3-Fluoro-4-methoxy-β-[(2-methylquinolin-5-yl)amino]-α-[(methylsulfanyl)methyl]-α-(trifluoromethyl)benzenethanol $^1$H-NMR (CDCl$_3$); δ=2.03 (s, 3H), 2.76 (s, 3H), 2.85 (d, 1H), 3.04 (d, 1H), 3.76 (s, 3H), 5.23 (d, 1H), 5.90 (d, 1H), 6.40

(d, 1H), 6.63 (dd, 1H), 6.65 (dd, 1H), 7.29 (d, 1H), 7.34 (t, 1H), 7.41 (d, 1H), 7.46 (d, 1H), 8.32 (d, 1H).

Example 116

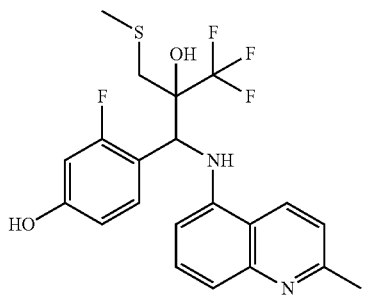

2-Fluoro-4-hydroxy-β-[(2-methylquinolin-5-yl) amino]-α-[(methylsulfanyl)methyl]-α-(trifluoromethyl)benzenethanol $^1$H-NMR (CDCl$_3$); δ=1.98 (s, 3H), 2.70 (s, 3H), 2.85 (d, 1H), 3.04 (d, 1H), 5.16 (d, 1H), 5.85 (d, 1H), 6.34 (dd, 1H), 6.52 (d, 1H), 6.63 (d, 1H), 7.17 (dd, 1H), 7.30 (m, 3H), 8.24 (d, 1H).

Example 117

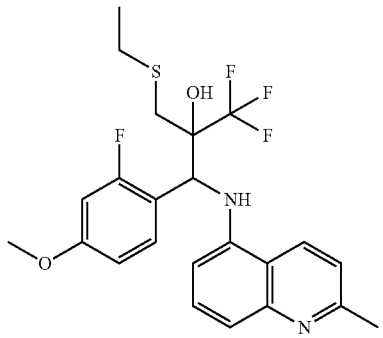

α-[(Ethylsulfanyl)methyl]-2-fluoro-4-methoxy-β-[(2-methylquinolin-5-yl)amino]-α-(trifluoromethyl) benzenethanol $^1$H-NMR (CDCl$_3$); δ=1.13 (t, 3H), 2.40 (dq, 2H), 2.75 (s, 3H), 2.84 (d, 1H), 3.06 (d, 1H), 3.76 (s, 3H), 5.23 (d, 1H), 5.86 (d, 1H), 6.37 (d, 1H), 6.62 (dd, 1H), 6.64 (dd, 1H), 7.29 (d, 1H), 7.34 (t, 1H), 7.39 (d, 1H), 7.42 (d, 1H), 8.22 (d, 1H).

Example 118

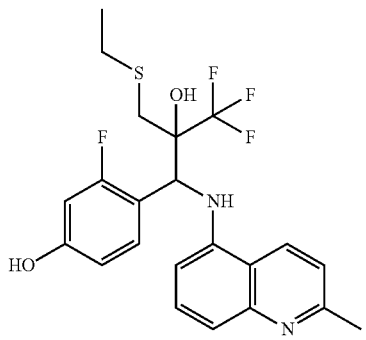

α-[(Ethylsulfanyl)methyl]-2-fluoro-4-hydroxy-β-[(2-methylquinolin-5-yl)amino]-α-(trifluoromethyl)benzenethanol $^1$H-NMR (CDCl$_3$); δ=1.16 (t, 3H), 2.44 (dq, 2H), 2.72 (s, 3H), 2.87 (d, 1H), 2.96 (d, 1H), 4.79 (d, 1H), 5.86 (d, 1H), 6.30 (d, 1H), 6.95 (dd, 1H), 7.14 (d, 1H), 7.17 (dd, 1H), 7.32 (m, 3H), 8.23 (d, 1H).

Example 119

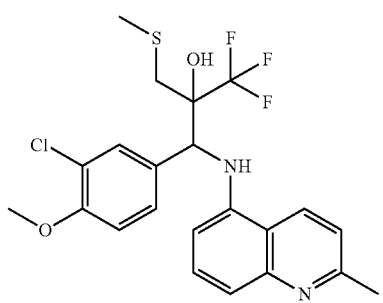

3-Chloro-4-methoxy-β-[(2-methylquinolin-5-yl)amino]-α-[(methylsulfanyl)methyl]-α-(trifluoromethyl)benzenethanol $^1$H-NMR (CDCl$_3$); δ=2.11 (s, 3H), 2.59 (s, 3H), 2.80 (d, 1H), 3.02 (d, 1H), 3.84 (s, 3H), 5.18 (d, 1H), 6.16 (d, 1H), 6.50 (d, 1H), 7.05 (d, 1H), 7.19 (d, 1H), 7.28 (d, 1H), 7.33 (t, 1H), 7.60 (dd, 1H), 7.71 (d, 1H), 8.37 (d, 1H).

Example 120

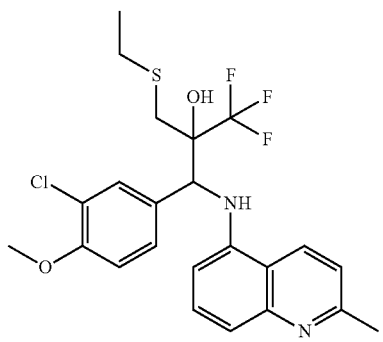

3-Chloro-α-[(ethylsulfanyl)methyl]-4-methoxy-β-[2-methylquinolin-5-yl)amino]-α-(trifluoromethyl)benzenethanol $^1$H-NMR (CDCl$_3$); δ=1.18 (t, 3H), 2.46 (q, 2H), 2.75 (s, 3H), 2.86 (d, 1H), 2.96 (d, 1H), 3.88 (s, 3H), 4.82 (d, 1H), 5.90

(d, 1H), 6.35 (d, 1H), 6.89 (d, 1H), 7.28 (d, 1H), 7.30 (d, 1H), 7.34 (t, 1H), 7.42 (d, 1H), 7.50 (s, 1H), 8.25 (d, 1H).

Example 121

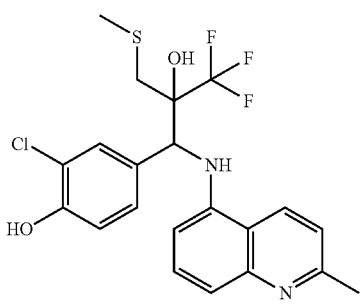

3-Chloro-4-hydroxy-β-[2-methylquinolin-5-yl)amino]-α-[(methylsulfanyl)methyl]-α-(trifluoromethyl)benzenethanol $^1$H-NMR (CD$_3$OD); δ=2.08 (s, 3H), 2.41 (d, 1H), 2.64 (s, 3H), 2.92 (d, 1H), 5.02 (s, 1H), 6.42 (d, 1H), 6.84 (d, 1H), 7.19 (d, 1H), 7.35 (m, 3H), 7.56 (d, 1H), 8.40 (d, 1H).

Example 122

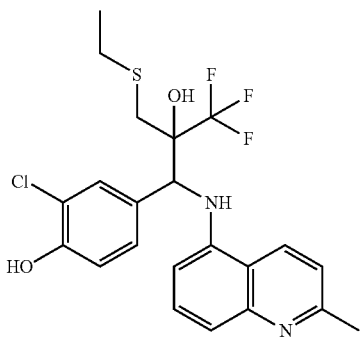

3-Chloro-α-[(ethylsulfanyl)methyl]-4-hydroxy-β-[2-methylquinolin-5-yl)amino]-α-(trifluoromethyl)benzenethanol $^1$H-NMR (CDCl$_3$); δ=1.16 (t, 3H), 2.45 (q, 2H), 2.71 (s, 3H), 2.86 (d, 1H), 2.96 (d, 1H), 4.79 (d, 1H), 5.84 (d, 1H), 6.32 (d, 1H), 6.94 (d, 1H), 7.22 (dd, 1H), 7.28 (d, 1H), 7.32 (t, 1H), 7.36 (d, 1H), 7.45 (d, 1H), 8.20 (d, 1H).

Example 123

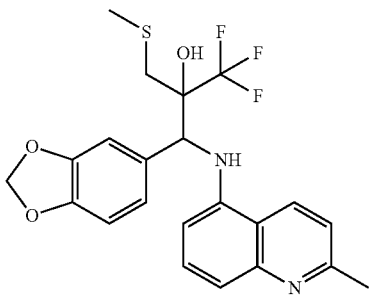

β-[(2-Methylquinolin-5-yl)amino]-α-[(methylsulfanyl)methyl]-α-(trifluoromethyl) 1,3-benzodioxol-5-ethanol $^1$H-NMR (CDCl$_3$); δ=2.10 (s, 3H), 2.73 (s, 3H), 2.94 (s, 2H), 4.85 (d, 1H), 5.88 (d, 1H), 5.91 (s, 1H), 5.95 (s, 1H), 6.41 (d, 1H), 6.77 (d, 1H), 6.93 (d, 1H), 6.95 (s, 1H), 7.28 (d, 1H), 7.35 (m, 2H), 8.21 (d, 1H).

Example 124

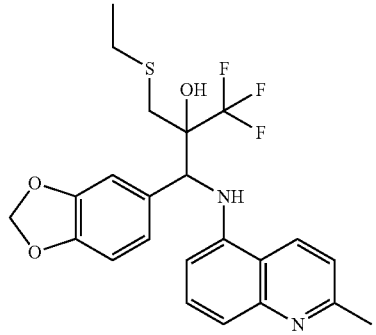

α-[(Ethylsulfanyl)methyl]-β-[(2-methylquinolin-5-yl)amino]-α-(trifluoromethyl)-1,3-benzodioxol-5-ethanol $^1$H-NMR (CDCl$_3$); δ=1.18 (t, 3H), 2.48 (q, 2H), 2.73 (s, 3H), 2.90 (d, 1H), 2.98 (d, 1H), 4.81 (d, 1H), 5.88 (d, 1H), 5.92 (s, 1H), 5.95 (s, 1H), 6.39 (d, 1H), 6.77 (d, 1H), 6.92 (d, 1H), 6.94 (s, 1H), 7.27 (d, 1H), 7.36 (m, 2H), 8.21 (d, 1H).

Example 125

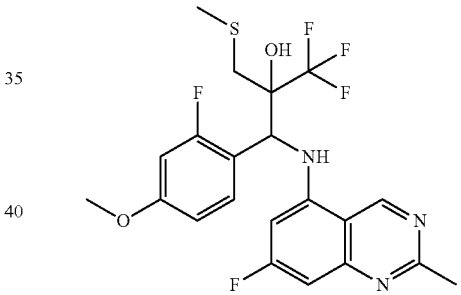

2-Fluoro-β-[(7-fluoro-2-methylquinazolin-5-yl)amino]-4-methoxy-α-[(methylsulfanyl)methyl]-α-(trifluoromethyl)benzenethanol $^1$H-NMR (CDCl$_3$); δ=1.99 (s, 3H), 2.81 (d, 1H), 2.82 (s, 3H), 3.02 (d, 1H), 3.79 (s, 3H), 5.12 (d, 1H), 6.08 (d, 1H), 6.49 (d, 1H), 6.67 (m, 2H), 6.82 (d, 1H), 7.36 (dd, 1H), 9.35 (s, 1H).

Example 126

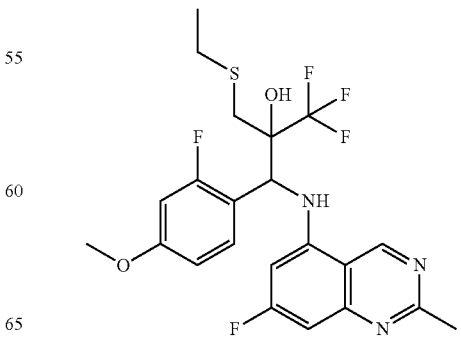

α-[(Ethylsulfanyl)methyl]-2-fluoro-β-[(7-fluoro-2-methylquinazolin-5-yl)amino]-4-methoxy-α-(trifluoromethyl)benzenethanol $^1$H-NMR (CDCl$_3$); δ=1.12 (t, 3H), 2.35 (dq, 2H), 2.79 (d, 1H), 2.82 (s, 3H), 3.04 (d, 1H), 3.79 (s, 3H), 5.10 (d, 1H), 6.08 (d, 1H), 6.43 (d, 1H), 6.68 (m, 2H), 6.81 (d, 1H), 7.36 (dd, 1H), 9.34 (s, 1H).

Example 127

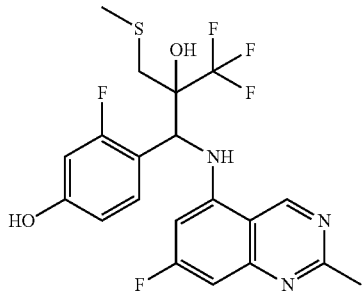

2-Fluoro-β-[(7-fluoro-2-methylquinazolin-5-yl)amino]-4-hydroxy-α-[(methylsulfanyl)methyl]-α-(trifluoromethyl)benzenethanol $^1$H-NMR (CD$_3$OD); δ=2.14 (s, 3H), 2.74 (d, 1H), 2.78 (s, 3H), 2.97 (d, 1H), 5.34 (s, 1H), 6.29 (dd, 1H), 6.59 (dd, 1H), 6.64 (dd, 1H), 6.76 (dd, 1H), 7.57 (dd, 1H), 9.52 (s, 1H).

Example 128

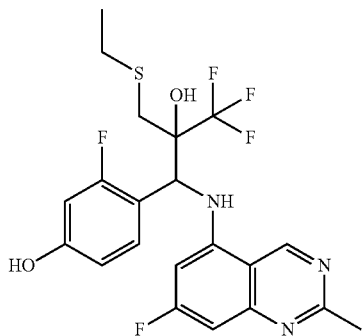

α[(Ethylsulfanyl)methyl]-2-fluoro-β-[(7-fluoro-2-methylquinazolin-5-yl)amino]-4-hydroxy-α-(trifluoromethyl)benzenethanol $^1$H-NMR (CD$_3$OD); δ=1.15 (t, 3H), 2.49 (dq, 2H), 2.69 (d, 1H), 2.72 (s, 3H), 2.92 (d, 1H), 5.26 (s, 1H), 6.23 (d, 1H), 6.53 (d, 1H), 6.59 (d, 1H), 6.69 (d, 1H), 7.52 (dd, 1H), 9.47 (s, 1H).

Example 129

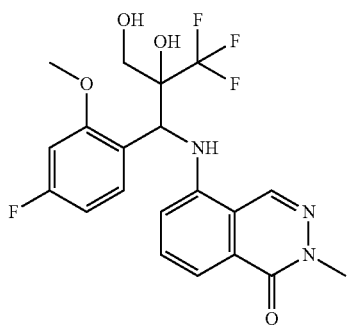

5-{[1-(4-Fluoro-2-methoxyphenyl)-3,3,3-trifluoro-2-hydroxy-2-(hydroxymethyl)propyl]amino}-2-methyl-2H-phthalazin-1-one $^1$H-NMR (CD$_3$OD); δ=3.57 (d, 1H), 3.69 (d, 1H), 3.77 (s, 3H), 3.95 (s, 3H), 5.47 (s, 1H), 6.63 (dd, 1H), 6.73 (d, 1H), 6.81 (dd, 1H), 7.43 (t, 1H), 7.47 (d, 1H), 7.57 (dd, 1H), 8.42 (s, 1H).

Example 130

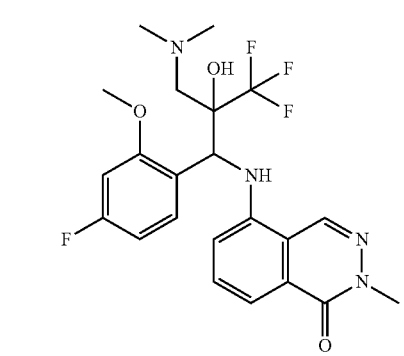

5-{[2-(1-Dimethylamino]methyl)-1-(4-fluoro-2-methoxyphenyl)-3,3,3-trifluoro-2-hydroxy-propyl]amino}-2-methyl-2H-phthalazin-1-one $^1$H-NMR (CD$_3$OD); δ=2.22 (s, 6H), 2.59 (d, 1H), 2.65 (d, 1H), 3.77 (s, 3H), 3.97 (s, 3H), 5.32 (s, 1H), 6.65 (m, 2H), 6.84 (dd, 1H), 7.42 (t, 1H), 7.46 (d, 1H), 7.54 (dd, 1H), 8.42 (s, 1H).

Example 131

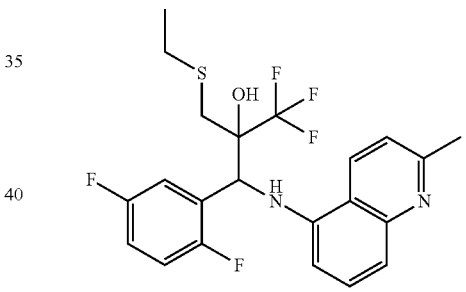

2,5-Difluoro-α-(ethylsulfanyl)methyl]-β-[(2-methyl-chinolin-5-yl)amino]-α-(trifluoromethyl)-benzenethanol $^1$H-NMR (CD$_3$OD); δ=1.19 (t, 3H), 2.55 (q, 2H), 2.70 (s, 3H), 2.79 (d, 1H), 3.01 (d, 1H), 5.47 (s, 1H), 6.50 (d, 1H), 7.09 (m, 1H), 7.18 (ddd, 1H), 7.29 (d, 1H), 7.41 (d, 1H), 7.43 (t, 1H), 7.51 (ddd, 1H), 8.46 (d, 1H).

Example 132

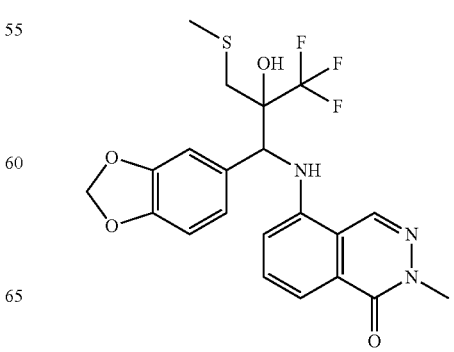

5-{[1-(1,3-Benzodioxol-5-yl)-3,3,3-trifluoro-2-hydroxy-2-([methylsulfanyl]methyl)propyl]amino}-2-methyl-2H-phthalazin-1-one ¹H-NMR (CDCl₃); δ=2.12 (s, 3H), 2.90 (s, 2H), 3.84 (s, 3H), 4.61 (s, 1H), 4.77 (d, 1H), 5.94 (s, 1H), 5.97 (s, 1H), 6.08 (d, 1H), 6.65 (d, 1H), 6.79 (d, 1H), 6.91 (d, 1H), 6.93 (s, 1H), 7.36 (t, 1H), 7.66 (d, 1H), 8.28 (s, 1H).

Example 133

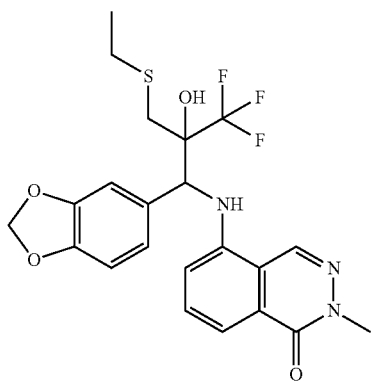

5-{[1-(1,3-Benzodioxol-5-yl)-2-([ethylsulfanyl]methyl)-3,3,3-trifluoro-2-hydroxypropyl]amino}-2-methyl-2H-phthalazin-1-one ¹H-NMR (CDCl₃); δ=1.19 (t, 3H), 2.48 (q, 2H), 2.87 (d, 1H), 2.95 (d, 1H), 3.84 (s, 3H), 4.46 (s, 1H), 4.73 (d, 1H), 5.94 (s, 1H), 5.97 (s, 1H), 6.00 (d, 1H), 6.67 (d, 1H), 6.79 (d, 1H), 6.92 (d, 1H), 6.93 (s, 1H), 7.38 (t, 1H), 7.69 (d, 1H), 8.28 (s, 1H).

Example 134

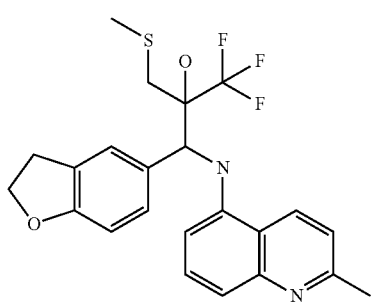

β-[(2-Methylquinolin-5-yl)amino]-α-[(methylsulfanyl)methyl]-α-(trifluoromethyl)-2,3-dihydrobenzofuran-5-ethanol ¹H-NMR (CDCl₃); δ=2.09 (s, 3H), 2.73 (s, 3H), 2.93 (s, 2H), 3.17 (ddd, 2H), 4.55 (ddd, 2H), 4.87 (br, 1H), 5.93 (br, 1H), 6.41 (d, 1H), 6.73 (d, 1H), 7.19 (d, 1H), 7.28 (d, 1H), 7.35 (m, 2H), 7.40 (d, 1H), 8.22 (d, 1H).

Example 135

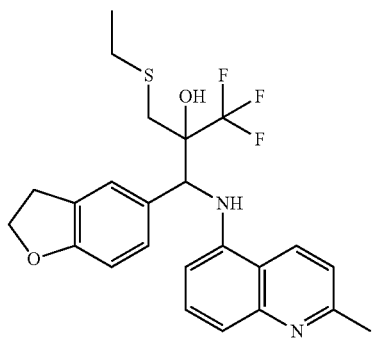

α-[(Ethylsulfanyl)methyl]-β-[(2-methylquinolin-5-yl)amino]-α-(trifluoromethyl)-2,3-dihydrobenzofuran-5-ethanol ¹H-NMR (CDCl₃); δ=1.17 (t, 3H), 2.46 (q, 2H), 2.75 (s, 3H), 2.89 (d, 1H), 2.96 (d, 1H), 3.17 (ddd, 2H), 4.55 (ddd, 2H), 4.83 (s, 1H), 5.95 (br, 1H), 6.40 (d, 1H), 6.73 (d, 1H), 7.19 (d, 1H), 7.28 (d, 1H), 7.35 (m, 2H), 7.42 (d, 1H), 8.25 (d, 1H).

Example 136

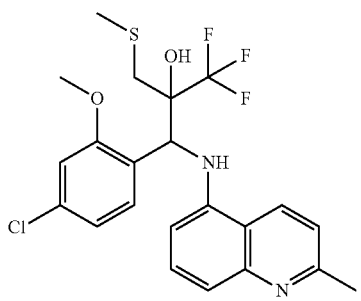

4-Chloro-2-methoxy-β-[(2-methylquinolin-5-yl)amino]-α-[(methylsulfanyl)methyl]-α-(trifluoromethyl)benzenethanol ¹H-NMR (CD₃OD); δ=2.04 (s, 3H), 2.64 (s, 3H), 2.75 (d, 1H), 2.81 (d, 1H), 3.95 (s, 3H), 5.49 (s, 1H), 6.35 (d, 1H), 6.86 (dd, 1H), 7.03 (d, 1H), 7.17 (d, 1H), 7.34 (m, 2H), 7.49 (d, 1H), 8.38 (d, 1H).

Example 137

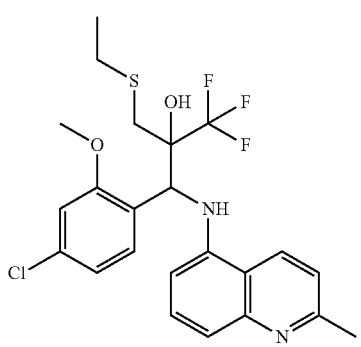

4-Chloro-α-[(ethylsulfanyl)methyl]-2-methoxy-β-[(2-methylquinolin-5-yl)amino]-α-(trifluoromethyl)benzenethanol ¹H-NMR (CD₃OD); δ=1.11 (t, 3H), 2.44 (q, 2H), 2.64 (s, 3H), 2.80 (s, 2H), 3.96 (s, 3H), 5.47 (s, 1H), 6.35 (d, 1H), 6.87 (dd, 1H), 7.04 (d, 1H), 7.17 (d, 1H), 7.35 (m, 2H), 7.50 (d, 1H), 8.38 (d, 1H).

Example 138

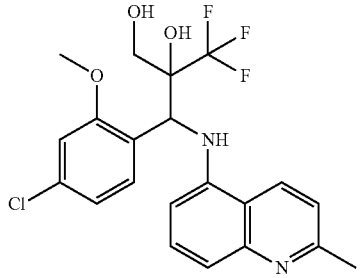

2-{(4-Chloro-2-methoxyphenyl)[(2-methylquinolin-5-yl)amino]methyl}-3,3,3-trifluoropropane-1,2-diol ¹H-NMR (CD₃OD); δ=2.64 (s, 3H), 3.59 (d, 1H), 3.67 (d, 1H), 3.96 (s, 3H), 5.50 (s, 1H), 6.33 (d, 1H), 6.86 (d, 1H), 7.03 (d, 1H), 7.15 (d, 1H), 7.34 (m, 2H), 7.50 (d, 1H), 8.34 (d, 1H).

Example 139

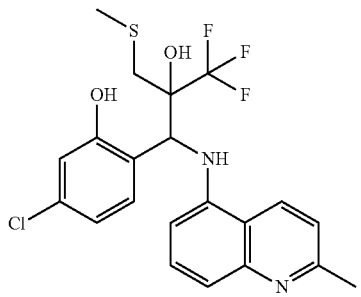

4-Chloro-2-hydroxy-β-[(2-methylquinolin-5-yl)amino]-α-[(methylsulfanyl)methyl]-α-(trifluoromethyl)benzenethanol ¹H-NMR (CD₃OD); δ=2.02 (s, 3H), 2.66 (s, 3H), 2.85 (d, 1H), 2.94 (d, 1H), 5.44 (s, 1H), 6.49 (d, 1H), 6.73 (d, 1H), 6.82 (s, 1H), 7.19 (d, 1H), 7.34 (m, 2H), 7.40 (t, 1H), 8.39 (d, 1H).

Example 140

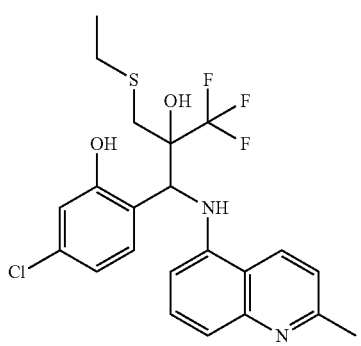

4-Chloro-α-[(ethylsulfanyl)methyl]-2-hydroxy-β-[(2-methylquinolin-5-yl)amino]-α-(trifluoromethyl)benzenethanol ¹H-NMR (CD₃OD); δ=1.14 (t, 3H), 2.45 (dq, 2H), 2.69 (s, 3H), 2.90 (d, 1H), 3.00 (d, 1H), 5.45 (s, 1H), 6.54 (d, 1H), 6.74 (dd, 1H), 6.85 (d, 1H), 7.23 (d, 1H), 7.40 (m, 3H), 8.43 (d, 1H).

Example 141

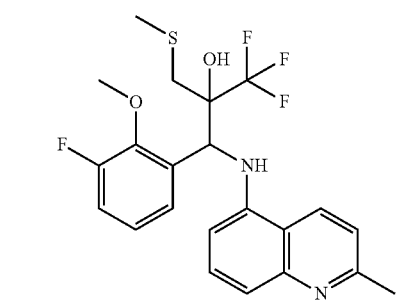

3-Fluoro-2-methoxy-β-[(2-methylquinolin-5-yl)amino]-α-[(methylsulfanyl)methyl]-α-(trifluoromethyl)benzenethanol ¹H-NMR (CD₃OD); δ=2.14 (s, 3H), 2.70 (s, 3H), 3.18 (d, 1H), 3.27 (d, 1H), 4.08 (d, 3H), 5.77 (s, 1H), 6.72 (d, 1H), 6.96 (ddd, 1H), 7.03 (ddd, 1H), 7.28 (d, 1H), 7.40 (d, 1H), 7.45 (m, 2H), 8.48 (d, 1H).

Example 142

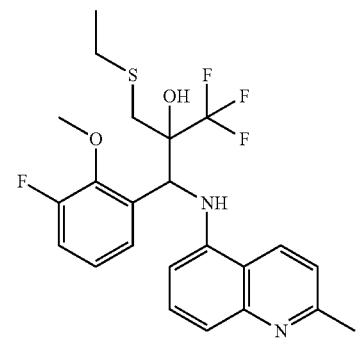

α-[(Ethylsulfanyl)methyl]-3-fluoro-2-methoxy-β-[(2-methylquinolin-5-yl)amino]-α-(trifluoromethyl)benzenethanol ¹H-NMR (CD₃OD); δ=1.17 (t, 3H), 2.56 (dq, 2H), 2.70 (s, 3H), 3.21 (d, 1H), 3.29 (d, 1H), 4.08 (d, 3H), 5.77 (s, 1H), 6.73

(d, 1H), 6.96 (ddd, 1H), 7.04 (ddd, 1H), 7.28 (d, 1H), 7.40 (d, 1H), 7.45 (m, 2H), 8.49 (d, 1H).

Example 143

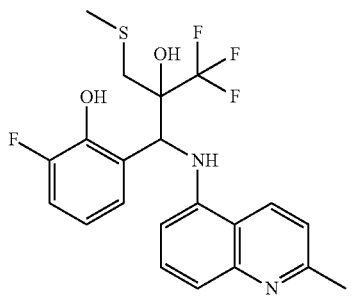

3-Fluoro-2-hydroxy-β-[(2-methylquinolin-5-yl)amino]-α-[(methylsulfanyl)methyl]-α-(trifluoromethyl)benzenethanol ¹H-NMR (CDCl₃); δ=2.02 (s, 3H), 2.75 (s, 3H), 3.08 (s, 2H), 5.52 (br, 1H), 5.92 (br, 1H), 6.59 (d, 1H), 6.78 (ddd, 1H), 7.01 (dd, 1H), 7.21 (d, 1H), 7.38 (m, 2H), 7.40 (t, 1H), 8.26 (d, 1H).

Example 144

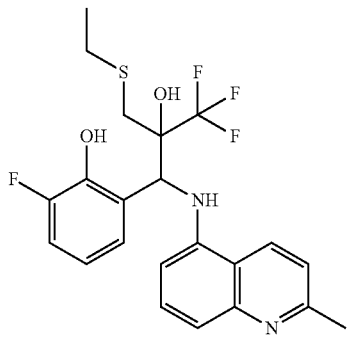

α-[(Ethylsulfanyl)methyl]-3-fluoro-2-hydroxy-β-[(2-methylquinolin-5-yl)amino]-α-(trifluoromethyl)benzenethanol ¹H-NMR (CD₃OD); δ=1.07 (t, 3H), 2.39 (dq, 2H), 2.63 (s, 3H), 2.87 (d, 1H), 2.93 (d, 1H), 5.50 (s, 1H), 6.49 (d, 1H), 6.70 (ddd, 1H), 6.95 (dd, 1H), 7.17 (d, 1H), 7.25 (d, 1H), 7.35 (m, 2H), 8.38 (d, 1H).

Example 145

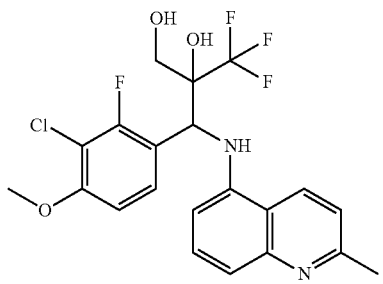

2-{(3-Chloro-2-fluoro-4-methoxyphenyl)[(2-methylquinolin-5-yl)amino]methyl}-3,3,3-trifluoropropane-1,2-diol ¹H-NMR (CD₃OD); δ=2.68 (s, 3H), 3.59 (d, 1H), 3.66 (d, 1H), 4.00 (s, 3H), 5.53 (s, 1H), 6.40 (d, 1H), 6.88 (d, 1H), 7.15 (d, 1H), 7.30 (dd, 1H), 7.35 (m, 2H), 8.36 (d, 1H).

Example 146

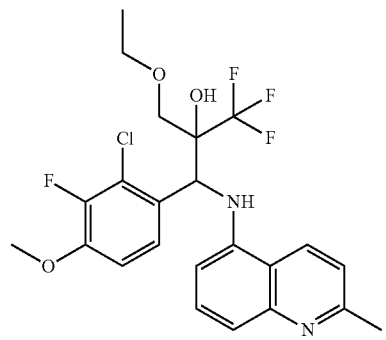

2-Chloro-α-(ethoxymethyl)-3-fluoro-4-methoxy-β-[2-methylquinolin-5-yl)amino]-α-trifluoromethyl)benzenethanol ¹H-NMR (CDCl₃); δ=1.21 (t, 3H), 2.72 (s, 1H), 3.50 (m, 3H), 3.72 (d, 1H), 3.83 (s, 3H), 5.42 (d, 1H), 6.11 (d, 1H), 6.34 (m, 1H), 6.81 (dd, 1H), 7.27 (m, 2H), 7.38 (m, 2H), 8.15 (d, 1H).

Example 147

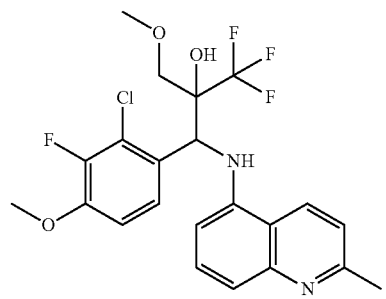

2-Chloro-3-fluoro-4-methoxy-α-(methoxymethyl)-β-[2-methylquinolin-5-yl)amino]-α-(trifluoromethyl)benzenethanol ¹H-NMR (CD₃OD); δ=2.65 (s, 3H), 3.12 (d, 1H), 3.24 (s, 3H), 3.50 (d, 1H), 3.81 (d, 3H), 5.47 (s, 1H), 6.44 (d, 1H), 6.99 (dd, 1H), 7.18 (d, 1H), 7.28 (d, 1H), 7.35 (d, 1H), 7.36 (t, 1H), 7.45 (dd, 1H), 8.34 (d, 1H).

Example 148

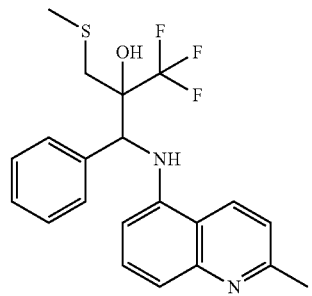

β-[(2-Methylquinolin-5-yl)amino]-α-[(methylsulfanyl)methyl]-α-(trifluoromethyl)benzenethanol $^1$H-NMR (CD$_3$OD); δ=2.08 (s, 3H), 2.42 (d, 1H), 2.65 (s, 3H), 2.90 (d, 1H), 5.12 (s, 1H), 6.42 (d, 1H), 7.33 (m, 4H), 7.60 (d, 2H), 8.41 (d, 1H).

Example 149

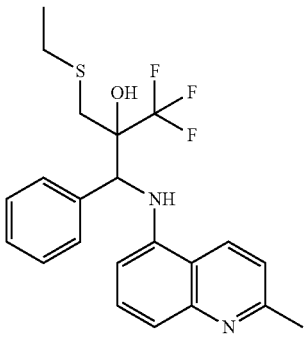

α-[(Ethylsulfanyl)methyl]-β-[2-methylquinolin-5-yl) amino]-α-(trifluoromethyl)benzenethanol $^1$H-NMR (CD$_3$OD); δ=1.16 (t, 3H), 2.45 (d, 1H), 2.50 (q, 2H), 2.64 (s, 3H), 2.92 (d, 1H), 5.09 (s, 1H), 6.42 (d, 1H), 7.16 (d, 1H), 7.33 (m, 4H), 7.61 (d, 2H), 8.41 (d, 1H).

Example 150

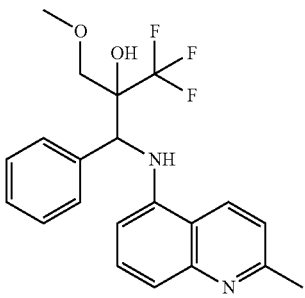

α-(Methoxymethyl)-β-[(2-methylquinolin-5-yl) amino]-α-(trifluoromethyl)benzenethanol $^1$H-NMR (CD$_3$OD); δ=2.65 (s, 3H), 3.00 (d, 1H), 3.33 (s, 3H), 3.54 (d, 1H), 5.08 (s, 1H), 6.40 (d, 1H), 7.16 (d, 1H), 7.32 (m, 4H), 7.53 (d, 2H), 8.40 (d, 1H).

Example 151

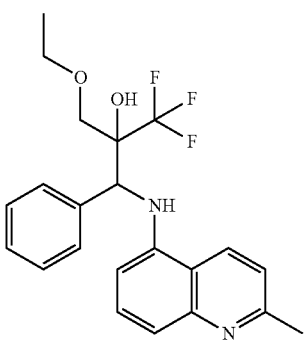

α-(Ethoxymethyl)-β-[(2-methylquinolin-5-yl) amino]-α-(trifluoromethyl)benzenethanol $^1$H-NMR (CD$_3$OD); δ=1.28 (t, 3H), 2.65 (s, 3H), 3.06 (d, 1H), 3.44 (dq, 2H), 3.59 (d, 1H), 5.08 (s, 1H), 6.40 (d, 1H), 7.16 (d, 1H), 7.24 (d, 1H), 7.32 (m, 4H), 7.53 (d, 2H), 8.40 (d, 1H).

Example 152

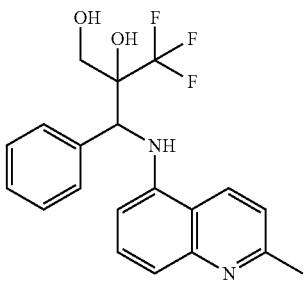

3,3,3-Trifluoro-2-{[(2-methylquinolin-5-yl)amino] phenylmethyl}propane-1,2-diol $^1$H-NMR (CD$_3$OD); δ=2.64 (s, 3H), 3.34 (d, 1H), 3.78 (d, 1H), 5.10 (s, 1H), 6.39 (d, 1H), 7.16 (d, 1H), 7.24 (d, 1H), 7.30 (m, 3H), 7.33 (d, 1H), 7.55 (d, 2H), 8.40 (d, 1H).

Example 153

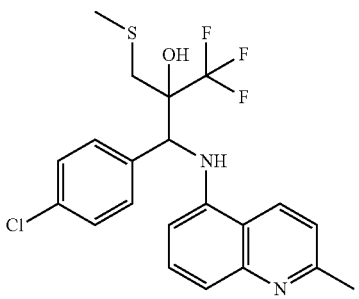

4-Chloro-β-[(2-methylquinolin-5-yl)amino]-α-[(methylsulfanyl)methyl]-α-(trifluoromethyl)benzenethanol $^1$H-NMR (CD$_3$OD); δ=2.08 (s, 3H), 2.41 (d, 1H), 2.65 (s, 3H), 2.93 (d, 1H), 5.13 (s, 1H), 6.40 (d, 1H), 7.19 (d, 1H), 7.30 (m, 2H), 7.35 (d, 2H), 7.61 (d, 2H), 8.40 (d, 1H).

Example 154

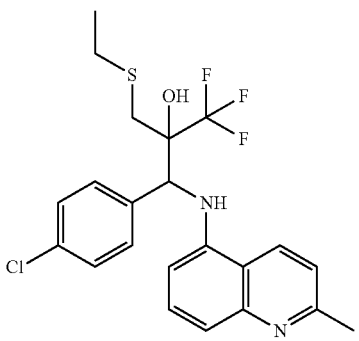

4-Chloro-α-[(ethylsulfanyl)methyl]-β-[2-methylquinolin-5-yl)amino]-α-(trifluoromethyl)benzenethanol $^1$H-NMR (CD$_3$OD); δ=1.17 (t, 3H), 2.43 (d, 1H), 2.51 (q, 2H), 2.65 (s, 3H), 2.95 (d, 1H), 5.10 (s, 1H), 6.40 (d, 1H), 7.19 (d, 1H), 7.30 (m, 2H), 7.35 (d, 2H), 7.62 (d, 2H), 8.40 (d, 1H).

Example 155

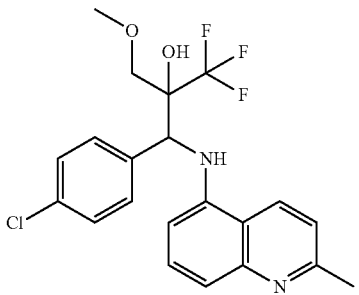

4-Chloro-α-(methoxymethyl)-β-[2-methylquinolin-5-yl)amino]-α-(trifluoromethyl)benzenethanol $^1$H-NMR (CD$_3$OD); δ=2.65 (s, 3H), 2.99 (d, 1H), 3.30 (s, 3H), 3.52 (d, 1H), 5.08 (s, 1H), 6.40 (d, 1H), 7.19 (d, 1H), 7.30 (m, 2H), 7.35 (d, 2H), 7.62 (d, 2H), 8.40 (d, 1H).

Example 156

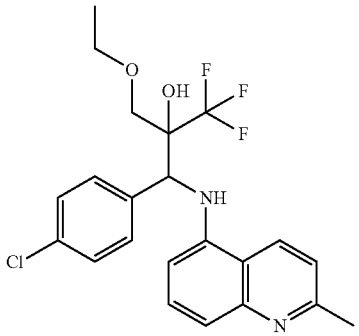

4-Chloro-α-(ethoxymethyl)-β-[2-methylquinolin-5-yl)amino]-α-(trifluoromethyl)benzenethanol $^1$H-NMR (CD$_3$OD); δ=1.26 (t, 3H), 2.65 (s, 3H), 3.02 (d, 1H), 3.43 (dq, 2H), 3.59 (d, 1H), 5.07 (s, 1H), 6.37 (d, 1H), 7.17 (d, 1H), 7.30 (m, 2H), 7.34 (d, 2H), 7.52 (d, 2H), 8.38 (d, 1H).

Example 157

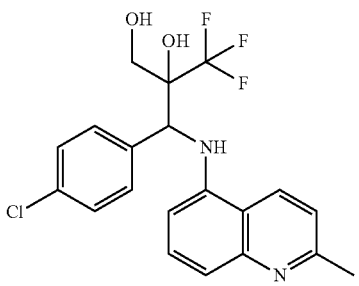

2-{(4-Chlorphenyl)[(2-methylquinolin-5-yl)amino]methyl}-3,3,3-trifluoropropane-1,2-diol $^1$H-NMR (CD$_3$OD); δ=2.65 (s, 3H), 3.27 (d, 1H), 3.79 (d, 1H), 5.11 (s, 1H), 6.36 (d, 1H), 7.16 (d, 1H), 7.30 (m, 2H), 7.34 (d, 2H), 7.55 (d, 2H), 8.39 (d, 1H).

Example 158

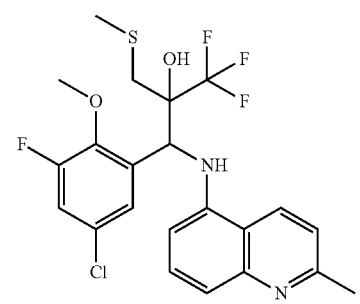

5-Chloro-3-fluoro-2-methoxy-β-[(2-methylquinolin-5-yl)amino]-α-[(methylsulfanyl)methyl]-α-(trifluoromethyl)benzenethanol $^1$H-NMR (CD$_3$OD); δ=2.06 (s, 3H), 2.65 (s, 3H), 2.81 (d, 1H), 2.91 (d, 1H), 4.09 (d, 3H), 5.55 (s, 1H), 6.47 (d, 1H), 7.14 (dd, 1H), 7.22 (d, 1H), 7.37 (m, 2H), 7.45 (dd, 1H), 8.41 (d, 1H).

Example 159

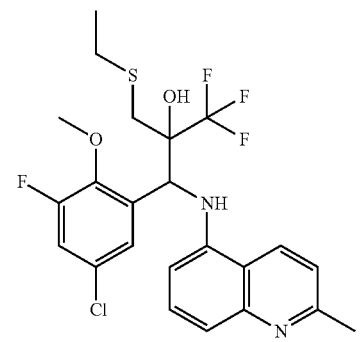

5-Chloro-α-[(ethylsulfanyl)methyl]-3-fluoro-2-methoxy-β-[(2-methylquinolin-5-yl)amino]-α-(trifluoromethyl)benzenethanol $^1$H-NMR (CD$_3$OD); δ=1.13 (t, 3H), 2.48 (q, 2H), 2.66 (s, 3H), 2.84 (d, 1H), 2.92 (d, 1H), 4.10 (d, 3H), 5.58 (s, 1H), 6.47 (d, 1H), 7.15 (dd, 1H), 7.23 (d, 1H), 7.36 (d, 1H), 7.41 (t, 1H), 7.47 (dd, 1H), 8.41 (d, 1H).

Example 160

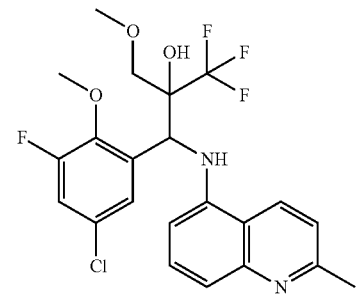

5-Chloro-3-fluoro-2-methoxy-α-(methoxymethyl)-β-[(2-methylquinolin-5-yl)amino]-α-(trifluoromethyl)benzenethanol ¹H-NMR (CDCl₃); δ=2.73 (s, 3H), 3.48 (s, 3H), 3.59 (d, 1H), 3.63 (d, 1H), 4.06 (d, 3H), 5.45 (d, 1H), 5.96 (d, 1H), 6.47 (dd, 1H), 7.05 (dd, 1H), 7.21 (dd, 1H), 7.29 (d, 1H), 7.41 (m, 2H), 8.11 (d, 1H).

Example 161

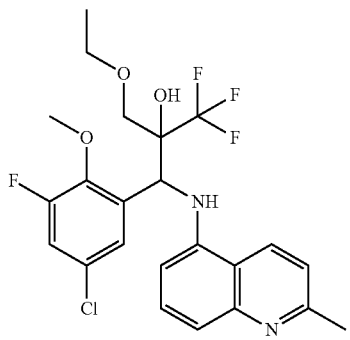

5-Chloro-α-(ethoxymethyl)-3-fluoro-2-methoxy-β-[2-methylquinolin-5-yl)amino]-α-(trifluoromethyl)benzenethanol ¹H-NMR (CD₃OD); δ=1.23 (t, 3H), 2.65 (s, 3H), 3.34 (d, 1H), 3.47 (dq, 2H), 3.61 (d, 1H), 4.05 (d, 3H), 5.54 (s, 1H), 6.50 (d, 1H), 7.13 (dd, 1H), 7.20 (d, 1H), 7.36 (m, 2H), 7.42 (dd, 1H), 8.35 (d, 1H).

Example 162

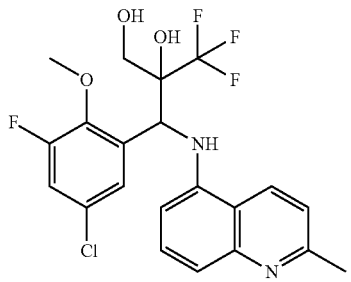

2-{(5-Chloro-3-fluoro-2-methoxyphenyl)[(2-methylquinolin-5-yl)amino]methyl}-3,3,3-trifluoropropane-1,2-diol ¹H-NMR (CDCl₃); δ=2.69 (s, 3H), 3.77 (d, 1H), 3.87 (d, 1H), 4.08 (d, 3H), 5.46 (d, 1H), 6.00 (d, 1H), 6.38 (dd, 1H), 7.03 (dd, 1H), 7.23 (d, 1H), 7.30 (dd, 1H), 7.39 (m, 2H), 8.18 (d, 1H).

Example 163

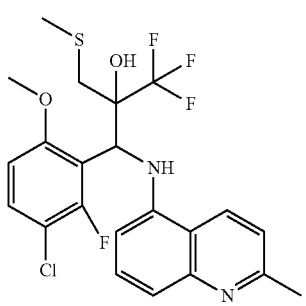

3-Chloro-2-fluoro-6-methoxy-β-[(2-methylquinolin-5-yl)amino]-α-[(methylsulfanyl)methyl]-α-(trifluoromethyl)benzenethanol ¹H-NMR (CDCl₃); δ=2.28 (s, 3H), 2.73 (s, 3H), 3.04 (d, 1H), 3.12 (d, 1H), 3.57 (s, 3H), 4.99 (d, 1H), 5.80 (d, 1H), 6.46 (d, 1H), 6.85 (d, 1H), 7.22 (d, 1H), 7.27 (d, 1H), 7.51 (d, 1H), 7.59 (d, 1H), 8.41 (d, 1H).

Example 164

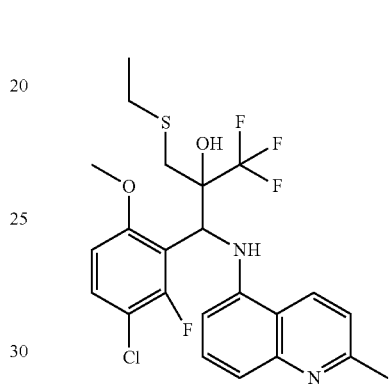

3-Chloro-α-[(ethylsulfanyl)methyl]-2-fluoro-6-methoxy-β-[(2-methylquinolin-5-yl)amino]-α-(trifluoromethyl)benzenethanol ¹H-NMR (CDCl₃); mixture of two diastereomers δ=1.21 (t, 1.5H), 1.26 (t, 1.5H), 2.60 (q, 2H), 2.72 (s, 1.5H), 2.73 (s, 1.5H), 3.05 (d, 0.5H), 3.08 (d, 0.5H), 3.18 (d, 0.5H), 3.22 (d, 0.5H), 3.88 (s, 1.5H), 3.96 (s, 1.5H), 5.64 (d, 1H), 5.76 (d, 0.5H), 5.87 (d, 0.5H), 6.60 (d, 1H), 6.66 (d, 0.5H), 6.73 (d, 0.5H), 7.27 (d, 1H), 7.25 (d, 2H), 7.45 (m, 2H), 8.11 (d, 0.5H), 8.16 (d, 0.5H).

Example 165

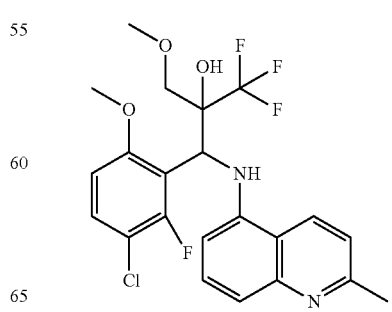

3-Chloro-2-fluoro-6-methoxy-α-(methoxymethyl)-β-[(2-methylquinolin-5-yl)amino]-α-(trifluoromethyl)benzenethanol ¹H-NMR (CDCl₃); δ=0.73 (s, 3H), 3.48 (s, 3H), 3.59 (d, 1H), 3.63 (d, 1H), 3.92 (s, 3H), 5.66 (d, 1H), 5.78 (d, 1H), 6.63 (d, 1H), 6.72 (dd, 1H), 7.23 (d, 1H), 7.27 (d, 1H), 7.41 (d, 1H), 7.50 (d, 1H), 8.07 (d, 1H).

Example 166

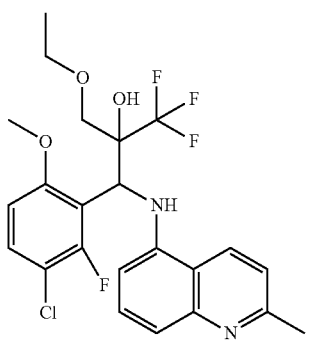

3-Chloro-α-(ethoxymethyl)-2-fluoro-6-methoxy-β-[(2-methylquinolin-5-yl)amino]-α-(trifluoromethyl)benzenethanol ¹H-NMR (CDCl₃); δ=1.17 (t, 3H), 2.71 (s, 3H), 3.48 (dq, 2H), 3.70 (d, 1H), 3.83 (d, 1H), 3.92 (s, 3H), 5.68 (d, 1H), 5.81 (d, 1H), 6.63 (d, 1H), 6.72 (dd, 1H), 7.23 (d, 1H), 7.27 (d, 1H), 7.41 (d, 1H), 7.50 (d, 1H), 8.08 (d, 1H).

Example 167

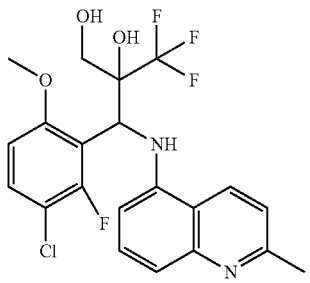

2-{(3-Chloro-2-fluoro-6-methoxyphenyl)[(2-methylquinolin-5-yl)amino]methyl}-3,3,3-trifluoropropane-1,2-diol ¹H-NMR (CD₃OD); mixture of two diastereomers δ=2.64 (s, 3H), 3.78 (s, 1.5H), 3.86 (d, 0.5H), 3.91 (d, 0.5H), 3.96 (s, 1.5H), 4.00 (d, 0.5H), 4.02 (d, 0.5H), 5.73 (s, 1H), 5.85 (s, 0.5H), 6.50 (d, 0.5H), 6.61 (d, 0.5H), 6.72 (d, 0.5H), 6.82 (d, 0.5H), 7.22 (m, 1H), 7.27 (d, 1H), 7.35 (m, 2H), 8.32 (d, 0.5H), 8.35 (d, 0.5H).

Example 168

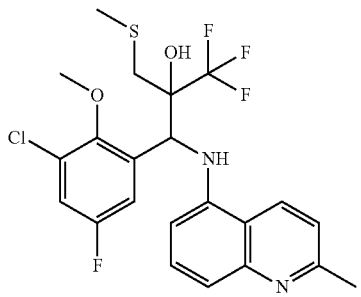

3-Chloro-5-fluoro-2-methoxy-β-[(2-methylquinolin-5-yl)amino]-α-[(methylsulfanyl)methyl]-α-(trifluoromethyl)benzenethanol ¹H-NMR (CDCl₃); δ=2.06 (s, 3H), 2.79 (s, 3H), 3.02 (s, 2H), 4.13 (s, 3H), 5.43 (d, 1H), 5.73 (d, 1H), 6.41 (dd, 1H), 7.05 (d, 1H), 7.14 (d, 1H), 7.20 (dd, 1H), 7.36 (t, 1H), 7.45 (d, 1H), 8.21 (d, 1H).

Example 169

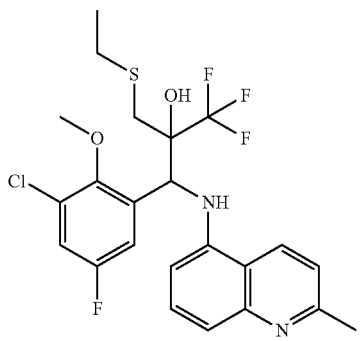

3-Chloro-α-[(ethylsulfanyl)methyl]-5-fluoro-2-methoxy-β-[(2-methylquinolin-5-yl)amino]-α-(trifluoromethyl)benzenethanol ¹H-NMR (CDCl₃); δ=1.12 (t, 3H), 2.37 (dq, 2H), 2.73 (s, 3H), 2.97 (d, 1H), 3.01 (d, 1H), 4.09 (s, 3H), 5.36 (d, 1H), 5.70 (d, 1H), 6.35 (dd, 1H), 7.10 (m, 2H), 7.29 (d, 1H), 7.39 (m, 2H), 8.16 (d, 1H).

Example 170

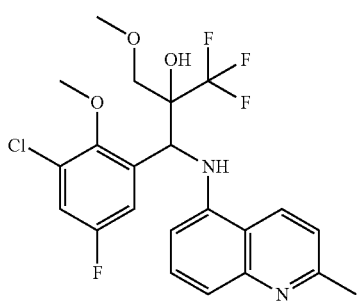

3-Chloro-5-fluoro-2-methoxy-α-(methoxymethyl)-β-[(2-methylquinolin-5-yl)amino]-α-(trifluoromethyl)benzenethanol $^1$H-NMR (CDCl$_3$); δ=2.74 (s, 3H), 3.36 (s, 3H), 3.56 (d, 1H), 3.61 (d, 1H), 4.00 (s, 3H), 5.33 (d, 1H), 5.92 (d, 1H), 6.44 (dd, 1H), 7.09 (dd, 1H), 7.17 (dd, 1H), 7.30 (d, 1H), 7.42 (m, 2H), 8.16 (d, 1H).

Example 171

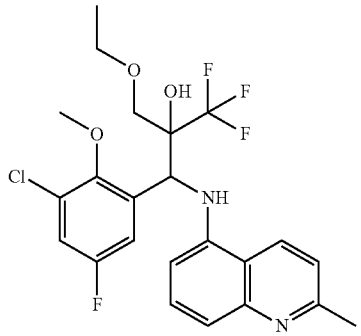

3-Chloro-α-(ethoxymethyl)-5-fluoro-2-methoxy-β-[2-methylquinolin-5-yl)amino]-α-(trifluoromethyl)benzenethanol $^1$H-NMR (CDCl$_3$); δ=1.23 (t, 3H), 2.72 (s, 3H), 3.47 (dq, 2H), 3.63 (d, 1H), 3.67 (d, 1H), 4.03 (s, 3H), 5.35 (d, 1H), 6.01 (d, 1H), 6.44 (dd, 1H), 7.08 (dd, 1H), 7.18 (dd, 1H), 7.28 (d, 1H), 7.41 (m, 2H), 8.16 (d, 1H).

Example 172

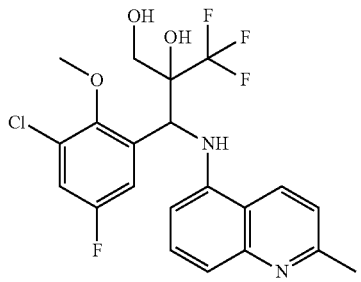

2-{(3-Chloro-5-fluoro-2-methoxyphenyl)[(2-methylquinolin-5-yl)amino]methyl}-3,3,3-trifluoropropane-1,2-diol $^1$H-NMR (CDCl$_3$); δ=2.74 (s, 3H), 3.60 (d, 1H), 3.71 (d, 1H), 4.04 (s, 3H), 5.34 (d, 1H), 5.93 (d, 1H), 6.44 (dd, 1H), 7.08 (dd, 1H), 7.18 (dd, 1H), 7.30 (d, 1H), 7.41 (m, 2H), 8.16 (d, 1H).

Example 173

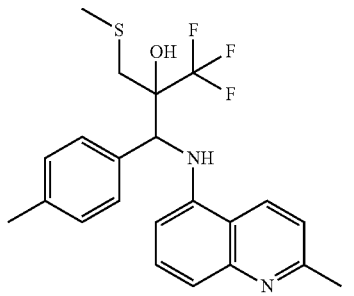

4-Methyl-β-[(2-methylquinolin-5-yl)amino]-α[(methylsulfanyl)methyl]-α-(trifluoromethyl)benzenethanol $^1$H-NMR (CD$_3$OD); δ=2.08 (s, 3H), 2.26 (s, 3H), 2.43 (d, 1H), 2.64 (s, 3H), 2.89 (d, 1H), 5.08 (s, 1H), 6.41 (d, 1H), 7.11 (d, 2H), 7.15 (d, 1H), 7.31 (t, 1H), 7.34 (d, 1H), 7.47 (d, 2H), 8.40 (d, 1H).

Example 174

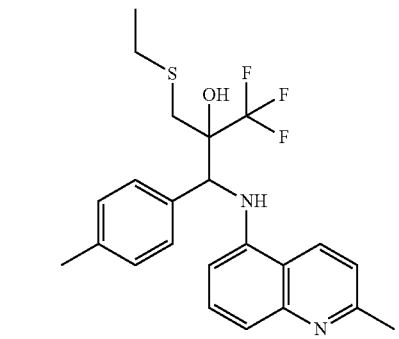

α-[(Ethylsulfanyl)methyl]-4-methyl-β-[(2-methylquinolin-5-yl)amino]-α-(trifluoromethyl)benzenethanol $^1$H-NMR (CD$_3$OD); δ=1.17 (t, 3H), 2.27 (s, 3H), 2.46 (d, 1H), 2.51 (q, 2H), 2.64 (s, 3H), 2.91 (d, 1H), 5.05 (s, 1H), 6.40 (d, 1H), 7.11 (d, 2H), 7.15 (d, 1H), 7.31 (t, 1H), 7.33 (d, 1H), 7.47 (d, 2H), 8.40 (d, 1H).

Example 175

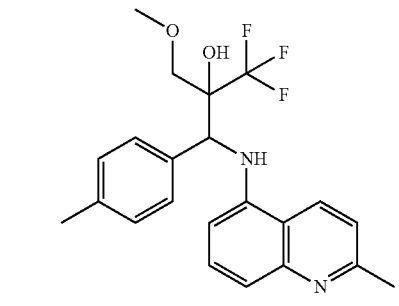

α-(Methoxymethyl)-4-methyl-β-[(2-methylquinolin-5-yl)amino]-α-(trifluoromethyl)benzenethanol $^1$H-NMR (CD$_3$OD); δ=2.26 (s, 3H), 2.64 (s, 3H), 2.98 (d, 1H), 3.30 (s, 3H), 3.50 (d, 1H), 5.01 (s, 1H), 6.38 (d, 1H), 7.11 (d, 2H), 7.14 (d, 1H), 7.30 (t, 1H), 7.33 (d, 1H), 7.37 (d, 2H), 8.37 (d, 1H).

Example 176

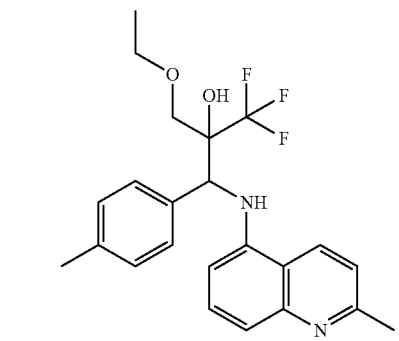

α-(Ethoxymethyl)-4-methyl-β-[(2-methylquinolin-5-yl)amino]-α-(trifluoromethyl)benzenethanol 1H-NMR (CD$_3$OD); δ=1.27 (t, 3H), 2.27 (s, 3H), 2.64 (s, 3H), 3.06 (d, 1H), 3.43 (dq, 2H), 3.57 (d, 1H), 5.02 (s, 1H), 6.38 (d, 1H), 7.10 (d, 2H), 7.13 (d, 1H), 7.30 (t, 1H), 7.33 (d, 1H), 7.38 (d, 2H), 8.37 (d, 1H).

Example 177

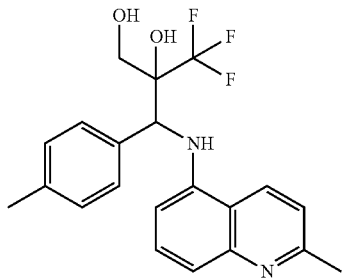

2-{(4-Methylphenyl)[(2-methylquinolin-5-yl)amino]methyl}-3,3,3-trifluoropropane-1,2-diol 1H-NMR (CD$_3$OD); δ=2.26 (s, 3H), 2.64 (s, 3H), 3.35 (d, 1H), 3.78 (d, 1H), 5.06 (s, 1H), 6.38 (d, 1H), 7.10 (d, 2H), 7.13 (d, 1H), 7.30 (t, 1H), 7.33 (d, 1H), 7.42 (d, 2H), 8.39 (d, 1H).
1H-NMR (CDCl$_3$); δ=1.18 (t, 3H), 2.45 (dq, 2H), 2.85 (d, 1H), 3.09 (d, 1H), 3.81 (s, 3H), 5.19 (d, 1H), 5.82 (d, 1H), 6.21 (d, 1H), 6.68 (m, 4H), 7.23 (t, 1H), 7.38 (t, 1H), 7.98 (d, 1H).

The invention claimed is:

1. A method for the treatment of an inflammatory disease, comprising administering to a host in need thereof an effective amount of a stereoisomer of formula I

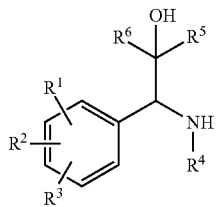

(I)

wherein
R$^1$ and R$^2$ independently of one another, mean a hydrogen atom, a hydroxy group, a halogen atom, an optionally substituted (C$_1$-C$_{10}$)-alkyl group, an optionally substituted (C$_1$-C$_{10}$)-alkoxy group, a (C$_1$-C$_{10}$)-alkylthio group, a (C$_1$-C$_5$)-perfluoroalkyl group, a cyano group, a nitro group,
or R$^1$ and R$^2$ together mean —O—(CH$_2$)$_p$—O—, —O—(CH$_2$)$_p$—CH$_2$—, —O—CH=CH—, —(CH$_2$)$_{p+2}$—, —NH—(CH$_2$)$_{p+1}$, —N(C$_1$-C$_3$-alkyl)-(CH$_2$)$_{p+1}$, or —NH—N=CH—,
in which p=1 or 2, and the terminal oxygen atoms and/or carbon atoms and/or nitrogen atoms are linked to directly adjacent ring-carbon atoms,
or NR$^7$R$^8$,
in which R$^7$ and R$^8$, independently of one another, mean hydrogen, C$_1$-C$_5$-alkyl or (CO)—(C$_1$-C$_5$)-alkyl, R$^3$ means a hydrogen atom, a hydroxy group, a halogen atom, a cyano group,
an optionally substituted (C$_1$-C$_{10}$)-alkyl group, a (C$_1$-C$_{10}$)-alkoxy group, a (C$_1$-C$_{10}$)-alkylthio group, or a (C$_1$-C$_5$)-perfluoroalkyl group,
R$^4$ means an optionally substituted phthalidyl, indolyl, isoindolyl, dihydroindolyl, dihydroisoindolyl, dihydroisoquinolinyl, dihydroquinolinyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, indolonyl, isoindolonyl, dihydroindolonyl, dihydroisoindolonyl, benzimidazole, coumarinyl, isocoumarinyl, pyrazolopyrimidinyl or indolyl group that is linked via any position,
R$^5$ means a partially or completely fluorinated C$_1$-C$_3$-alkyl group,
R$^6$ means
—(C$_3$-C$_{10}$)-alkynyl,
—(C$_1$-C$_8$)alkyl(C$_3$-C$_7$)cycloalkyl,
—(C$_2$-C$_8$)alkenyl(C$_3$-C$_7$)cycloalkyl,
—(C$_1$-C$_8$)alkylheterocyclyl,
—(C$_2$-C$_8$)-alkenylheterocyclyl,
—R$^9$,
—(C$_1$-C$_8$)alkyl-R$^9$,
—(C$_2$-C$_8$)alkenyl-R$^9$,
—(C$_3$-C$_8$)alkynyl-R$^9$,
—CH$_2$—S—(C$_1$-C$_{10}$)-alkyl,
—CH$_2$—S—R$^9$,
—CH$_2$—SO$_2$—R$^9$,
—(CH$_2$)$_n$—R$^9$,
—CH$_2$—SO$_2$—(C$_1$-C$_{10}$)-alkyl,
—(CH$_2$)$_n$—CN
—CH$_2$—O—(C$_1$-C$_{10}$)-alkyl,
—(CH$_2$)$_n$—NR$^7$R$^8$ in which R$^7$, R$^8$ have the meaning indicated above or
—CH$_2$—O—R$^9$,
in which
R$^9$ means an aryl which may optionally be substituted with 1-3 alkyl, hydroxy, halogen, cyano or C$_1$-C$_5$-alkoxy groups or
a heteroaryl group in which the heteroaryl group may contain 1-3 heteroatoms which may optionally be substituted with 1-3 alkyl, hydroxy, halogen, cyano or C$_1$-C$_5$-alkoxy groups,
n means an integer selected from 1, 2, 3, 4, 5.

2. The method according to claim 1, wherein at least one of the groups R$^1$-R$^3$ is C$_1$-C$_5$-alkyl, C$_1$-C$_5$-alkoxy, C$_1$-C$_5$-alkylthio, C$_1$-C$_5$-perfluoroalkyl, halogen, hydroxy, cyano, nitro, —O—(CH$_2$)$_p$—O—, —O—(CH$_2$)$_p$—CH$_2$—, —O—CH=CH—, —(CH$_2$)$_{p+2}$—, —NH—(CH$_2$)$_{p+1}$, N(C$_1$-C$_3$-alkyl)-(CH$_2$)$_{p+1}$, or —NH—N=CH—,
in which p=1 or 2, and the terminal oxygen atoms and/or carbon atoms are linked with directly adjacent ring-carbon atoms,
or NR$^7$R$^8$,
in which R$^7$ and R$^8$, independently of one another, can be hydrogen, C$_1$-C$_5$-alkyl or (CO)—C$_1$-C$_5$-alkyl.

3. The method according to claim 1, wherein at least one of the groups R$^1$-R$^3$ is selected from the group hydroxy, methoxy, fluoro, chloro,
or in which 2 adjacent groups R$^1$-R$^3$ form a —O—CH$_2$—O—, a —CH$_2$—CH$_2$—O— or a —CH$_2$—C(CH$_3$)$_2$—O— group.

4. The method according to claim 1, wherein ring system contained in $R^4$ is substituted with 1 to 3 of the same or different radicals from the group $C_1$-$C_3$-alkyl, hydroxy, carbonyl or halogen.

5. The method according to claim 4, wherein ring system contained in $R^4$ is substituted with methyl, chlorine or fluorine.

6. The method according to claim 4, wherein $R^4$ is phenyl, naphthyl, quinolin-5-yl, phthalazinyl or quinazolinyl, which can be optionally substituted independently with 1-3 radicals selected from the group carbonyl, $C_1$-$C_3$-alkyl, chlorine or fluorine.

7. The method according to claim 1, wherein $R^5$ is selected from —$CF_3$ and —$C_2F_5$.

8. The method according to claim 1, wherein $R^6$ is benzyl, ethylsulfanylmethyl, (imidazol-2-yl)-sulfanylmethyl, (imidazol-2-yl)-sulfonylmethyl, 1,2,4-triazol-3-ylsulfanylmethyl, (1-methyl-imidazol-2-yl)-sulfanylmethyl, (1H-imidazol-2-yl)-sulfanylmethyl, pyrimidine-2-yl-sulfanylmethyl, 2-propylsulfanylmethyl, cyanomethyl, methylsulfanylmethyl, dimethylaminomethyl, methoxymethyl, hydroxymethyl, or ethoxymethyl.

9. The method according to claim 1, wherein at least one of $R^1$, $R^2$, $R^3$ is methoxy, hydroxy, fluoro, chloro, methyl, or $R^1$ and $R^2$ together mean —O—$CH_2$—O—, —$CH_2$—$CH_2$—O— or —$CH_2$—$C(CH_3)_2$—O— (forming together with the phenyl group to which they are bound a five membered ring),
$R^4$ is quinolin-5-yl, phthalazinyl, quinazolinyl which can be substituted independently one or two times by carbonyl, methyl or fluorine $R^5$ is —$CF_3$
$R^6$ is benzyl, propyl, chloromethyl, bromomethyl, ethylsulfanylmethyl, (imidazol-2-yl)-sulfanylmethyl, (imidazol-2-yl)-sulfonylmethyl, 1,2,4-triazol-3-ylsulfanylmethyl, (1-methyl-imidazol-2-yl)-sulfanylmethyl, (1H-imidazol-2-yl)-sulfanylmethyl, pyrimidine-2-yl-sulfanylmethyl, 2-propylsulfanylmethyl, cyanomethyl, methylsulfanylmethyl, dimethylaminomethyl, methoxymethyl, hydroxymethyl, or ethoxymethyl.

10. The method according to claim 1, wherein the stereoisomer is in enantiomerically pure form.

* * * * *